United States Patent [19]

Macrae et al.

[11] Patent Number: 5,826,237
[45] Date of Patent: Oct. 20, 1998

[54] APPARATUS AND METHOD FOR MERGING MEDICAL PROTOCOLS

[75] Inventors: Kenneth I. Macrae, San Francisco; Annsheng C. Ting, Los Altos Hills; Ragnar W. Edholm, Sunnyvale; Erik Worth, Milpitas; Robert B. Sigmon, Jr., Redwood City; Toshikazu Matsumoto, Half Moon Bay; Chung-Jen Ho, San Jose, all of Calif.

[73] Assignee: Araxsys, Inc., Redwood City, Calif.

[21] Appl. No.: 546,213

[22] Filed: Oct. 20, 1995

[51] Int. Cl.⁶ .............................. G06F 17/60; G06F 7/14
[52] U.S. Cl. .................................. 705/2; 705/3; 707/100; 707/104
[58] Field of Search ..................................... 345/326, 333, 345/334, 340, 348, 352, 353; 705/2, 3, 7, 8; 707/100, 104

[56] References Cited

U.S. PATENT DOCUMENTS

| 1,988,634 | 1/1935 | Stonecypher ................................. 35/12 |
| 3,186,111 | 6/1965 | Lawlor ......................................... 35/17 |
| 3,566,370 | 2/1971 | Worthington, Jr. et al. ......... 340/172.5 |

(List continued on next page.)

FOREIGN PATENT DOCUMENTS

| 0 457 000 A2 | 3/1991 | European Pat. Off. . |
| 0 607 694 A1 | 7/1994 | European Pat. Off. . |
| 4122143.5 | 1/1993 | Germany . |
| 920113354 | 6/1992 | Japan . |
| 1 383 811 | 2/1975 | United Kingdom . |
| 1 467 298 | 3/1975 | United Kingdom . |
| 1 400 501 | 7/1975 | United Kingdom . |
| 1 403 552 | 8/1975 | United Kingdom . |
| WO 88/01824 | 3/1988 | WIPO . |
| WO 91/00575 | 1/1991 | WIPO . |

OTHER PUBLICATIONS

Fisherkeller, et al., "Evaluation of a Computer–Assisted Dental Diagnostic System by Navy Hospital Corpsmen," NSMRL Report 1141, Naval Submarine Medical Research Laboratory, Jun. 23, 1989.

Roger, et al., "Nursing Workload Management for a Patient Data Management System," Proceedings of the 5th Annual IEEE Symposium on Computer–Based Medical Systems, Jun. 14–17, 1992, Durham, NC; pp. 216–223.

"Graphical Procedural Capability," IBM Technical Disclosure Bulletin, vol. 33, No. 11, Apr. 1991, pp. 184–191.

*Primary Examiner*—Edward R. Cosimano
*Attorney, Agent, or Firm*—D'Alessandro & Ritchie

[57] ABSTRACT

An apparatus and method for providing a medical protocol graphic user interface which graphically merges medical treatments is provided. The apparatus and method generates a plurality of graphic images representing a medical treatment plan. The graphic images are presented in a chronological order based in real or virtual time slots and may be viewed in either a flow chart or a chart view format. The chart view format may be used by healthcare professionals to enter data. The graphical images include an order node, result node and flow node. The various nodes may be connected to form a healthcare plan assigned to a patient. Two separate medical treatment plans may be combined with duplicate or conflicting orders removed.

32 Claims, 39 Drawing Sheets

U.S. PATENT DOCUMENTS

| | | | |
|---|---|---|---|
| 3,615,901 | 10/1971 | Medicus | 148/11.5 |
| 3,794,982 | 2/1974 | McCormick et al. | 340/172.5 |
| 3,810,102 | 5/1974 | Parks, III et al. | 340/172.5 |
| 3,831,608 | 8/1974 | Kletschka et al. | 128/35 |
| 3,910,281 | 10/1975 | Kletschka et al. | 128/335 |
| 3,916,909 | 11/1975 | Kletschka et al. | 128/354 |
| 3,931,821 | 1/1976 | Kletschka et al. | 128/35 |
| 3,934,226 | 1/1976 | Stone et al. | 340/172.5 |
| 3,957,389 | 5/1976 | Rafferty et al. | 415/7 |
| 3,970,408 | 7/1976 | Rafferty et al. | 415/60 |
| 3,970,996 | 7/1976 | Yasaka et al. | 340/172.5 |
| 3,976,253 | 8/1976 | Medicus | 241/167 |
| 3,980,086 | 9/1976 | Kletschka et al. | 128/318 |
| 4,009,719 | 3/1977 | Kletschka et al. | 128/333 |
| 4,037,984 | 7/1977 | Rafferty et al. | 415/60 |
| 4,049,002 | 9/1977 | Kletschka et al. | 128/318 |
| 4,096,864 | 6/1978 | Kletschka et al. | 128/354 |
| 4,290,114 | 9/1981 | Sinay | 364/900 |
| 4,315,309 | 2/1982 | Coli | 364/200 |
| 4,360,345 | 11/1982 | Hon | 434/262 |
| 4,450,076 | 5/1984 | Medicus et al. | 210/242.1 |
| 4,464,122 | 8/1984 | Fuller et al. | 434/262 |
| 4,488,322 | 12/1984 | Hunt et al. | 5/453 |
| 4,489,387 | 12/1984 | Lamb et al. | 364/514 |
| 4,525,885 | 7/1985 | Hunt et al. | 5/453 |
| 4,567,318 | 1/1986 | Shu | 174/35 |
| 4,583,524 | 4/1986 | Hutchins | 128/1 R |
| 4,667,292 | 5/1987 | Mohlenbrock et al. | 364/406 |
| 4,731,725 | 3/1988 | Suto et al. | 364/415 |
| 4,733,354 | 3/1988 | Potter et al. | 364/415 |
| 4,737,912 | 4/1988 | Ichikawa | 364/413 |
| 4,755,868 | 7/1988 | Hodges | 358/60 |
| 4,764,806 | 8/1988 | Altman | 358/60 |
| 4,813,013 | 3/1989 | Dunn | 364/900 |
| 4,839,822 | 6/1989 | Dormond et al. | 364/513 |
| 4,842,394 | 6/1989 | Buchroeder | 350/432 |
| 4,858,126 | 8/1989 | Croce, Jr. | 364/413.02 |
| 4,893,270 | 1/1990 | Beck et al. | 364/900 |
| 4,899,758 | 2/1990 | Finkelstein et al. | 128/672 |
| 4,920,514 | 4/1990 | Aoki | 364/521 |
| 4,945,476 | 7/1990 | Bodick et al. | 364/413.02 |
| 5,018,067 | 5/1991 | Mohlenbrock et al. | 364/413.02 |
| 5,025,374 | 6/1991 | Roizen et al. | 364/413.02 |
| 5,029,081 | 7/1991 | Kagawa | 364/413.01 |
| 5,077,666 | 12/1991 | Brimm | 364/413.02 |
| 5,084,819 | 1/1992 | Dewey et al. | 364/419 |
| 5,088,037 | 2/1992 | Battaglia | 364/413.01 |
| 5,090,648 | 2/1992 | Wood, IV | 248/125 |
| 5,147,186 | 9/1992 | Buckholtz | 417/420 |
| 5,208,748 | 5/1993 | Flores et al. | 364/419 |
| 5,216,603 | 6/1993 | Flores et al. | 364/419 |
| 5,225,976 | 7/1993 | Tawil | 364/401 |
| 5,243,531 | 9/1993 | DiPippo et al. | 364/468 |
| 5,253,164 | 10/1993 | Holloway et al. | 364/406 |
| 5,255,358 | 10/1993 | Busboom et al. | 395/153 |
| 5,337,402 | 8/1994 | Kitagawa et al. | 345/433 |
| 5,404,292 | 4/1995 | Hendrickson | 364/413 |
| 5,412,804 | 5/1995 | Krishna | 395/600 |
| 5,539,869 | 7/1996 | Spoto et al. | 395/154 |
| 5,583,758 | 12/1996 | McIlroy et al. | 395/202 |
| 5,608,898 | 3/1997 | Turpin et al. | 395/619 |
| 5,640,501 | 6/1997 | Turpin | 395/768 |
| 5,644,778 | 7/1997 | Burks et al. | 395/800 |
| 5,660,176 | 8/1997 | Iliff | 128/630 |

Order Node Detail

Attributes | Content

[ Add ] [ Replace ] [ Edit ] [ Delete ]
— 120

|   | Category | Department | Name | Cost |
|---|----------|------------|------|------|
| 1 | Lab | Bacteriology | Strep | $40.00 |
| 2 | Vitals | Nursing | Routine | $20.00 |

— 110

[ OK ] [ Cancel ] [ Apply ] [ Help ]

Results Node Detail

Attributes | Content — 142

[ Split ]     [ Status ]

Labs: Bacteriology: Strep Not Done
Vitals: Nursing: Routine Not Done

143

— 140

[ OK ] [ Cancel ] [ Apply ] [ Help ]

| Result Form | | | | |
|---|---|---|---|---|
| Done | Cancel | | Help | |
| | 151 | | | |
| Reporter | | Status: Not Done | | |
| | Val | Min | Max | |
| Temperature | 0.00 | | | |
| Resp Rate | 0.00 | | | |
| Pulse | 0.00 | | | |
150
FIG. 15
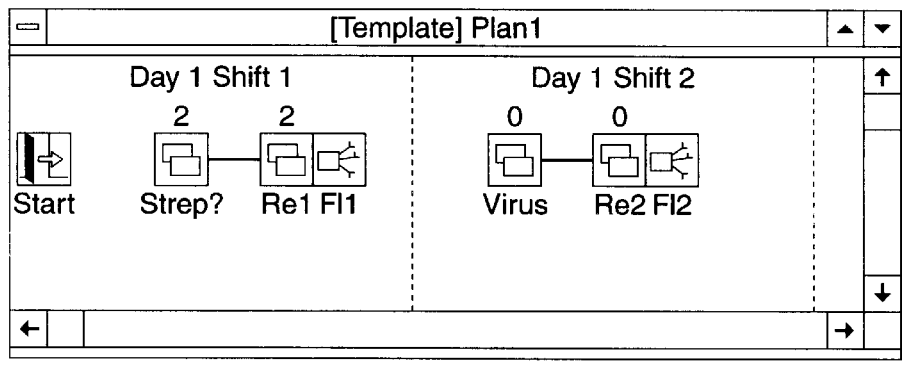
FIG. 16
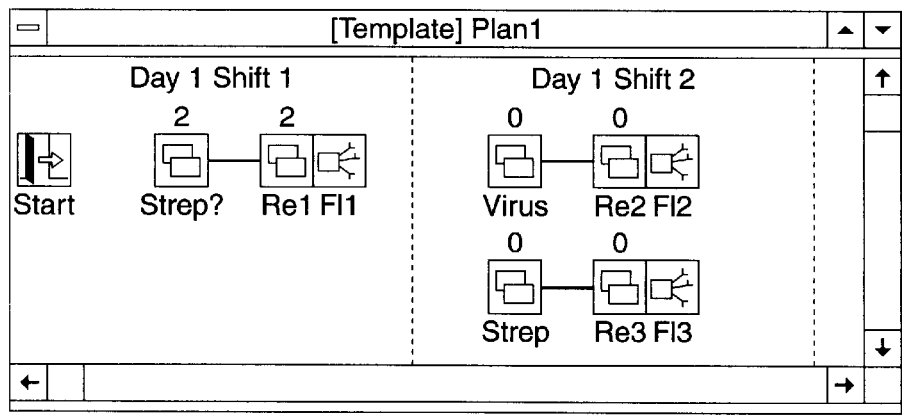
FIG. 17

| | Day 1 | | |
|---|---|---|---|
| | screen.pln Sore Throat | screen.pln RE1 | screen.pln infect.pln |
| 1 | Medicine Sore Throat | Done | Not Done /291 |
| 2 | | | |

[Plan:Jim Harding]screen.pln
Current Cost $5
Chart View

| ST | Start | | | | | |
|---|---|---|---|---|---|---|
| GO | Virus | DCPlan | Clinic | | | |
| RE | R1 | DC-Instructions_for_Virus | | | Not Done | O1 |
| OF | D1 | IfRule | Default | | | |
| | | | E0 | 100 | | |
| GO | Strep | DCPlan | Clinic | 0 | | |
| RE | R2 | DC-Instructions_for_Bacteria | Done | | Done | D2 |
| OF | D2 | IfRule | Default | | | |
| | | | E0 | 100 | | |
| GO | Strep | Meds | Pharmacy | 10 | 10mg Tabs PO | Done | D2 |
| RE | R2 | PO_Penicillin | Done | | | |
| | | | PO_Penicillin | | | |
| GO | Strep? | Labs | Bacteriology | 40 | Throat | Done | D0 |
| RE | R0 | Test | Done | | | |
| OF | D0 | IfRule | Default | 90 | | |
| OF | D0 | IfRule | R0:Strep:Test:Value | 10 | | |
| GO | Strep? | Vitals | Nursing | 20 | | Done | D0 |
| RE | R0 | Temperature | Done | Val=35.00 | Min=30.00 | Max=40.00 | Units=C |
| RE | R0 | Resp Rate | Done | Val=90.00 | Min=0.00 | Max=100.00 | Units=8PM |
| RE | R0 | Pulse | Done | Val=240.00 | Min=0.00 | Max=250.00 | Units=8PM |
| | | | | | | |
| EX | E0 | | | | | |

*FIG. 41*

APPARATUS AND METHOD FOR MERGING MEDICAL PROTOCOLS

BACKGROUND OF THE INVENTION

1. Field of the Invention

The present invention relates to providing graphic medical healthcare plans (protocols) and in particular a graphic user interface, for developing, viewing and implementing medical healthcare plans.

2. Description of the Related Art

Typically, developing a healthcare plan for providing medical services to patients has been a manual exercise. Often, a physician will construct a medical healthcare plan, including when and how certain medical services should be provided to patients on written charts or verbally to medical care providers. Generic medical healthcare plans have been developed by clinicians and committees, with input from other appropriate members of an interdisciplinary care team. However, adapting a generic plan to a specific patient further requires valuable time and effort to coordinate and manage the task. In implementing a medical healthcare plan, a variety of individuals will be responsible for providing different types of care to the patient and possibly entering results from the care provided.

As can be seen, a number of problems are associated with developing and implementing present-day healthcare plans. First, communication between those generating the healthcare plan and those implementing the healthcare plan may be ineffective. For example, often, a physician will write brief notes on a chart regarding patient treatment. These brief notes may be interpreted erroneously, leading to wasted time and cost, and possibly detrimental care provided to the patient. Also, a chronological list of various treatments or services is generally not completed before the healthcare plan is initiated. If a complete healthcare plan is developed before treatment is initiated, possible errors or duplication in treatment may be revealed, and thus avoided, in a particular healthcare plan.

Second, once a healthcare plan is developed for a particular patient under a certain set of circumstances, often it is difficult to retain or duplicate that plan for likewise patients with similar circumstances. Thus, valuable time may be wasted in developing an identical or similar plan. Moreover, if a healthcare plan requires a slight modification, an entire medical healthcare plan must be developed including the slight modification instead of revising an existing healthcare plan.

In addition, when a healthcare planner orders a particular treatment, such as a laboratory test, there may be different test results which may require alternate further treatment. With present medical healthcare plans, it is difficult to construct a healthcare plan based upon various results from a specific treatment. A healthcare treatment plan may also include multiple healthcare treatments, such as multiple laboratory tests, further complicating a healthcare plan.

Fourth, obtaining costs in typical medical healthcare plans is difficult. As described above, there may be alternate treatments, depending upon different laboratory test results; thus, projecting costs for a particular health treatment plan must take into account multiple types of potential treatments based on different results from various treatment procedures. Without knowing specific costs associated with each step in the medical healthcare plan, it is difficult for hospital administrators to manage costs and allocate limited resources.

Fifth, often a patient may require multiple healthcare plans that must be reconciled or merged into one plan. For example, if a patient is admitted to a hospital for a hip replacement and subsequently is diagnosed as having an infection, two separate healthcare plans must be implemented. These two plans can be carried out in parallel or merged in one to be carried out as one plan. In either case, a healthcare plan for the hip replacement must be reconciled with the healthcare plan for the infection. The timing and types of treatment, including drug dosages, must be reconciled in order to provide treatment for both conditions.

Finally, once a successful medical health treatment plan is developed, reusing that plan, or transferring that plan to other healthcare providers, is limited. For example, a leading cardiologist who develops a healthcare plan for a new surgical procedure may not be able to readily transfer the healthcare plan to other cardiologists to be adapted and used in their practices. Thus, valuable time and effort would be saved in developing a single successful medical healthcare treatment plan and transferring it to other healthcare providers.

Therefore, it is desirable to provide an apparatus and method for providing a medical healthcare plan which will 1) reduce errors associated with communications between healthcare planners and providers; 2) allow for convenient modification of medical health treatment plans; 3) provide costs associated with each step in the medical health treatment plan, as well as the total cost of the medical health treatment plan; 4) reconcile two or more healthcare plans; and 5) copy and transfer medical treatment plans to various medical healthcare providers.

SUMMARY OF THE INVENTION

Other aspects and advantages of the present invention can be seen upon review of the figures, the detailed description, and the claims which follow.

According to the present invention, a data processing apparatus is provided. The data processing apparatus comprises a display for displaying data and input means for inputting data. A storage location is coupled to the display and the input means. Processing means controls the storage means, input means and the display means in response to stored programs and input data. The display includes a plurality of graphic icon images, stored in the storage location, arranged on the display representing a medical treatment plan. A program merges a first set of graphic icon images with a second set of graphic images to obtain a combined treatment plan.

According to an aspect of the present invention, the first set of icon images are arranged in a chronological order and a first icon image represents the medical order. The icon images may be assigned to a patient. Further, the first set of icon images and the second set of icon images may be arranged in a combined chart view.

According to another aspect of the present invention, the first set of graphic icon images includes at least one order triplet having an order node, result node and flow control node.

According to yet another aspect of the present invention, a method for displaying a graphic representation of a medical treatment plan is provided. The method comprises the steps of providing a first and second set of icon images representing a first and second medical treatment. The first set of icon images are combined with the second set of icon images to obtain a third set of icon images representing a merged medical treatment, including the first and second medical treatments.

According to another aspect of the present invention, the method step for providing a first set of icon images further includes the step of arranging the first set of icon images in corresponding time slots with the second set of icon images.

According to still another aspect of the present invention, the method step for providing a first set of graphic icon images includes a step for providing a order triplet. The order triplet includes an order node, result node and Flow Chart node.

According to another aspect of the present invention, the method further includes the step of providing a first order icon image having a corresponding order description and providing a second order icon image having a corresponding order description.

According to another aspect of the present invention, the method step of combining further includes the step of combining the first order description with the second order description.

According to another aspect of the present invention, an article of manufacture, including a computer readable medium having a computer readable program means for displaying a medical treatment plan is provided. The computer readable program code means in the article of manufacture comprises a computer readable program code means for causing a computer to generate an image on a display representing a medical treatment. The article of manufacture further includes computer readable program code means for causing a computer to generate a first and second image representing a first and second medical treatment, respectively, on a display. Computer readable program code means are also provided for combining the first and second image to display a combined medical treatment plan. The first image includes an order triplet, including an order node, a result node and a flow control node.

According to another aspect of the present invention, the article of manufacture further includes a computer readable program code means for causing a computer to generate a chart view of the first and second images.

According to still another aspect of the present invention, the article of manufacture further includes computer readable program code means for causing a computer to generate the merging medical treatment image in time slots on a display corresponding to the first and second medical treatment image. The first medical treatment image is the master treatment image, while the second medical treatment image is the merging treatment image.

According to another aspect of the present invention, the article of manufacture further includes computer readable program means for causing a computer to compare a first order node image to a second order node image.

BRIEF DESCRIPTION OF THE DRAWINGS

FIG. 13 illustrates the Order Node detail box according to the present invention.

FIG. 14 illustrates the Result Node detail dialog box according to the present invention.

FIG. 15 illustrates the Results Form dialog box according to the present invention.

FIG. 16 illustrates adding the virus triplet according to the present invention.

FIG. 17 illustrates adding the strep triplet according to the present invention.

Figure 39:
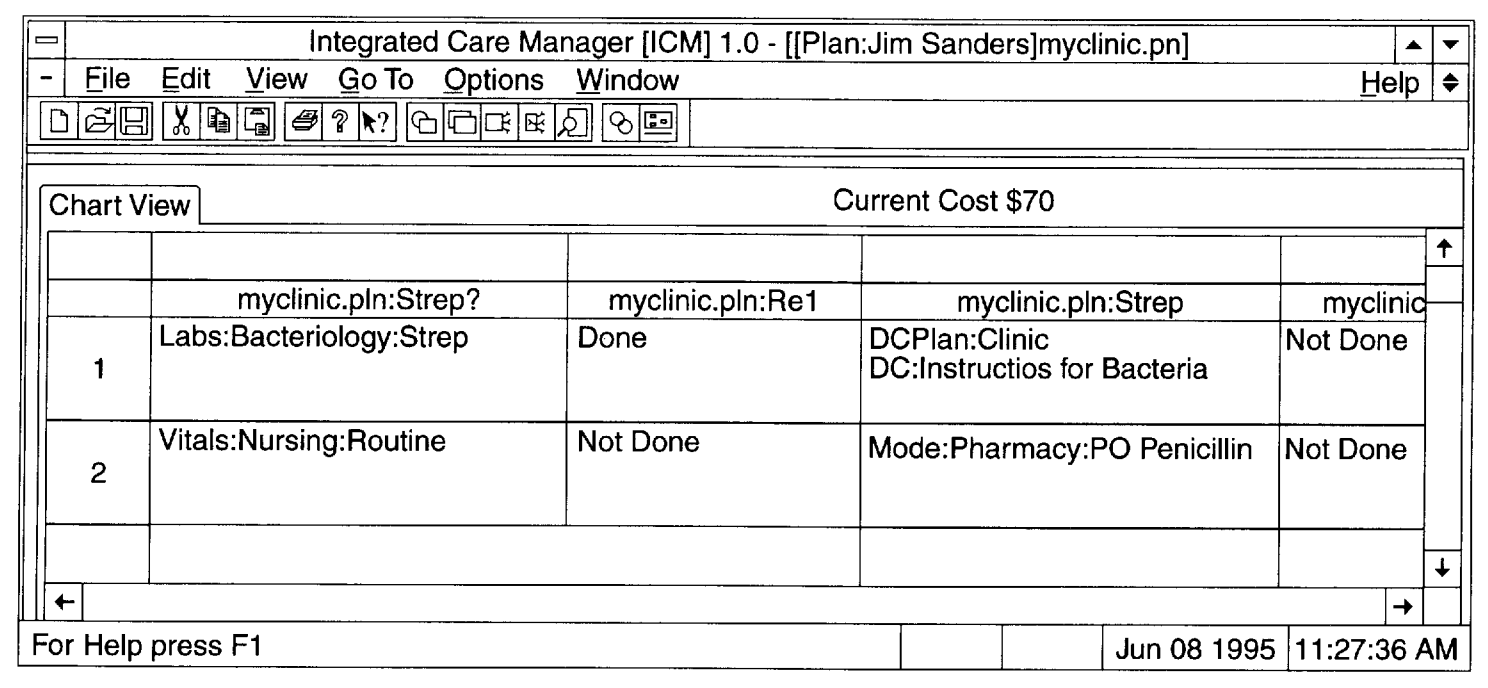

FIGS. 37–39 illustrates a patient chart according to the present invention.

FIG. 41 illustrates the plan elements exported from the "clinic.pln" and imported into an Excel spreadsheet according to the present invention.

DETAILED DESCRIPTION OF THE INVENTION

I. OVERVIEW

A. Software and Hardware Environment

The term "template" is used to refer to a generic healthcare treatment plan, protocol, or guideline. After a template has been assigned to a general patient or client, the template is referred to as "plan".

The software or computer readable program code, according to one embodiment, used in developing, displaying and implementing templates and healthcare treatment plans, is named the ARAXSYS™ Solution. In a preferred embodiment, the ARAXSYS™ Solution software is stored on a computer readable medium.

The ARAXSYS™ Solution program is written in C++ language and is stored on a computer readable disk. In the preferred embodiment, the ARAXSYS™ Solution software program would be used in conjunction with a computer system having the following requirements. The computer is an International Business Machine ("IBM") compatible computer having a 386, 486 or Pentium processor. The operating system would be either a MICROSOFT® WINDOWS® 3.1, WINDOWS® for 3.11, WINDOWS® 95 or WINDOWS™ NT operating system. The minimum random access memory ("RAM") would be 8 megabytes ("MB") and preferably 16 MB. For relatively small RAM systems, virtual memory must be set as high as possible. In an embodiment, virtual memory must be set to a minimum of 12 MB In the preferred embodiment, the Araxsys™ Solution program would operate in conjunction with MICROSOFT foundation class ("MFC") software files and with WIN 32s software files in a 16-bit environment. Available hard disk drive space should include 2 to 7 megabytes depending on the size of the data and whether or not MFC or WIN 32s system files are being used. The monitor would preferably be a video graphic adapter ("VGA") or super video graphic adapter ("SVGA") color monitor.

In the preferred embodiment, the computer system would have an input/output device, such as a mouse, for "clicking" graphic elements. Clicking graphic elements refers to positioning a cursor on a display, which is controllable by the mouse, on or near a graphic element and pushing a mouse button.

B. Graphic User Interface Overview

FIGS. 1–5 illustrate a general overview of display windows and features used in the present graphic user interface according to the present invention.

Figure 1:
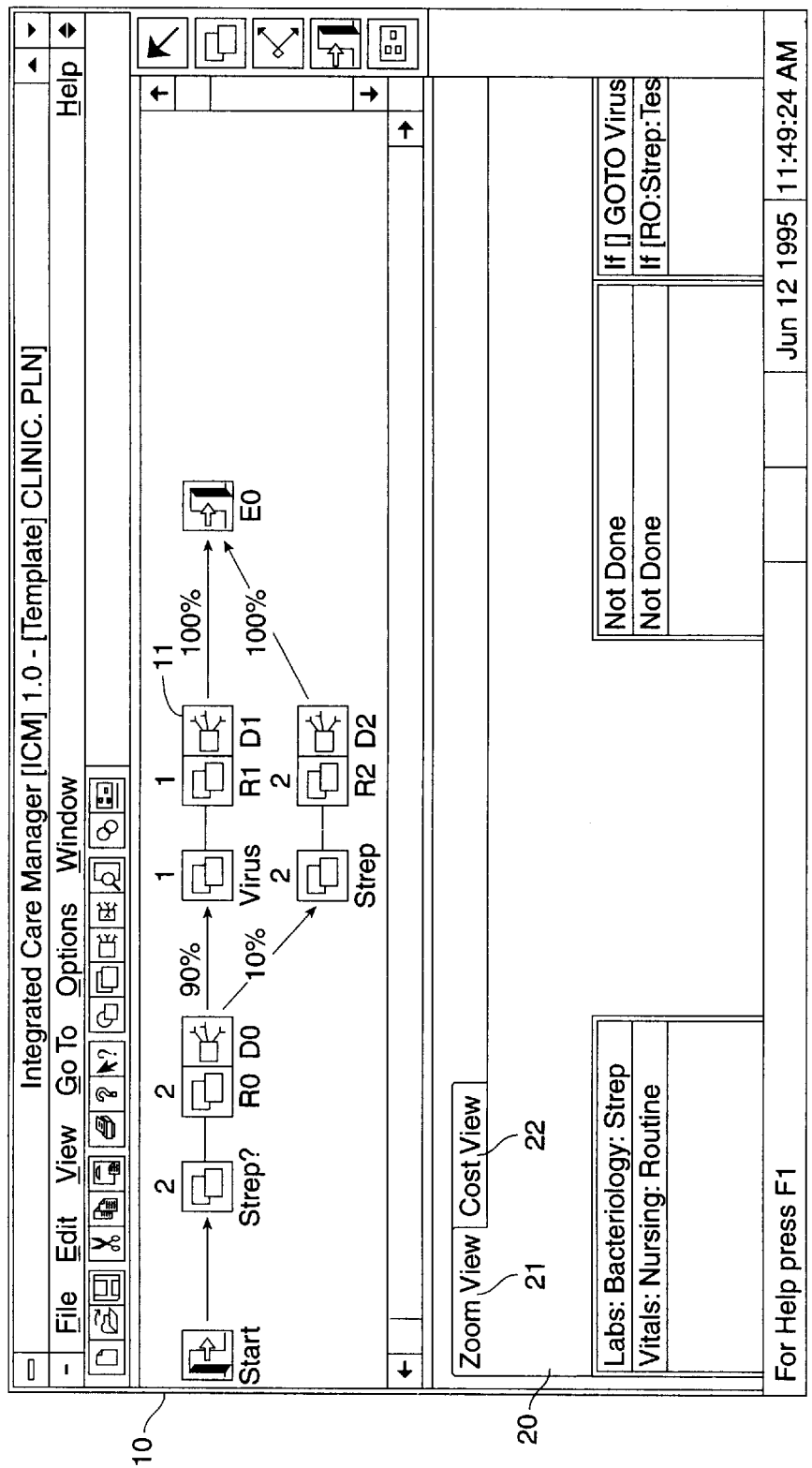
FIG. 1 illustrates an example of a Template Builder window with an open template according to the present invention.
Figure 3:
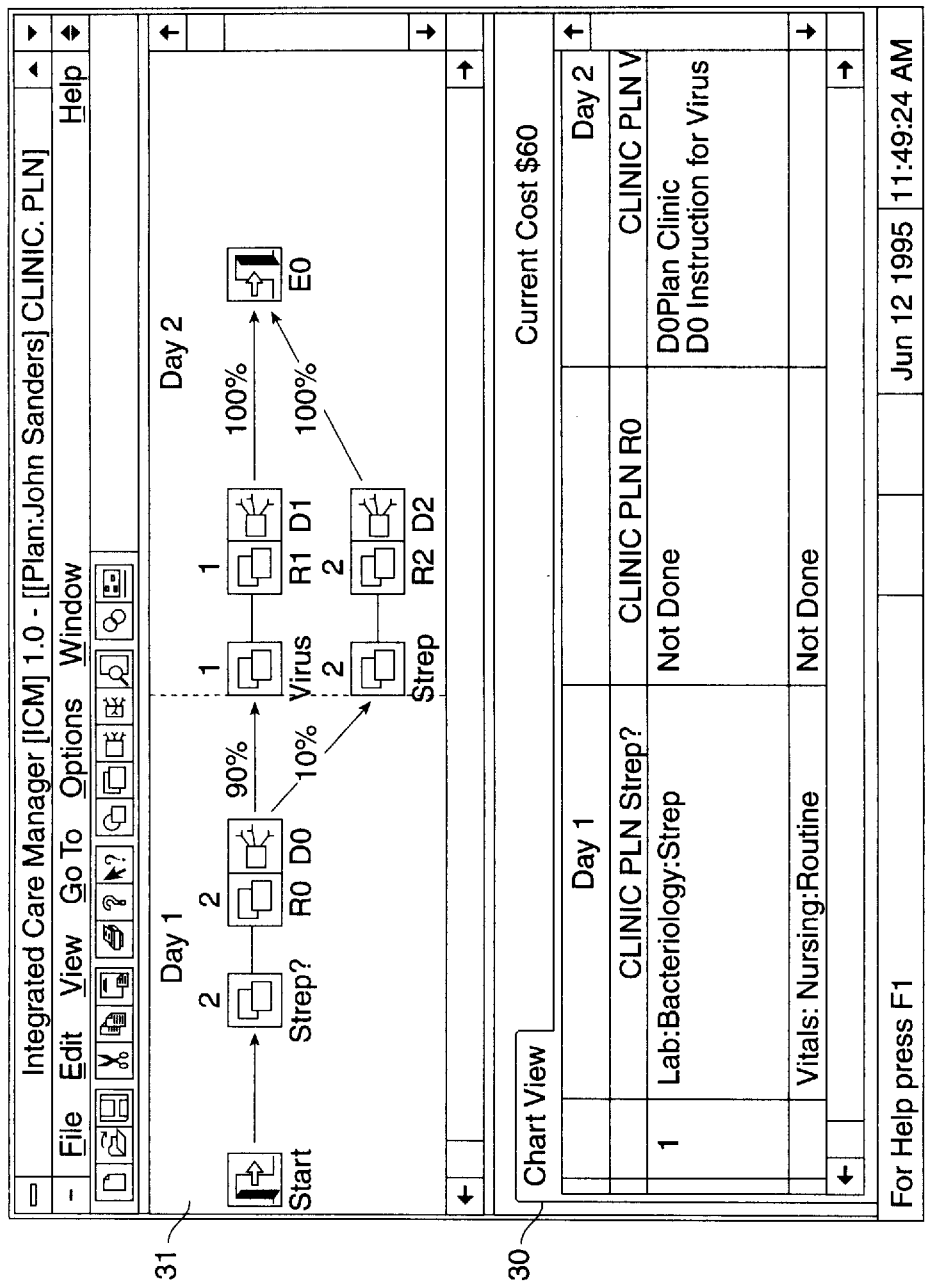
FIG. 3 illustrates an example of Patient Charting view according to the present invention.

FIG. 1 illustrates an example of a Template Builder window with an open template. The template graphically represents a medical healthcare treatment plan in upper window 10. The upper window 10 shows a Flow Chart view 11 of a medical healthcare treatment plan. The template contains a number of graphic elements including: a start node, three triplets of an order node, a result node, a flow control node and an exit node. These graphical elements are positioned in window 10 in order to represent a medical healthcare treatment plan. The graphical elements can be positioned in time slots, as seen in FIG. 3, which will be discussed in detail below.

In Flow Chart view 11, the process flow begins with a Start node, enters into the first Order nodes, and flows out to Result nodes. After the results are entered, the process flow continues on to a Flow Control node where the next step in the treatment is determined. As described below, there are three types of process flows.

The bottom viewing window 20 contains two different views of the template, each on separate tabs: Zoom view 21 and Cost view 22. A user flips between these views by clicking the corresponding tab. A user can also choose Zoom view and Cost view options from a View menu to show a specific template view.

The Zoom view is used to see the details inside the nodes of the template. Each node is magnified or expanded to show information contained within, as well as the relationships between the nodes in the flow chart. A user can use this view to examine the entire template.

Figure 2:
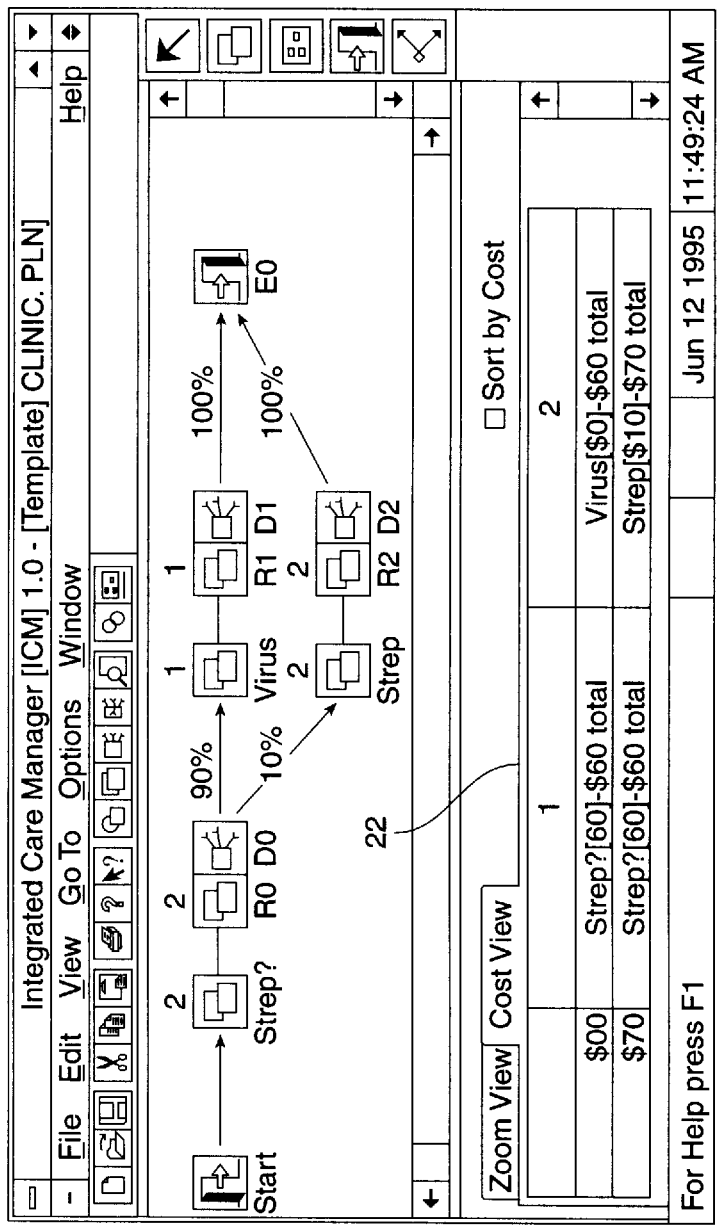
FIG. 2 illustrates an example of a Cost view according to the present invention.

FIG. 2 illustrates an example of a Cost view 22. The Cost view 22 illustrates the cost associated with a medical healthcare template. The Cost view helps a user analyze the cost of treatment specified by a template. Cost view 22 also shows every possible path through the template and lists the cost of each path. Each row in the table of cost view 22 represents a single path through the template. The left most cell of each row contains the cost of that entire path. The remaining columns in the row represent the order nodes in the path. Each order node is listed with its associated cost and the current accumulated cost.

FIG. 3 illustrates an example of Chart view 30. Each step is represented by two columns. The first column represents order items in the node and the second column represents results status of the order. In each order node, there may be multiple order items or multiple instructions or directions in treatment. Therefore, there are multiple rows per column. An order item may also include healthcare business orders, such as verifying the insurance of a patient. In this view, healthcare providers are able to input data at various stages of a healthcare template or plan using the results columns. In addition, healthcare planners and providers can see which treatment steps have been completed by review of the color of the columns—grey as completed, white as active. The Charting view 30 is used to input data and track patient progress view according to the patient plan. Flow Chart view 31 corresponds to the patient chart view. In Flow Chart view 31, it is the same window in which a user builds templates, except the flow is now "active." In other words, a user can start the flow, enter order result into the various nodes, and move through the flow as the treatment progresses using the Flow Chart view instead of the Chart view if a user desires. Color-coding on the nodes show which ones are completed and which are in progress.

Figure 4:
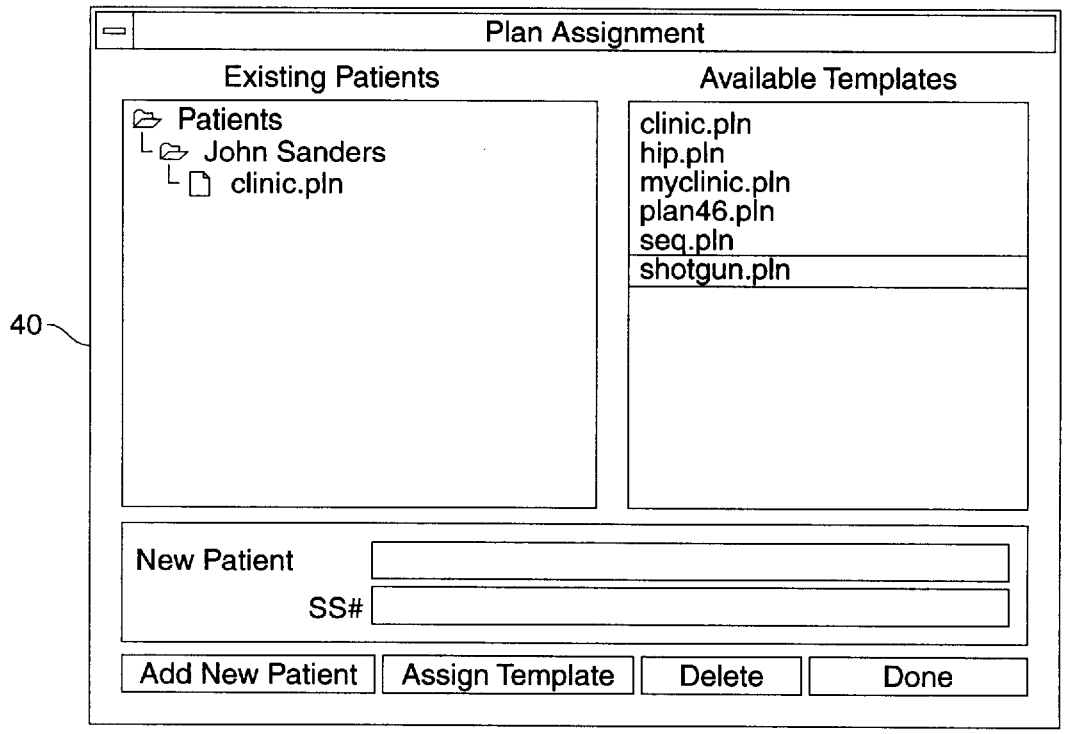
FIG. 4 illustrates an example of a Plan Assignment window according to the present invention.

FIG. 4 illustrates an example of a Plan Assignment window 40. In this window, a completed template can be assigned to a patient. This step merges a template with a patient's plan and enables a care provider to carry out the patient's healthcare plan, which may include various templates. FIG. 4 illustrates the templates assigned to the patient "John Sanders."

Figure 5:
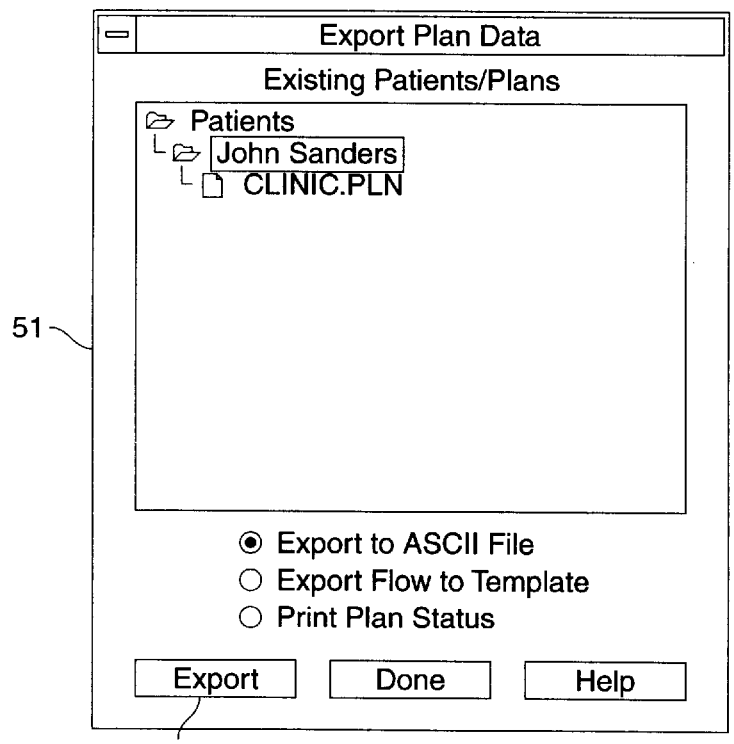
FIG. 5 illustrates an example of an Export window according to the present invention.

FIG. 5 illustrates an example of an Export window 51. The present invention allows for patient plans to be converted into generic templates or exported to other software tools for analysis. A user can export patients' plans in a specific format, or American Standard Code for Information Interchange ("ASCII") by using Export Button 50.

II. BUILDING TEMPLATES

A. Creating a Medical Treatment Template

Before a user can create a template, treatment work flow must be defined; that is, the order in which treatment activities are carried out for a given condition.

A template is constructed from graphic elements or building blocks called "nodes." There are five kinds of nodes: Start, Order, Results, Flow Control, and Exit. Every template has a Start node, which indicates the start of the template. Likewise, every template has at least one Exit node, which indicates the end of the template. Between the Start and Exit nodes are a series of Order, Results, and Flow Control nodes.

Order nodes contain generalized orders placed during the course of a treatment. The Order node defines a list of generalized orders or healthcare treatment related activities "order items" that are carried out at a given step in the template. Order descriptions may be placed into Order nodes from a library. Each order is described using attributes that include category, subcategory, name, description, cost, and duration.

The Result node shows the status of the orders in the corresponding Order node. During patient charting, order results are entered to the Result node. Result nodes contain order status (i.e., an order was done or not done) and result values (i.e., electrolyte measurements).

Flow Control nodes contain rules that govern the branching among nodes in the template. The Flow Control node contains rules that select a branch at a decision point in a template or plan, and estimates of the likelihood of branching down given paths. During patient charting, the Flow Control node suggests the next step to the healthcare provider based on the rules and the results entered in Result nodes. A typical rule in a Flow Control node looks like this:

If(Re1:CBC:Hct:Val<=25)GOTO Transfusion at 5%.

When building a template, nodes are positioned in the chronological order in which they are to be carried out or executed. A user defines each node and connects the nodes.

Template creation involves the following activities: (1) placing Order, Results, and Flow Control nodes in their proper sequence; (2) filling in the orders (i.e., treatment procedures, medicine, and advice); (3) placing an Exit node at the end of the template; (4) deciding on the circumstances and order in which each template step is executed during treatment; and (5) saving the template.

Figure 6:
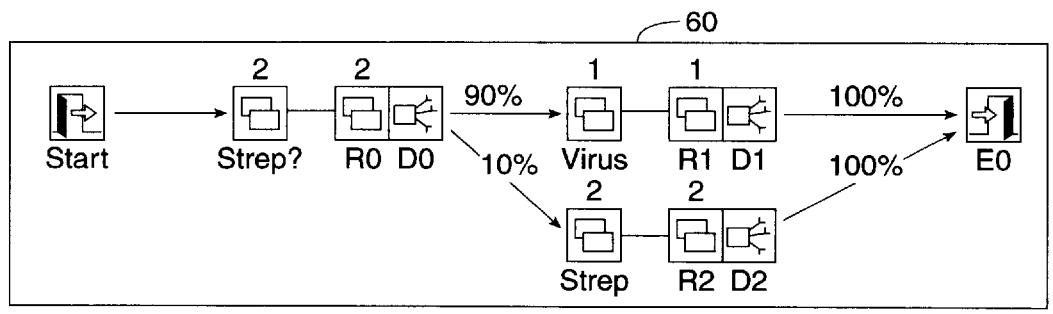
FIG. 6 illustrates the clinical template according to the present invention.

Thus, when a physician prescribes treatment for a condition addressed in an existing template, a stored treatment template can be used instead of creating a new one. If a treatment template does not exist for a given condition, a physician may retrieve a template from the library that addresses a similar condition, modify the template as needed, and start the patient treatment using the modified template B. Clinical Template Example In this example, a simple template called the Clinic Template 60, as shown in FIG. 6, is built to treat a patient complaining of a sore throat. FIG. 6 illustrates graphically a medical healthcare template to treat a sore throat condition in a Flow Chart view. A simplified work flow for a sore throat condition can be represented below:

On the first visit with the patient, a healthcare provider gathers routine vital statistics (i.e., temperature, weight, etc.) and takes a throat culture. A strep test is ordered from the lab. If the result of the strep test is negative, go to the second step and treat the patient assuming the sore throat is from a virus. If the result of the step test is positive, go to third step and treat the patient for strep throat.

If the strep test was negative, give the patient self treatment instructions for a viral infection. Exit the work flow.

If the strep test was positive, give the patient a prescription for penicillin and self treatment instructions for strep throat. Exit the work flow.

1. Creating a New Template

Using the sore throat work flow protocol above, a healthcare planner can develop the Clinic Template 60, a generic treatment template for a patient who has a sore throat. The template may be used by any physician or healthcare provider when determining whether a sore throat is due to a virus or strep.

Figure 7:
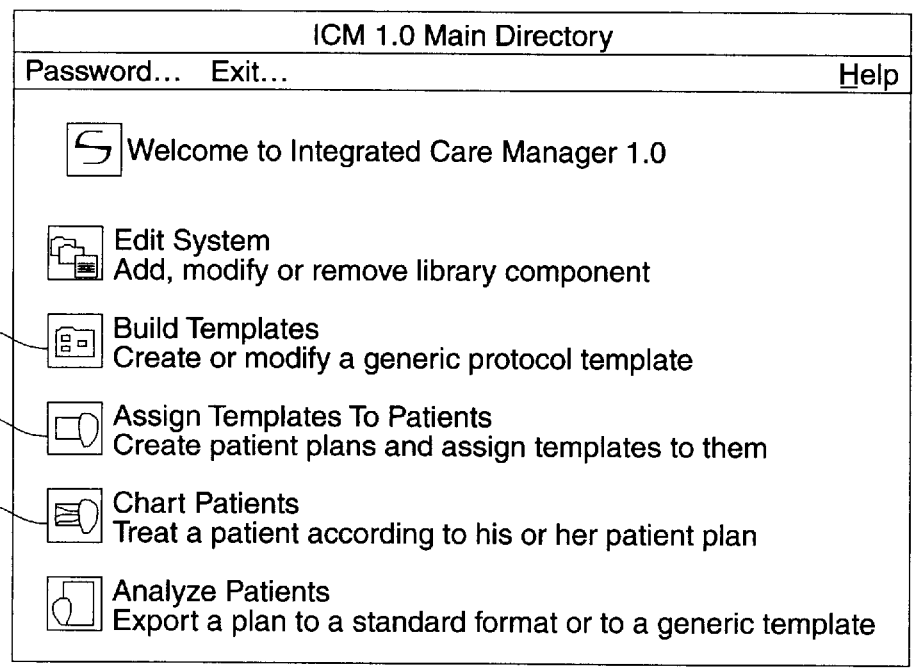
FIG. 7 illustrates the main directory according to the present invention.
Figure 8:
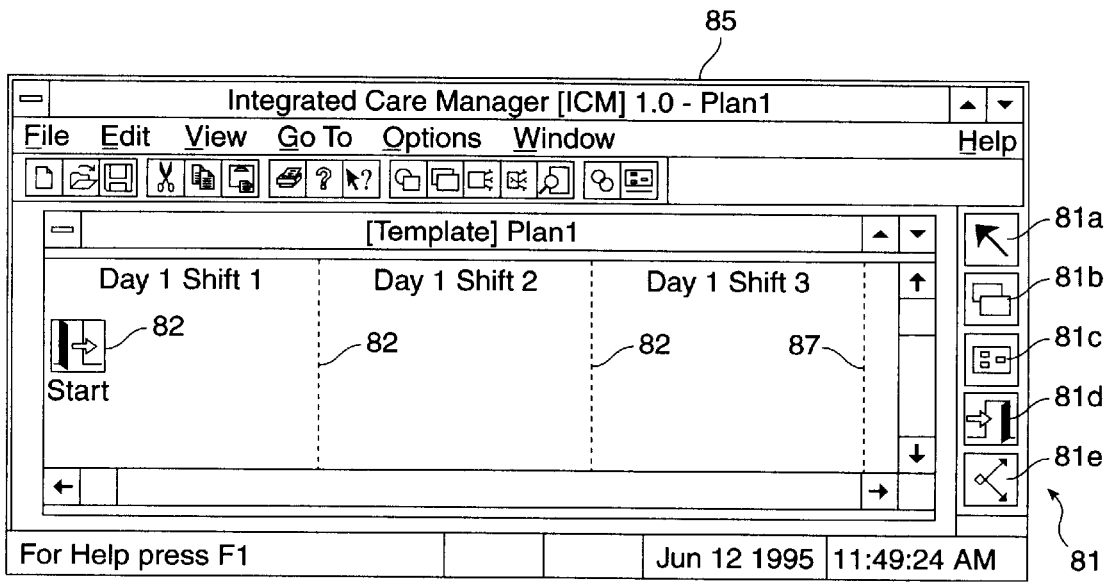
FIG. 8 illustrates the Template Builder window according to the present invention.

Building a Clinical Template 60, as shown in FIG. 6, is initiated by clicking the Build Templates button 70 on the Main Director 71, as shown in FIG. 7. The ARAXSYS™ Solution Main window 85 appears in Template Builder mode as illustrated in FIG. 8. In this mode a user builds, reviews and modifies generic health templates. In an embodiment, a new template automatically contains a Start node 80.

A toolbox 81 is located on the right hand border of window 85. Toolbox 81 contains five tools, each represented by an icon, that aid in building templates. The five tools are Selection 81a, Generalized Order Triplet 81b, Plan Node 81c, Exit Node 81d and Connection 81c.

The Template window is divided into columns by dotted, vertical lines 82. These lines divide the template into time intervals that advance in time from left to right. Headings at the top of each column label each time slot. By default, the time slots are labeled by "day/shift," but there are a variety of other time slot labels that may be selected. The width of the time slots is also adjustable.

2. Placing Order, Results, and Flow Control Nodes (Triplets)

Figure 9:
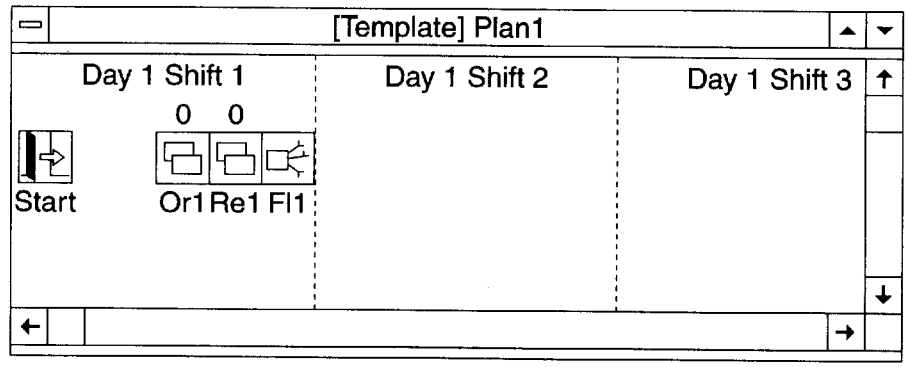
FIG. 9 illustrates the Template with a Start node and an Order Triplet according to the present invention.

FIG. 9 illustrates adding an Order node Or1, Result node Re1 and Flow Control node Fl1 to a template. The Order node Or1 contains the physician's orders, such as lab tests, nursing procedures, x-rays, prescriptions, and other kinds of treatments or actions These generalized orders may be taken from a library and placed in Order node Or1. The Order node Or1 groups all of the orders for a given step in the template.

An Order triplet is entered by clicking the Order tool 81b in toolbox 81. The cursor turns into the icon shape. By moving the cursor to the right of the Start node and clicking once, an Order triplet is placed into the template. A series of three nodes appears. Every Order node Or1 automatically has one Result node Re1 and one Flow Control node Fl1 attached to it; therefore, whenever a user places an Order node from the toolbox, a triplet is actually selected and positioned.

Figure 10:
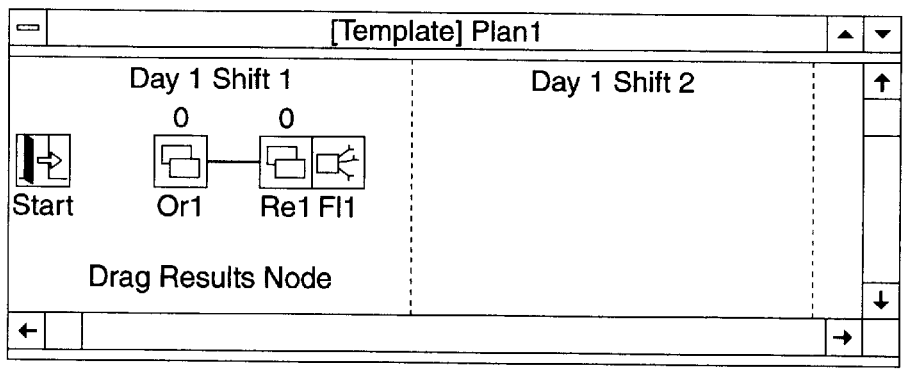
FIG. 10 illustrates separating the Order node from its associated nodes according to the present invention.

In an embodiment, order node Or1 may be separated from Result node Re1 by clicking and dragging the Result node Re1 to the right to set it off from Order node Or1, as shown in FIG. 10. Another embodiment allows a user to choose the time scale setting from the Options menu 86 and increase the size of the number of units per slot unit from 5 to 7. This will increase the space between the time slot separators (the dotted lines 82). The chronological order of a template may be either in real time or virtual time. Real time is the current active time of a triplet or plan and active virtual time is a time set by the user.

3. Naming a Node

To make it easier to follow the template, a user may assign a name to each node in place of its default. For example, the default name for the first Order node Or1 is "Or1", but that doesn't tell a user much about the procedures within that node. Since the first step in the Clinic Template determines whether or not the patient has Strep throat, a user may assign the name "Strep?" to Order node Or1 by:

a. Click Order node Or1 to select it.

b. Choose Name from the Edit button 119.

c. In the Order Node Detail dialog box, type Strep? in Name field.

d. Click OK button 113.

The word "Strep?" now appears under Order node Or1. Next, a user may place orders in the Order node.

4. Placing an Order

Figure 11:
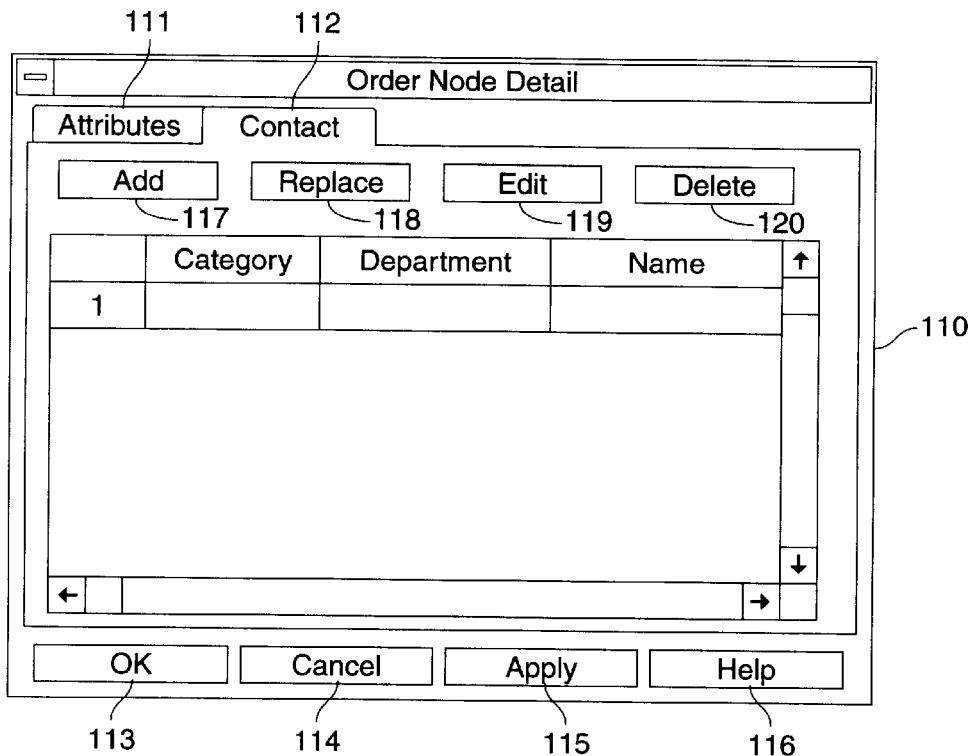
FIG. 11 illustrates the Order Node Detail dialog box according to the present invention.

FIG. 11 illustrates the Order Node Detail dialog box 110 according to the present invention.

By double-clicking Order node Or1 in the triplet shown in FIGS. 9 or 10. The Order Node Detail dialog box 110 appears showing the list of orders (i.e., content) in Order node Or1. There are no orders shown in FIG. 11 in the Order node.

The top of this dialog box 110 contains two "tabs"; Attributes 111 and Content 112.

The following lower buttons have the associated action:

OK button 113 saves changes made in this dialog box when clicking.

Cancel button 114 closes dialog box 110 without taking any action when clicking.

Apply button 115 currently remains disabled.

Help button 116 displays Help for dialog box 110 when clicking.

The upper buttons at the top give a user four choices:

Add button 117 adds an order to be carried out when this template is executed when clicking.

Replace button 118 replaces the selected order with another work order when clicking.

Edit button 119 edits the detail of the selected order, including the order's result values when clicking.

Delete button 120 deletes the selected order when clicking.

Figure 12:
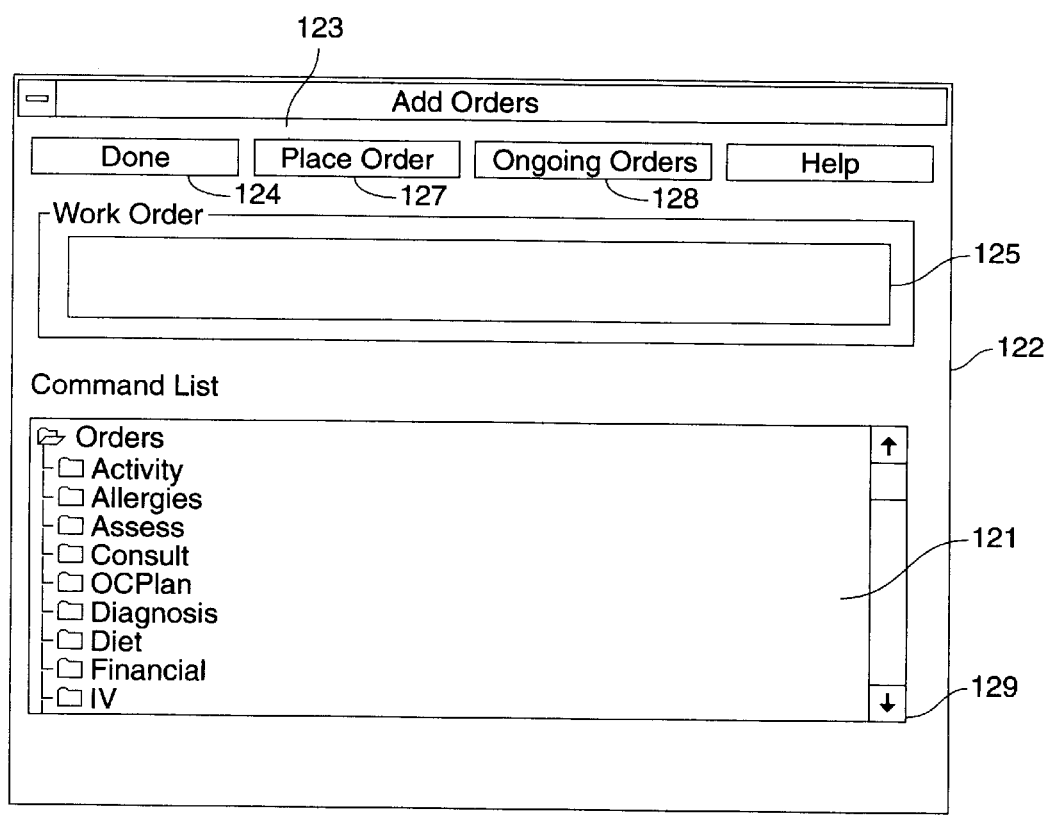
FIG. 12 illustrates the Add Orders dialog box according to the present invention.

FIG. 12 illustrates the Add Orders dialog box 122 when clicking add button 117, shown in FIG. 11, according to the present invention.

All the orders stored in the library appear in the Command List area 121. The work orders in the library are organized by category and department and are displayed as file folders. The Library folder contains category folders, which in turn contain folders identifying the departments that typically carry out the orders. Each department folder contains a series of work orders for the selected category and department.

In the first step of the Clinic Template, two work orders are specified: a strep throat culture, and the routine nursing vital statistics. These work orders are added to the Order node Or1 by the following steps:

a. Use the up/down arrow keys 129 to scroll through the list, and double-click the Labs folder in the Command list to open it.

b. Double-click the Bacteriology folder, and then click Strep ($40.00) to pick the strep test. This work order appears in the Work Order area 125 at the top of this dialog box.

c. Click the Place Order button 127 to add the order to the list of orders in the Orders dialog box.

d. Scroll to the bottom of the Command List, and then double-click on the Vitals folder.

e. Double-click Nursing, and then click Routine ($20.00) as the order to be performed.

f. Click Place Order button 127.

g. Click Done button 124. The Add Orders dialog box 123 goes away. Both of the work orders the user placed are listed in the Orders dialog box 110 as shown in FIG. 13. If the user accidentally placed the same order more than once or placed the wrong order, select the order and click Delete button 120 to remove it.

h. Verity that all of the work orders you selected are listed correctly, and using the buttons across the bottom of the screen, click OK button 113. The Order Node Detail box 110 goes away and a user can see the template.

Thus the contents of the strep? Node shown in FIG. 6 is filled according to the present invention. The number 2 above the strep? node shown in FIG. 6 indicates the number of orders it contains. For every work order, there is a corresponding order result in the Result node Re. Since two work orders have been selected, there are two results in Result node Re.

Next, a user may view the contents of the Result node.

5. Viewing the Result Node Content

The Result Node dialog box 140, as illustrated by FIG. 14, lists the status of orders placed in corresponding Order nodes. Completed work orders show a "Done" status and incomplete work orders show a "Not Done" status. Orders may also show an "Exception" status if the order cannot be filled as expected.

FIG. 14 illustrates the Result Node Detail dialog box 140 according to the present invention. Double-clicking Result node Re1 presents Result Node detail box 140. Clicking content tab 142 displays the content page. All of the orders show a "Not Done" status on the content page because a user is still in the Template Builder mode.

Double clicking the Vitals order 143 in the list of orders, Result Form 150 is displayed, as shown in FIG. 15. This form is where a care provider enters the results of the vitals order when the template is being charted as part of a patient's plan.

When charting a patient, healthcare providers enter results of the vital statistics and set the status to "Done" in Result Form 150. This will mark the entire order as "Done" in the Result Node Detail dialog window 140.

Clicking Cancel button 151 closes the Results Form dialog box 150 and clicking OK button 144 closes the Result Node Detail dialog box 140.

Next, a decision based on the results of the lab work requested in the first Order node Or1 must be made. As for the lab results, there are only two possibilities: either the sore throat is due to a virus or it's due to strep bacteria. So, a user needs to add two more Order nodes: one to hold the work orders if the strep test is negative, and another to hold orders if the strep test is positive.

6. Adding More Order Nodes

To handle these two possibilities, a user adds two more Order triplets, one triplet for each possible branch in the treatment course. A user may name the first triplet "Virus" and the second one "Strep." The Virus node will describe what to do if the patient has a sore throat due to a virus. The Strep node will describe what to do if the patient has strep throat.

Clicking the Order node tool 81c and dragging it to the right of the Fl1 node, and click once positions the Order triplet.

Initially, the Or1 appears beneath the Order node. By default, each triplet a user creates is numbered in consecutive order, starting with the number 1. Since the first Order node Or1 is renamed Strep?, the new Order node is numbered 1 by default. However, since the first Result and Flow Control node are still numbered 1, the second set of Result and Flow Control nodes are assigned the number 2. Order node Or1 may be renamed before assigning work orders to the new Order node.

Or1 node is selected by clicking it.

Name is chosen from an Edit menu or double click Or1 node to show the Order Node Detail dialog box 110 and click the Attribute tab 111 as above.

In the Node Attribute dialog box that appears, type Virus in the Name box and click OK button 113. The word "Virus" now appears in place of Or1. The Result node must be dragged over a bit to separate it from the Order node, as shown in FIG. 16.

An additional triplet may be added by the above steps. However, this time, the triplet would be positioned below the Virus triplet and the new Order node would be named "Strep", as shown in FIG. 17.

Work orders to the Virus and Strep Order nodes then must be assigned. One work order will be assigned to the Virus node and two work orders to the Strep node.

7. Assigning Work Orders to Nodes

To assign work orders for the Virus node:

a. Double-click the Virus node.

b. Click Add button 117 in the Orders node detail dialog box 110. Patients with sore throats caused by a virus are to be discharged with a discharge direction sheet.

c. Double-click the DCPlan folder in the Command list in add orders dialog box 122 shown in FIG. 12. Discharge direction sheets are grouped by department.

d. Double-click the Clinic folder, and then double-click DC_Instructions_for_Virus ($0.00) to select the work to be performed.

e. Click Place Order button 127 to add the order to the list in the Orders dialog box.

f. Click Done button 124. The Add Orders dialog box 122 goes away.

g. Verify that only the work order the user selected is listed, and then click OK button 113. The Orders dialog box 110 goes away.

Figure 18:
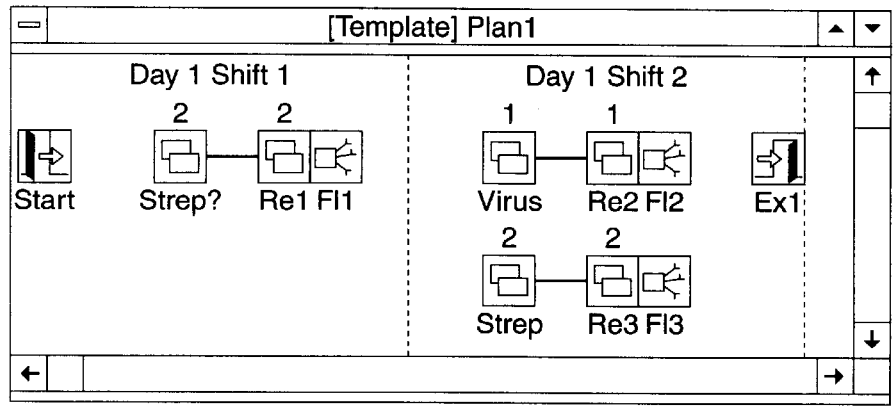
FIG. 18 illustrates adding an Exit node according to the present invention.

A "1" appears above this second triplet, as shown in FIG. 18, indicating one work order is assigned.

To assign work orders for the Strep node:

a. Double-click the Strep node.

b. Click Add button 117 in the Orders dialog box 110. Patients with sore throats caused by the strep bacteria are treated with two work orders: DCPlan Clinic and a ten-day dose of penicillin.

c. Double-click the DCPlan folder in the Command list in Add Orders dialog box 122 to open it.

d. Double-click the Clinic folder, and then double-click DC_Instructions_for_Bacteria ($0.00) to select this work order.

e. Click Place Order button 127 to add the order to the list in the Orders dialog box.

f. Double-click the Meds folder in the library list.

g. Double-click the Pharmacy folder, and then double-click PO_Penicillin_($10.00) to select this drug.

h. Click Place Order button 127 to prescribe the drug and add it to the list in the Order node detail dialog box 110.

i. Click Done button 124.

j. Verify that only the work orders you selected are listed, and then click OK button 113.

A "2" appears above this triplet, as shown in FIG. 18, indicating two work orders are assigned. A template containing a Start node and three triplets having orders, treatment results, and flow control has been developed. The last node to add to the template is the Exit node Ex1. The Exit node simply marks the end of the template, like the Start node.

8. Adding an Exit Node

An Exit node Ex1 is positioned by clicking the Exit node toolbox 81c, selecting and placing it to the right of the other nodes, as shown in FIG. 18.

Now that nodes are in place, connections between them must be made. A connection tool 81e in toolbox 81 is used to specify the flow between the different sets of orders.

9. Connecting the Nodes in the Template

The Flow Control node contains the rules that determine which set of orders are followed. Flow Control nodes are connected to one or more Order nodes. However, only one of the Order nodes will be executed.

First, the Start node is linked to the Strep? node. This connection indicates the node to execute first. The first Flow Control node Fl1 is linked to both the Virus and Strep Order nodes. Doing so indicates that a decision will be made based on the results of an order filled in the first Order node.

a. Click the Connection node tool 81e in toolbox 81 to select it. The pointer turns into a large arrow pointing up.

b. Click once on the Start node, and then once on the Strep? node. An arrow appears between the two, indicating the order of the work flow. The Connection tool remains selected until a user selects another tool. So, a user can go ahead and make the other connections.

c. Click the Fl1 node and then click the Virus node.

d. Click the Fl1 node and then click the Strep node.

e. Click the Fl2 node and then click the Exit node.

f. Click the Fl3 node and then click the Exit node.

g. Unselect the Connection tool by either clicking the Connection tool again or by selecting any other tool.

Figure 19:
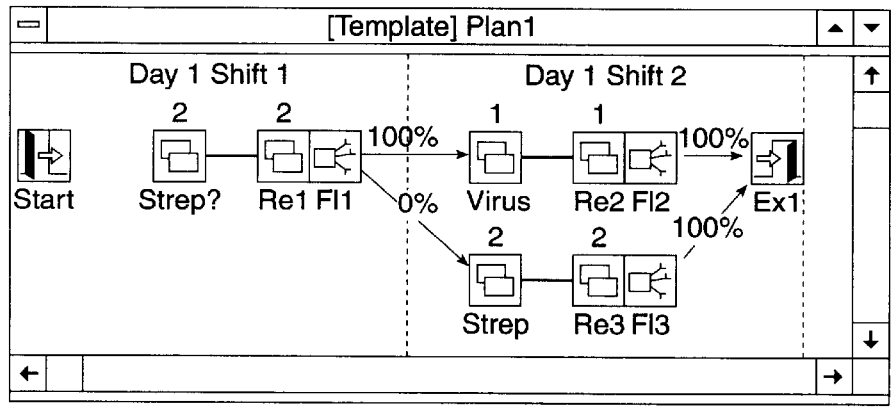
FIG. 19 illustrates the connections between the nodes according to the present invention.

The template having the connections is shown in FIG. 19.

After making these connections or links, Flow Control node Fl1 must be edited to include the rules that govern the branch taken during patient charting.

10. Connections

As seen above, connections indicate relationships between nodes in a template. There are three types of connections: Order Results, Process Flow and Information Flow. Each type of connection is represented differently to help a user understand the relationship it represents.

a. Order Results

Figure 19A:
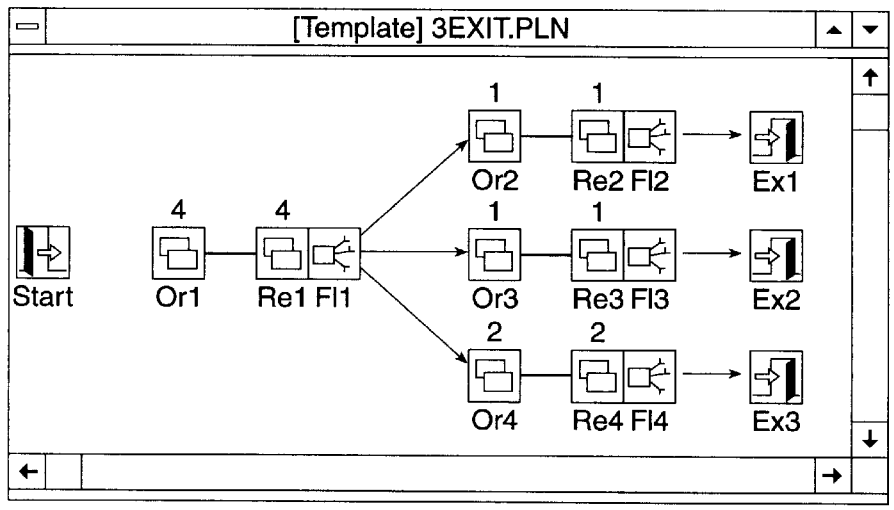
FIGS. 19a–19c illustrate various types of connections according to the present invention.

These connections are illustrated with double lines and indicate the relationship between orders and their corresponding results. FIG. 19a shows an order node with four lab test orders. One of the orders in not available until some time later. The Order Results connections show which Result Nodes hold the results of the orders placed in a given Order node.

Figure 19B:
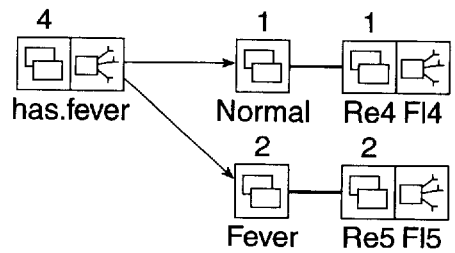

As seen in FIG. 19b, whenever a triplet is placed into a template, the Order Node is automatically given one of these connections to the Result node. As with all connections, when nodes are moved around the template, the connections remain intact.

b. Process Flow

Process Flow connections are created using the Connection tool 81c from Toolbox 81 described above.

c. Information Flow

Figure 19C:
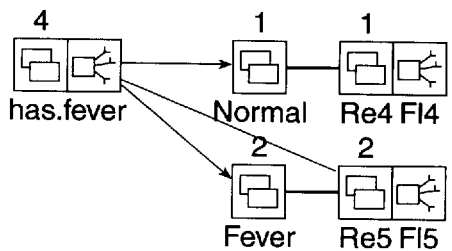

These connections make order results from one triplet available to the rules in another triplet. They are illustrates in a template with a single line between a Result node in one triplet and a Flow Control node in another triplet, as seen in FIG. 19c.

The connection is created using the Connection tool the same way Process Flow connections are created. A user creates these connections when a rule needs to reference the results of an order completed in a previous step in the plan. The example in FIG. 19c shows an Information Flow from the Result node in the "has.fever?" triplet to the Flow Control node in the "Fever" triplet.

11. Programming the Flow Control Nodes

Figure 20:
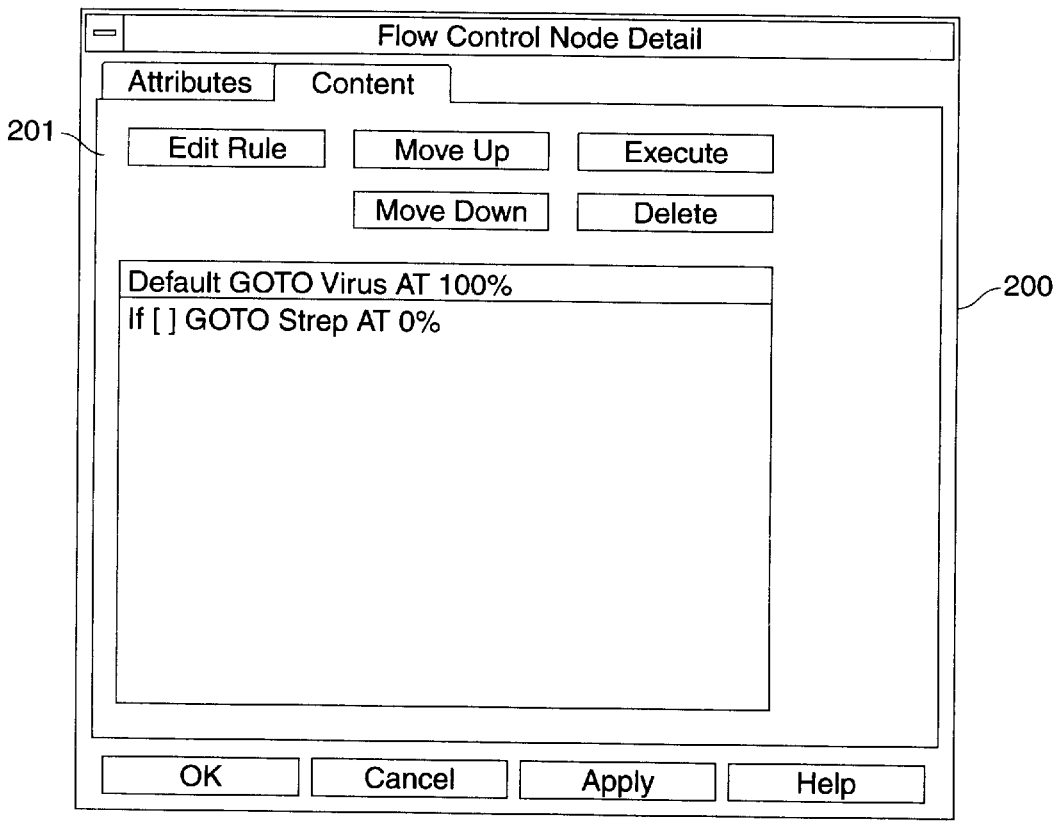
FIG. 20 illustrates the Flow Control Node dialog box according to the present invention.
Figure 21:
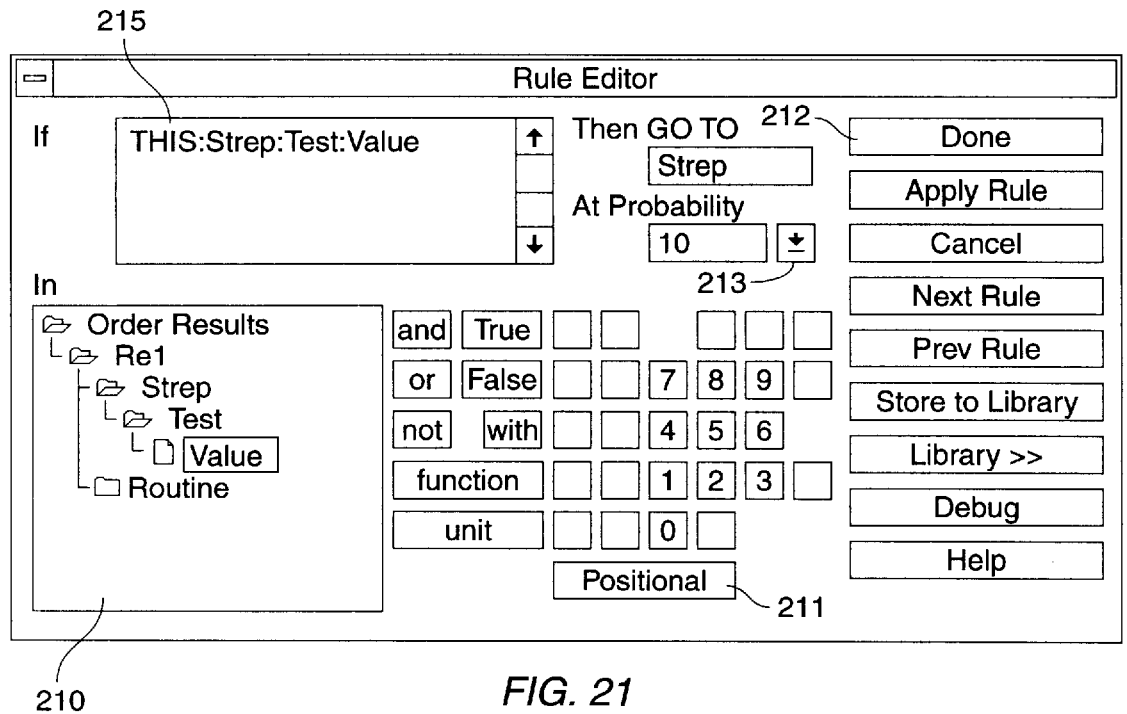
FIG. 21 illustrates how to add the rule using the Rule Editor dialog box according to the present invention.
Figure 22:
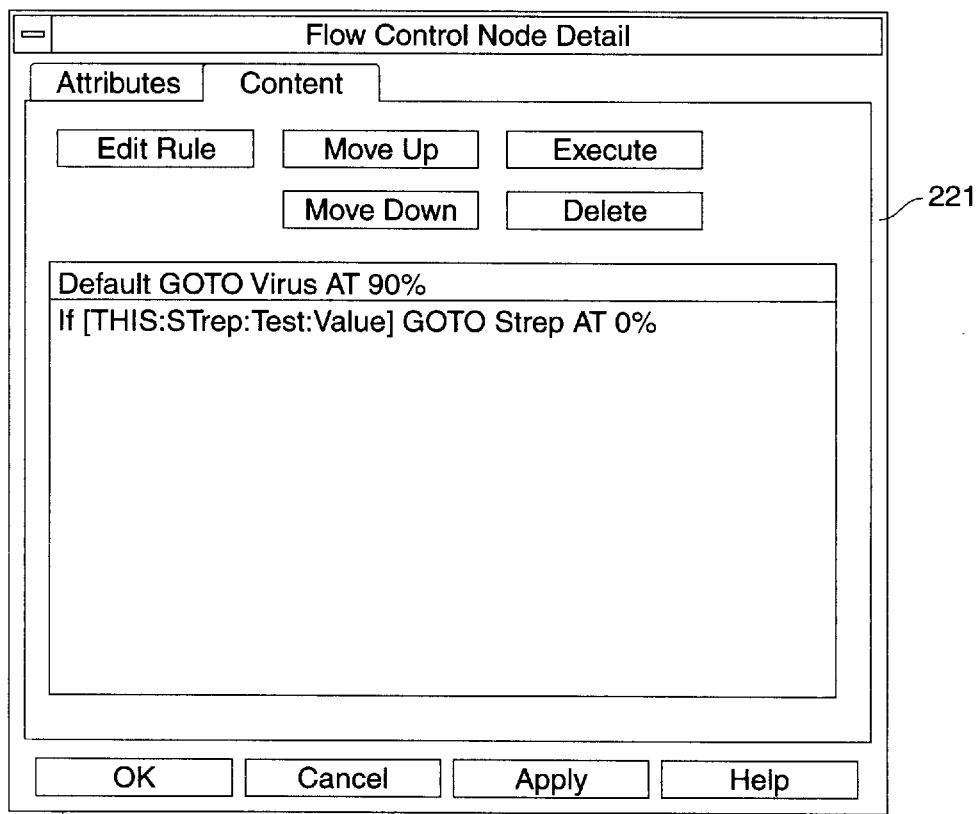
FIG. 22 illustrates a completed rule according to the present invention.

A Flow Control node may be connected to two or more Order nodes, but only one of those Order nodes will be executed. Each Flow Control node contains a set of rules that determine which Order nodes will be executed in the next step of the template. A user defines the rules by creating simple expressions that reference the results of completed orders or other variables available in the template.

a. Double-click the flow control node Fl1. The Flow Control Node dialog box 200 appears, as shown in FIG. 20, listing two rules. Each branch in the template is associated with a rule. The rule indicates the Order node executed when the rule is satisfied and the branch is taken. The first rule in the list is the default rule. It is taken when all of the order results are available and no other rule is satisfied. In this example, the default branch leads to the Virus node. The orders in the Virus node are placed if the second rule is not satisfied. If the second rule is satisfied, the orders in the Strep node are placed.

b. Click the second rule (If ( ) GOTO Strep . . . ) in the Flow Control Node dialog box 200, to select the second rule. Since the rule for the Virus branch (the default) is satisfied only if the rule for the Strep branch is not, the second rule is edited first. This rule is edited using the Rule Editor dialog box 210 shown in FIG. 21.

c. Click Edit Rule 201, as shown in FIG. 20, to edit the contents of the currently selected rule. In general, rules contain expressions that reference the results of orders. The file folder tree in the lower left corner of the Rule Editor dialog box 210 contains all of the order result values that this Flow Control node can reference. The result of the expression must be a logic value, i.e., TRUE or FALSE (or positive and negative).

d. Double-click the Re1 folder in the Rule Editor dialog box 210. Then double-click the Strep folder, the Test folder, and Value. A second rule has now been created. It appears in the scroll box 215 next to the word "If". A user can read the files as follows: "If the result of the Strep test value is positive (meaning the result is positive) then follow the procedures in the Strep Order node." Since there are no other branches, a user can also read in the following: "Otherwise, follow the procedures in the Virus Order node." Notice that Result node name, "Re1" in this case, is replaced with the keyword "THIS." The keyword "THIS" indicates the rule references the results of an order in this triplet. A user can manually replace "THIS" with "Re1" if a user wants to limit the rule to reference only the results in a node named "Re1". If a user leaves it referencing "THIS", the rule can be copied into the library and used in another template without change. The result is the same during patient charting whether the reference is prefixed by "THIS" or "Re1." However, if a user wants the rule to reference results of an order from this node or a previous node in the patient's plan, a user can replace the keyword "THIS" by the keyword "LAST". A user can simply replace the text in the rule editor field, or select "THIS" in the rule editing field, click the "Positional . . ." button 211 on the rule editor, and choose LAST from the list. If the order is not present in this triplet, a rule specifying "LAST" will reference the most recent order results.

e. Next, the probability that the results of the Strep test will be positive must be set. In general, the probability values are set based on experience, studies, or metrics gathered over time. For this example, click the At Probability drop-down arrow button 213 and select 10 as the percentage.

f. Click Done button 212 in the Rule Editor dialog box 210. In the Flow Control Node Detail dialog box 221 shown in FIG. 22, notice that the first rule automatically changed based on the second rule. Since the probability that the Strep test will return a positive result is about 10%, the probability that the sore throat is due to a virus is 90%.

g. Click OK button 220 in the Flow Control Node Detail dialog box 221 to close it.

A user must have enough rules to cover all of the branches out of the Flow Control node. Because every Flow Control node contains a default rule and may contain additional rules, the number of rules is always one less than the number of branches. Thus, if a node has four branches, it must also have three rules. In this example, a user only needs to enter one rule.

Note that even though the default rule is created, a user can still set the default rule. However, because the definition of a default rule is that it will be used when no other rule applies, the rule put in the default rule will not be evaluated as criteria for using the rule as long as it is the default. An option is available to change the rule to a non-default rule. At this point, the rule will be evaluated.

12. Ongoing Order

Figure 22A:
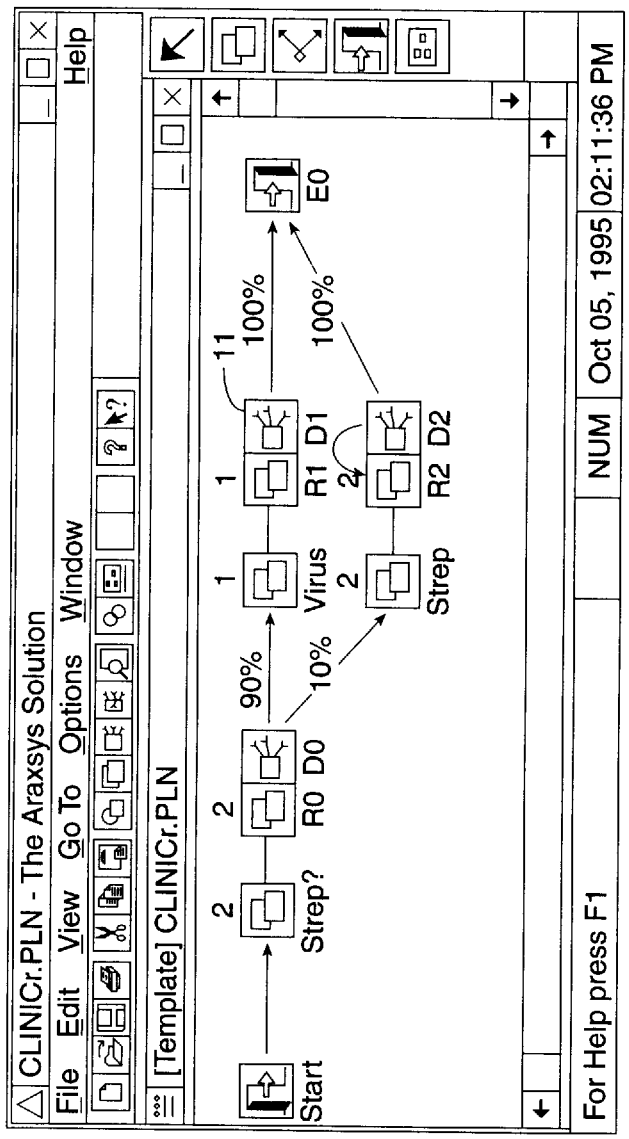
FIG. 22a illustrates an Ongoing order according to the present invention.
Figure 22B:
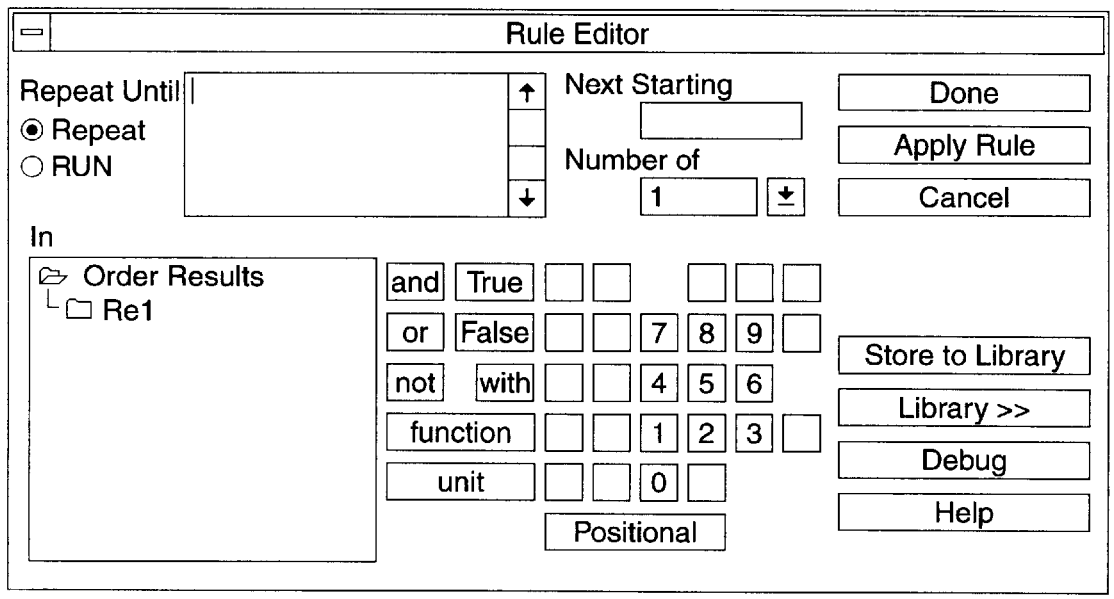
FIG. 22b illustrates an Ongoing order rule editor according to the present invention.

Ongoing orders are orders which are repeated periodically, or run continuously, until certain criteria are met. Ongoing orders may be selected from Ongoing Order button 128 in FIG. 12. An Ongoing Order Strep with result node R2 and Flow Control node D2 is illustrated in FIG. 22a. Edit Order window, a special version of the Rule Editor window is displayed, as illustrated in FIG. 22b. The unique characteristic of this version of the Rule Editor, is the Repeat and Run buttons in the top left-hand corner.

By clicking the Repeat button the order is repeated according to the rules specified in this window.

When the Repeat button is selected, the label above it reads "Repeat Until," and the field labeled "Next Starting" and "Number of" lets a user further define the repeating order. The field labeled "Next Starting" indicates the date to start the next repetition of the order. A date or work shift is entered in this field. The field labeled "Number of" indicates the maximum number of times the order is to be repeated. The option arrow next to the field is clicked to enter a multiple of five, or any number greater than zero may be typed.

The Run button is clicked to indicate the order is to run continuously until the specified rules are met. When the Run button is selected, the label above the Repeat button reads "Run Until," and the "Next Starting"0 and "Number of" fields are replaced with the "With Medicine" and "At Rate (ml/minute)" fields to help a user further define a continuously running order. The field labeled "With Medicine" indicates medication that is to be given in combination with a specified treatment. The field labeled "At Rate (ml/minute)" indicates the speed that the dose of the medicine should be administered. For example, a user can create an ongoing order specifying a base IV solution and indicate the specific medication added in the "With Medicine" field (e.g., Potassium) and a flow rate of 1 ml/minute.

A user specifies the conditions when the Ongoing order is to be discontinued in the scrollable field beside the Repeat and Run buttons. The discontinuation conditions are specified as a logical expression.

Some keys on the right hand side are gray. These keys are not applicable to this window. The rest of the keys are common to all the rule editors.

13. The Plan Node

The Plan node provides a way for users to create a template that branches into another template. The Plan Node acts as a special type of exit node because it causes the current template to exit and the new template to begin.

Figure 23:
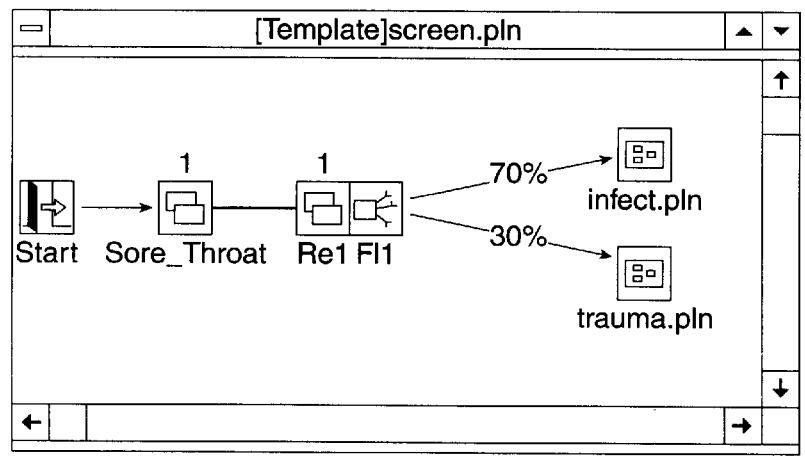
FIG. 23 illustrates a template containing Plan nodes according to the present invention.

FIG. 23 illustrates a template containing Plan nodes according to the present invention. This is an example of a template that might be used by an emergency department screening nurse when a patient comes to the emergency department complaining of a sore throat. The first step in the template in FIG. 23 specifies an assessment of the patient's throat, and any relevant history, to determine whether the patient should be treated for a bacterial or viral throat infection, or throat injury. Based on this decision, the patient is started on one of two templates. Before adding a Plan node to a template, first create the templates behind the Plan nodes. Since each Plan node is a complete template, a user will need to follow the procedure for creating a template to establish the content within each Plan node.

A user can insert a Plan node in the template as a place holder for the template before it is completed. A Plan node may be placed into the template using the Plan node icon in the toolbox with the other node types, for example, order triplets and the exit node.

Figure 24:
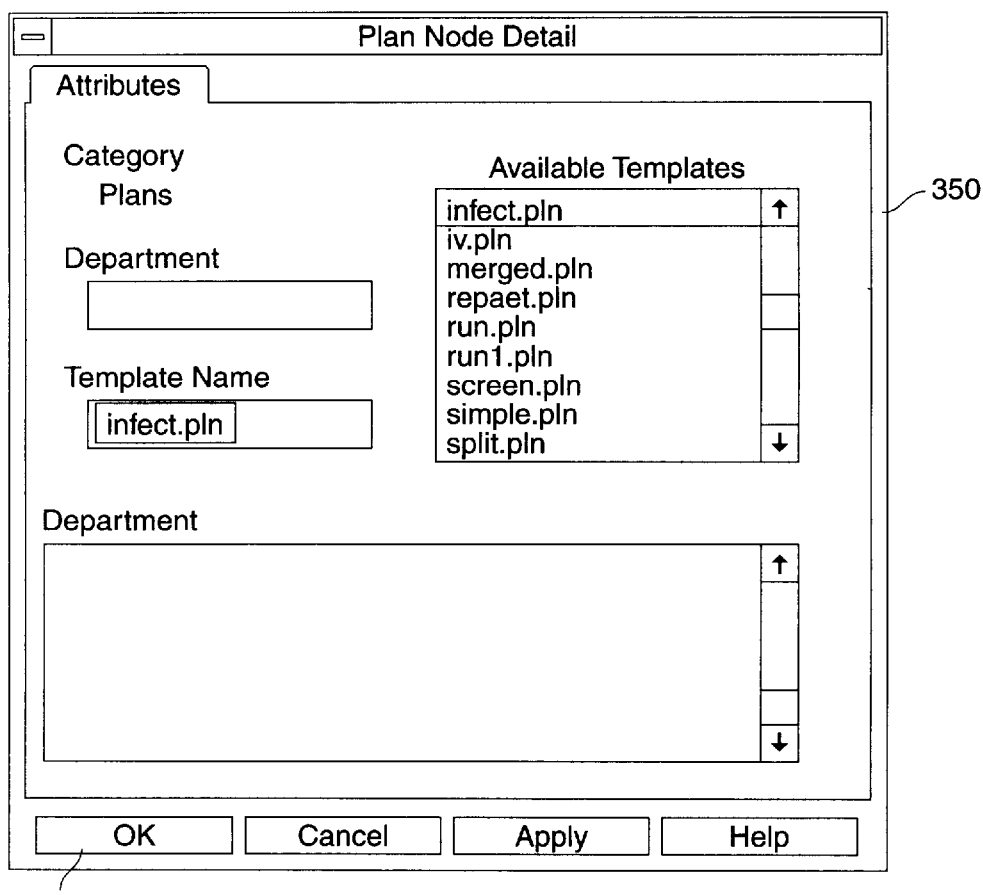
FIG. 24 illustrates a Plan Node Detail dialog box according to the present invention.

Assuming a user has already created a template for a Plan node, the following steps place the Plan node into a new template.

a. Click the Plan node icon in the toolbox, move the cursor to the desired position in the template and click the mouse to place the Plan node into the template.
b. Select the empty Plan node and choose the Name option from the Edit menu. This brings up the Plan Node Detail dialog box 350 as shown in FIG. 24.
c. If the template has been previously created and saved, double click the name of the desired from the list of available templates. This attaches the Plan node to an existing template. A user may enter a description and assign the Plan node to a department.
d. Click OK button 351 to close the dialog box.

At this point, the Plan node is tied to another template. If you double-click on the Plan node, the template is brought up and you may edit it.

14. Saving the Template

To save the template, the Save from the File menu may be chosen using the default name given by ARAXSYS™ Solution. Or the following can be done:

a. Choose Save As from the File menu.
b. A Save As dialog box will pop up for a user to type the name of the template. Make sure the file is in the "data" subdirector in the director where icm.exe is located.
c. Click OK.

C. Building a Template Flow Chart

Figure 25A:
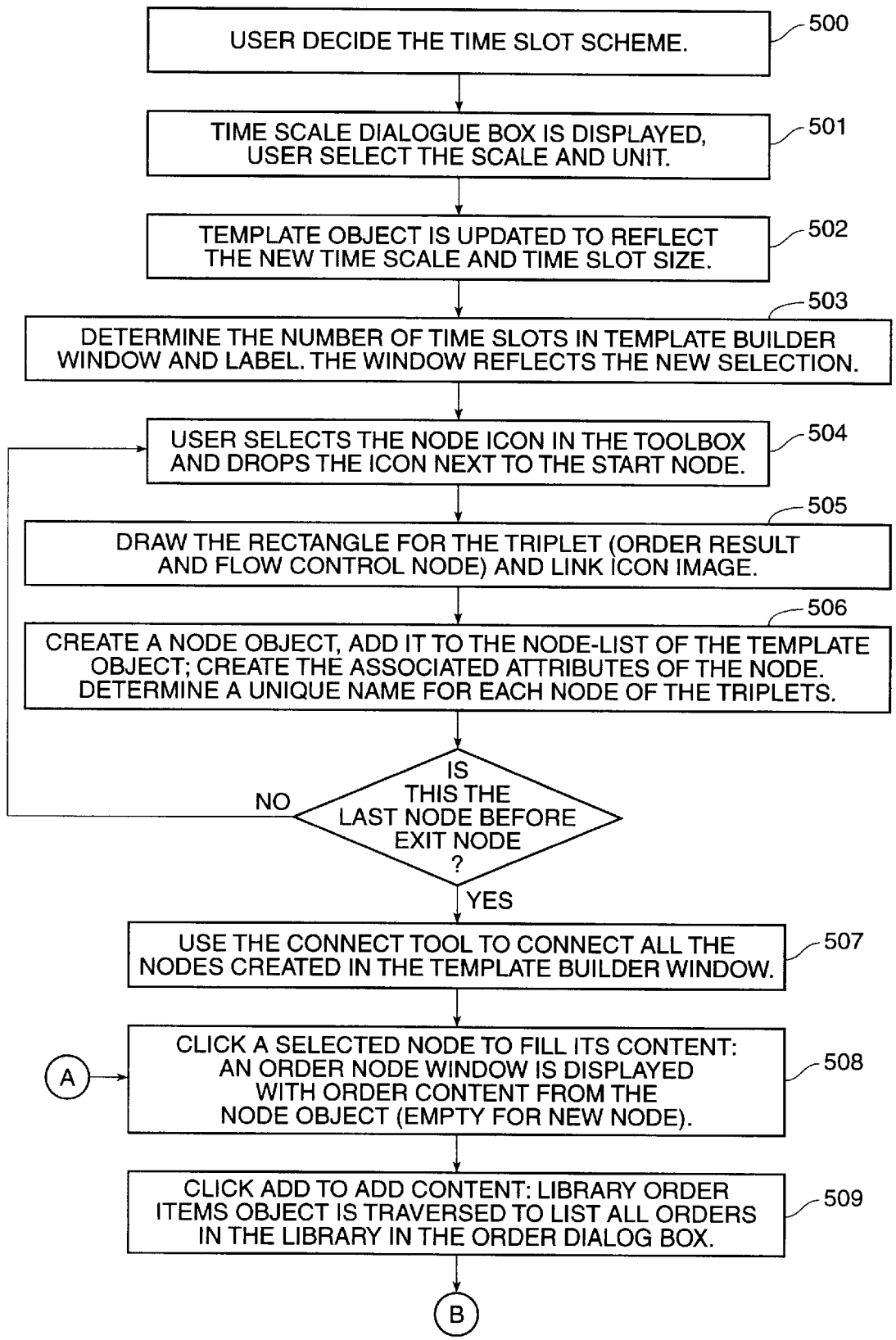
FIGS. 25A–25B illustrate a logic flow diagram of building a template according to the present invention.
Figure 25B:
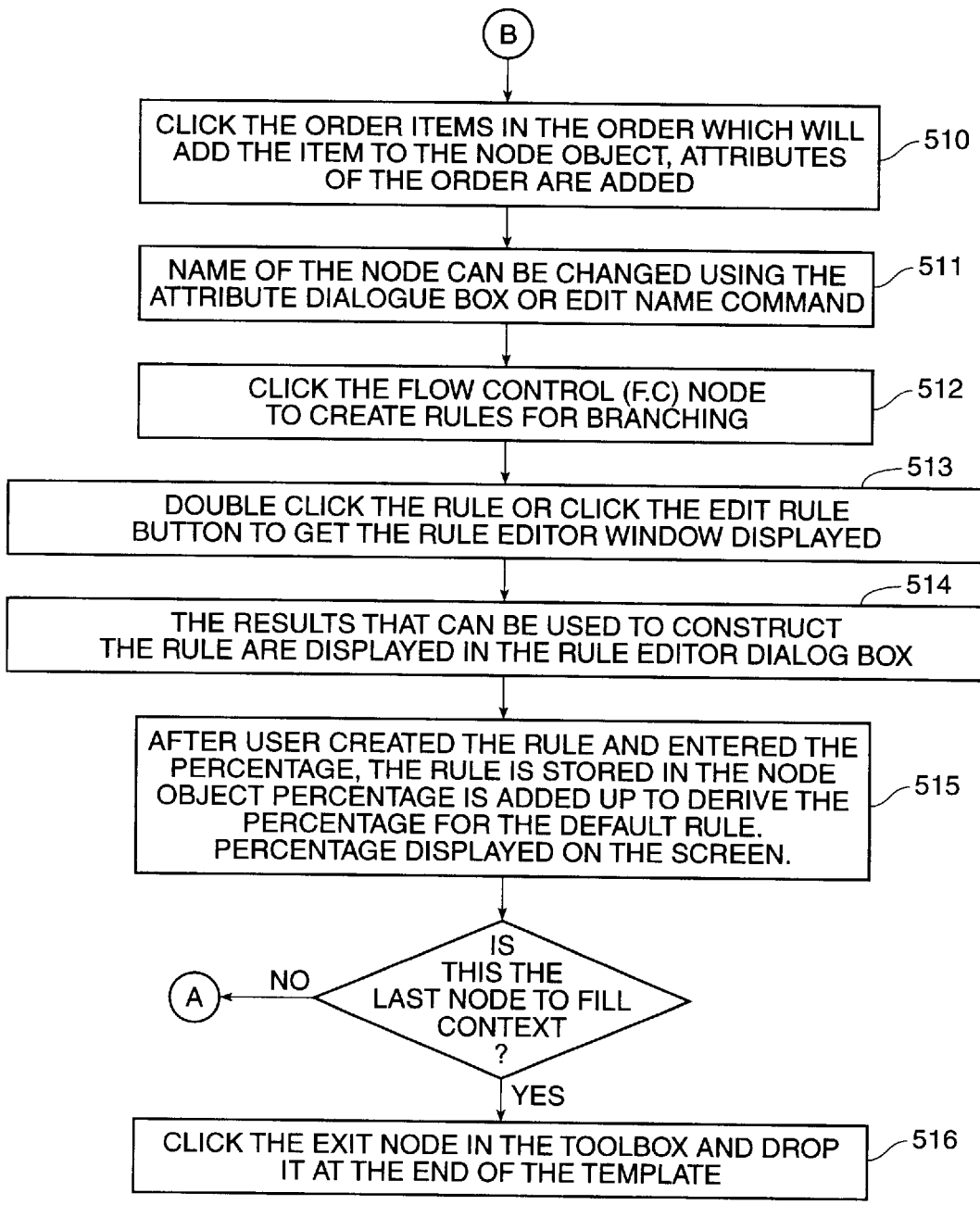

FIGS. 25A–25B illustrate the logic flow in building a template according to the present invention. Objects, methods and attributes described in FIGS. 25A–25B are described in detail below. A user first needs to decide the time slot scheme to be implemented in logic block 500. A time scale dialog box is then displayed, allowing the user to select the scale and unit in logic block 501. The corresponding template object (for example, template object 348 in FIG. 27) is updated to reflect the new time scale and time slot size in logic block 502. Based upon the selected time slot scheme, the number of time slots are determined and labeled in logic block 503. The window reflects the new selection. In logic block 504, a user selects the node icon in the toolbox and drops the icon next to the start node. A triplet is then drawn in logic block 505. In logic block 506, an instance of the node object is created. The node object is then added to the template object list (node_list 371 in FIG. 27). Further, the associated attributes of the node are created and a unique name may be determined for the node of triplets. If this is the last node before the Exit node, the logic flows to logic block 507. Otherwise, a user may select another node in logic block 504. A user connects the nodes in logic block 507. In logic block 508, a node is selected by the user to fill its contents. An Order node window will be displayed with the current order contents from the node object. In the case of a new node, the display will be empty. In logic block 509, the library order item object (for example, order 358 in FIG. 30) is traversed to list all orders in the library in the order content window. In logic 510, a user selects the order items to be added to the node object. Further, attributes of the order are added. With each order, an entry in the result node object (Result node 359 in FIG. 27) is created and the status of the result item is linked to the control node which contains the rule (If Rule 353 in FIG. 27) object via the information flow link list. The name (Name 399 in FIG. 27) of the node may be changed in logic block 511. The uniqueness of the name is verified by comparing all the names in the node list of the triplet object before the change becomes effective in the object and reflected on the screen. A flow control node is selected to create rules for branching in logic block 512. A search for the destination node in info_destination_list which is connected to the flow control node is then carried out. The Flow Control node detail dialog box is then displayed. The flow control rules will be empty, except for the default rule. User will click the rule or the Edit Rule button to display the rule editor dialog box in logic block 513. The contents of the rule editor dialog box is constructed after all the result node objects connected to the flow control nodes are searched in the node_list of the triplet. The results which can be used to contribute to the rule is displayed in the rule editor in logic block 514. In logic 515, the user creates the rule and enters the percentages. The rule is then stored in the (Expr. 354 seen in FIG. 27) object and the percentages are then added to derive the percentage for the default rule. The percentages are then displayed on the screen. If no other nodes need to be filled, the exit node is selected and placed in the template in logic block 516. Otherwise logic block 508 is performed.

D. Costing

Figure 25C:
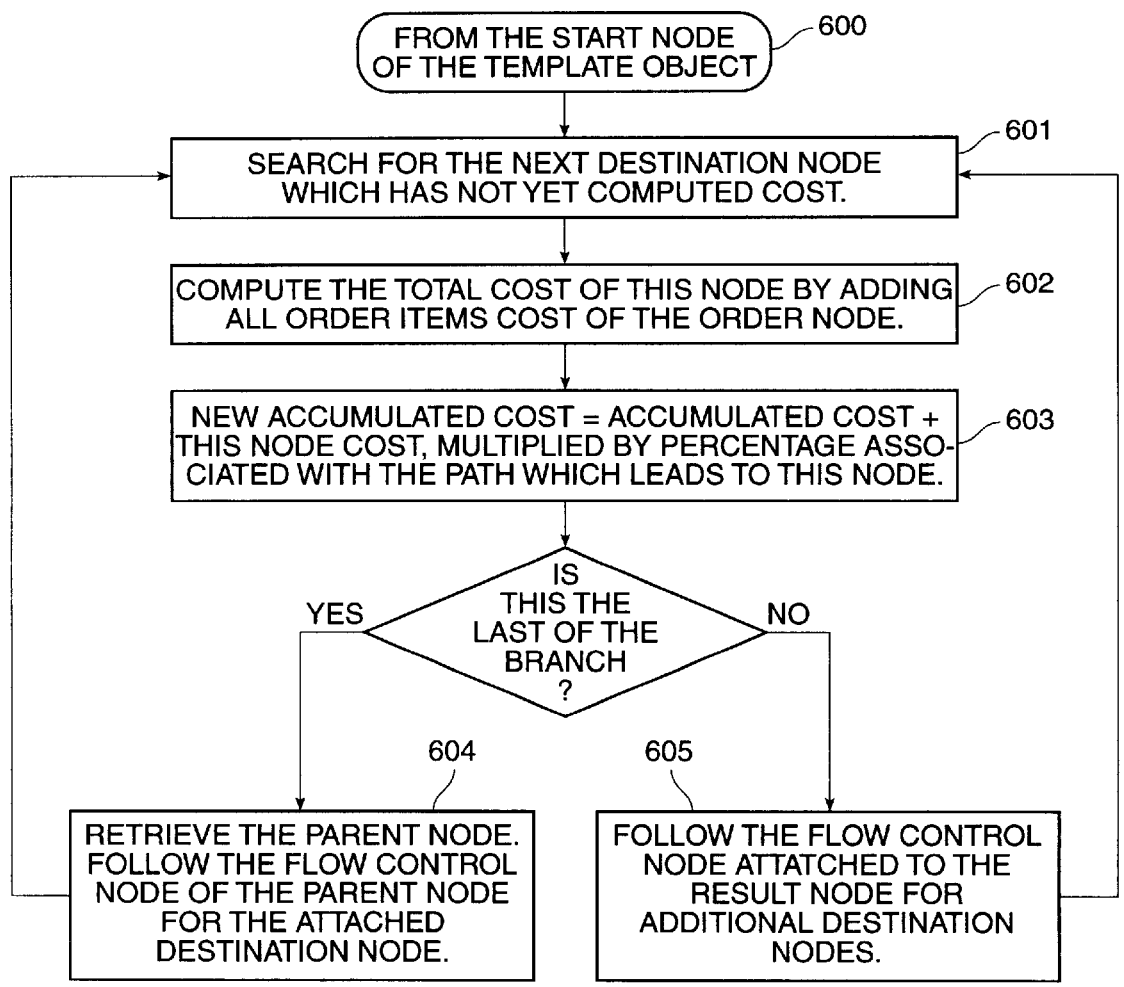
FIG. 25c illustrates a logic flow diagram of determining cost according to the present invention.
Figure 27:
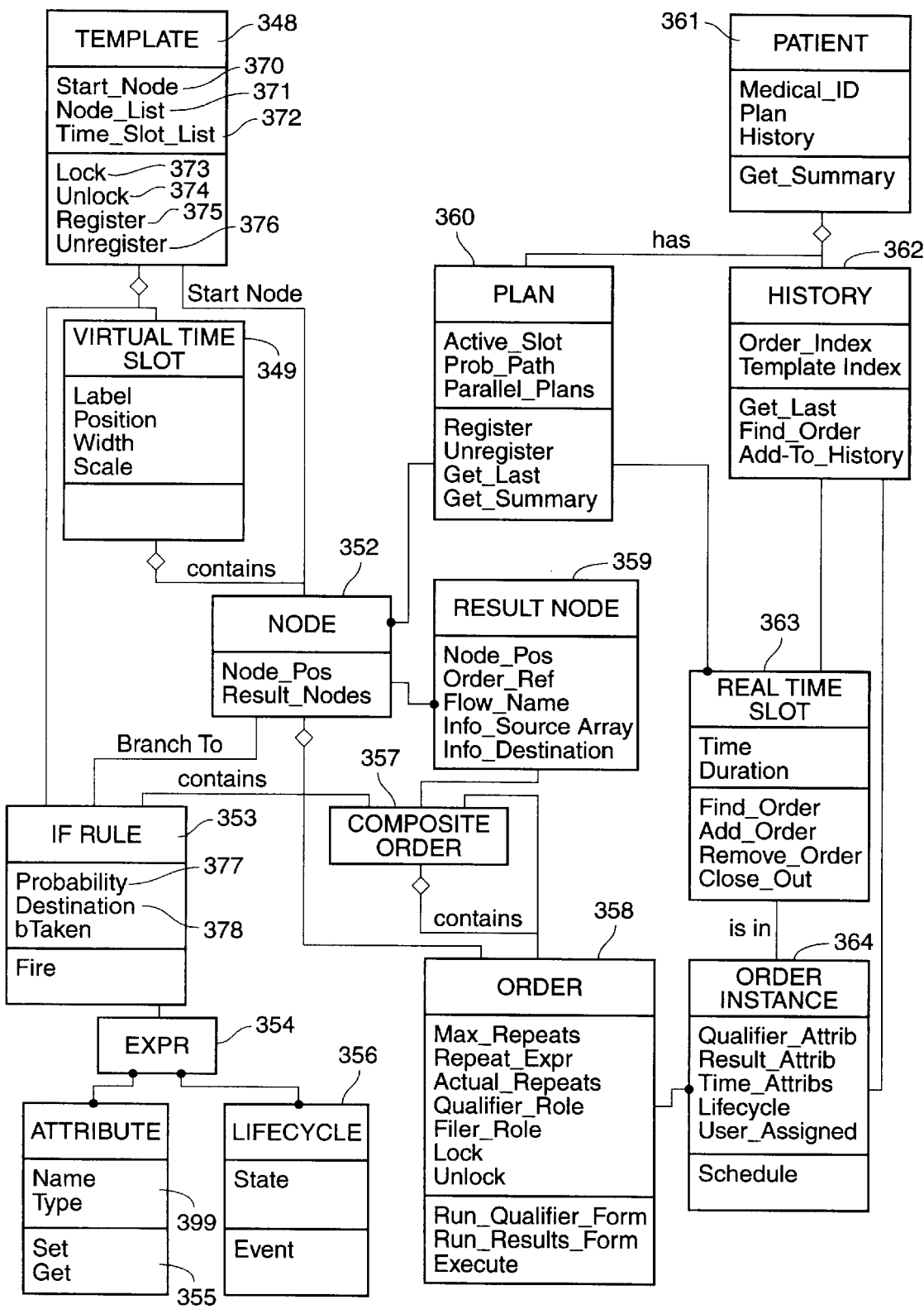
FIG. 27 illustrates the server object relationship according to the present invention.

FIG. 25c illustrates the logic flow of determining the cost of various healthcare treatments according to the present invention. The cost of various treatments is initialized at the Start node in logic 600. A search for the next destination node, which has not yet computed cost, using the node list 371 and info_destination in Result node 359, as seen in FIG. 27, is done in logic block 601. A total cost is determined by adding all item costs of the order node in logic 602. Each order object has an attribute object which contains associated costs for each order item. A running cost (i.e., new accumulated cost) is determined in logic 603 by adding the selected node cost (including all order item costs) which is multiplied by the percentage associated with the path which leads to this node to the current accumulated cost. A determination is then made whether this node is the last node of a path. That is, if there is any destination node of this node. If this node is the last node, the present order node object is retrieved in logic 604, so we can use the same logic to compute the cost of the next path of the present node. Otherwise, the flow control node is followed in logic block 605 in order to determine the cost of the next destination nodes.

III. ASSIGNING A TEMPLATE TO A PATIENT

A template may be assigned to one or more patients. When a template is assigned to a patient, it becomes part of the patient's plan. The patient's plan is a collection of all of the templates that have been assigned and possibly tailored to the specific patient. Once a template is assigned to a patient, the template may be modified or executed.

Figure 31:
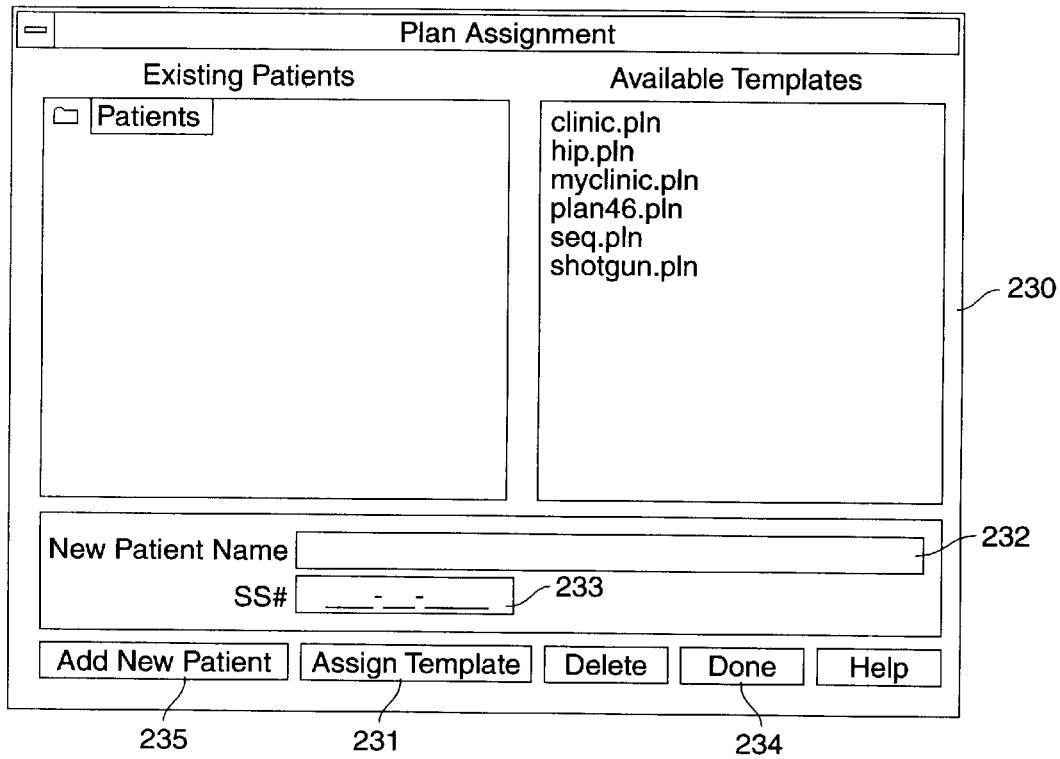
FIG. 31 illustrates the Plan Assignment dialog box according to the present invention.
Figure 32:
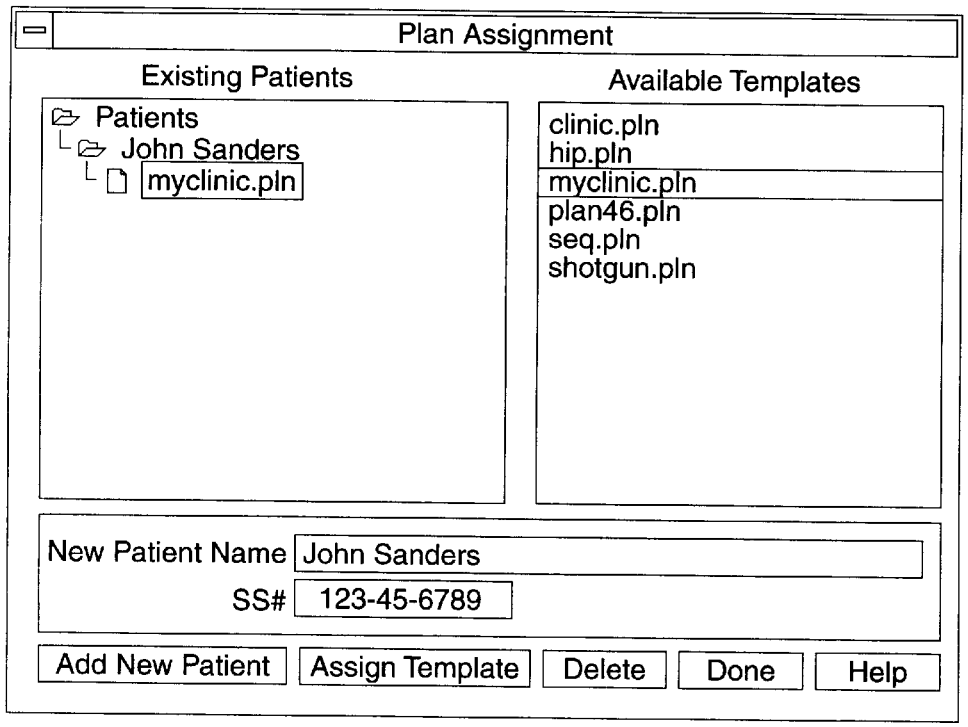
FIG. 32 illustrates how to open a patient's plan according to the present invention.

To assign the Clinic template to a new patient:

a. Click the Plan Administrator button on the toolbar 81 shown in FIG. 8. A template may be assigned to patients from the Go To menu or click the Assign Template to Patients button on the Main Directory as seen in FIG. 7. The Plan Assignment dialog box 230 appears and lists current patients and stored templates. FIG. 31 illustrates the Plan Assignment dialog box according to the present invention.

b. Click the template name to select the template.

c. Click the patient's name.

d. Click Assign Template 231.

e. To add a new patient, type the patient's name in the New Patient Name Field 232, press the Tab key to advance to the next field 233, and type the patient's social security number. Then click Add New Patient button 235. The patient's name appears within the Patients list on the left as shown in FIG. 32.

f. Click done button 234. The patient assignment is recorded and the patient assignment window closes.

If a completed plan is under a patient's name, GUI asks if a user wants to archive the plan. If a user answers "yes," the plan is saved in the patient's archive directory for later review and the name of the archived plan is no longer listed in the existing patient tree.

IV. PATIENT CHARTING

As described above, there are two different views available when delivering a patient's plan: Flow Chart view or Chart view. The Flow Chart view is ideal for simulating plan delivery in order to ensure the correctness of a new template. The Chart view is more suited for delivering care to a real patient and more closely resembles patient charts.

A. Charting in the Flow Chart View

A template assigned to a patient becomes part of the patient's plan and can be delivered. During the delivery operations, a user enters the results of tests and changes the status of orders when the order has been completed (i.e., filled).

To deliver a patient's plan using the Flow Chart view:

a. Choose Main Directory from the File menu to see the Main Directory window as seen in FIG. 7.

b. Click the Assign Templates 71 to Patients button to see the Plan Assignment window.

c. Double-click the patient's name in the patient list to see the templates that have been added to the patient's plan.

d. Double-click the template name beneath the patient's name to see that template in the Flow Chart view. At this time, the Chart view exists, but is hidden. By dropping down the window splitter "=", the Chart view is revealed.

Figure 33:
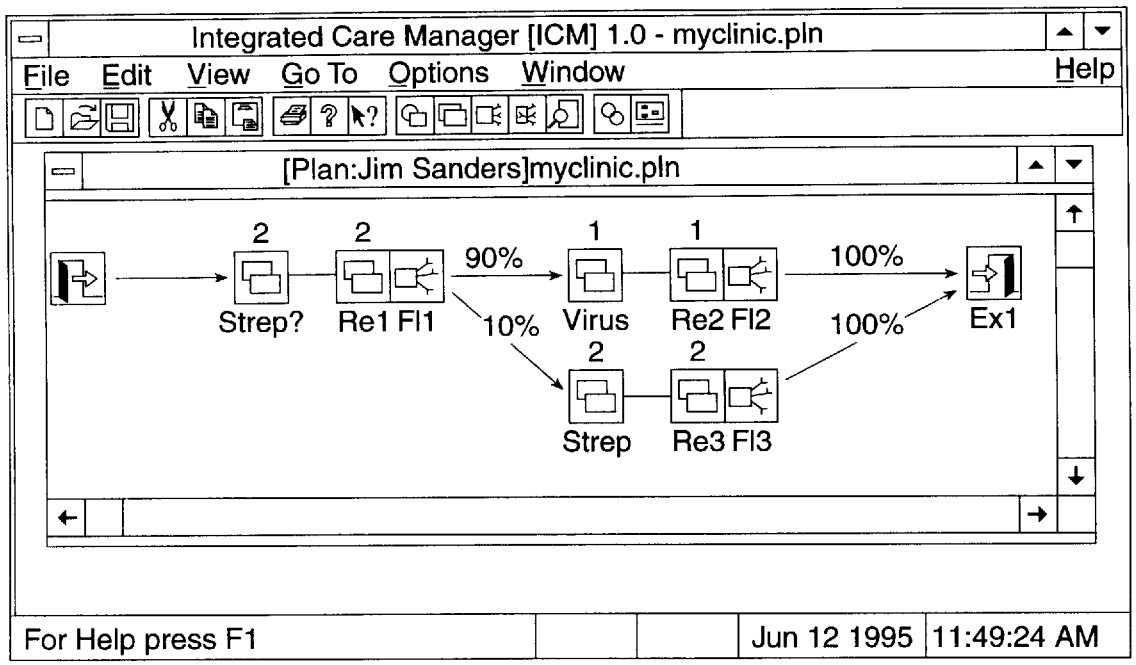
FIG. 33 illustrates patient charting in Flow Chart view according to the present invention.

FIG. 32 illustrates how to open a patient's plan according to the present invention. Specifically, double-click myclinic.pln folder presents "Jim Sanders" Flow Chart view as shown in FIG. 33. In this view, colors are used to distinguish between plan steps that (1) have already been completed, (2) are presently active, and (3) have not been completed.

A user can change the colors using the Color Preference command from the Options menu.

Nodes marked active contain orders that have been placed and are awaiting results. There may be more than one active node in the plan at one time, but the right most active node is where the next branching decision is made in the plan.

Figure 34:
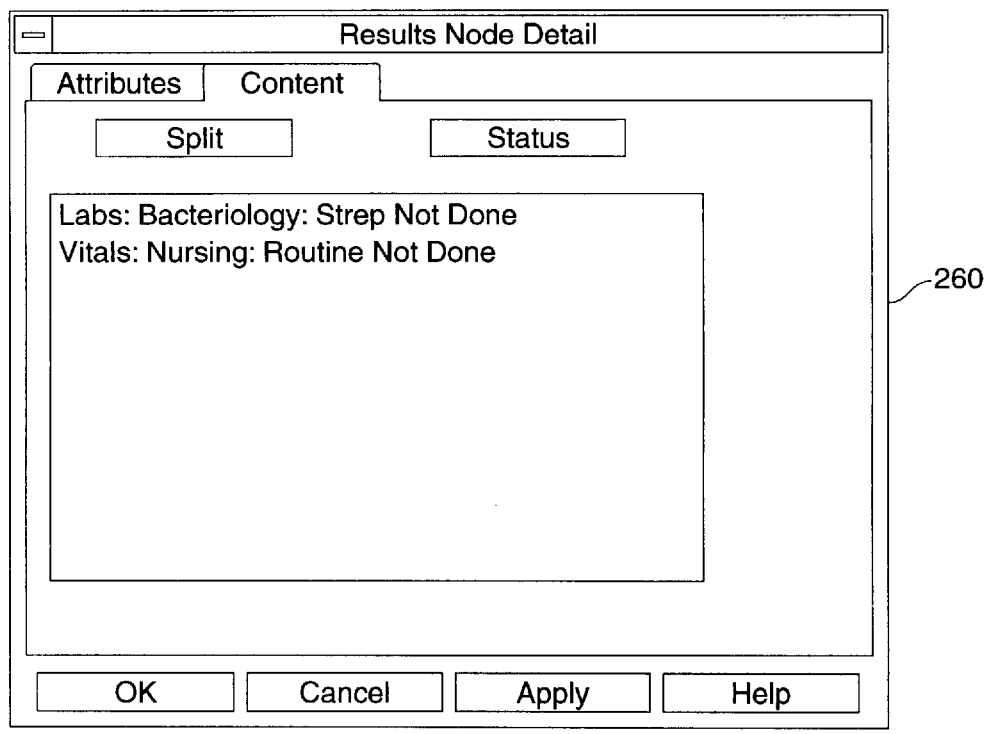
FIG. 34 illustrates a Result Node Detail dialog box according to the present invention.
Figure 35:
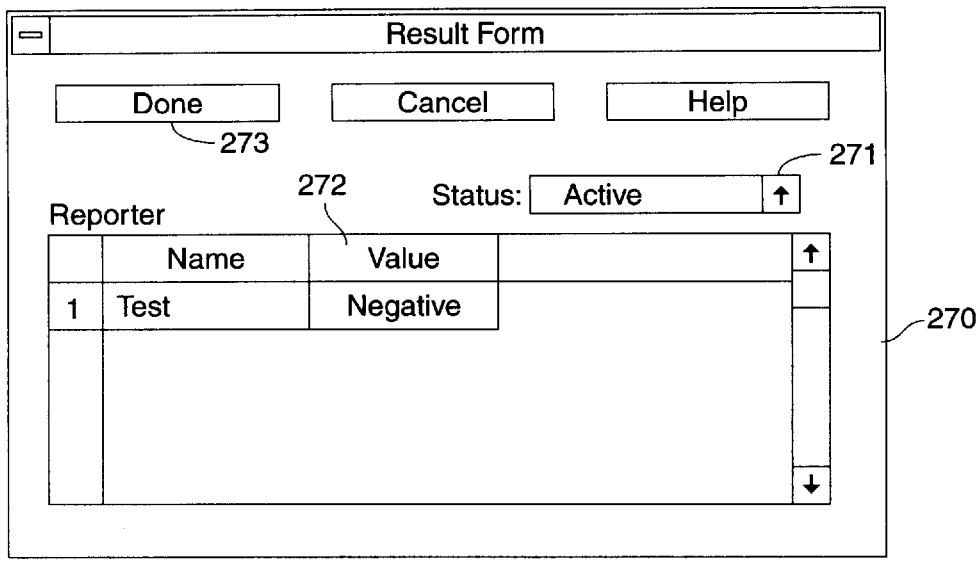
FIG. 35 illustrates the Order Result Entry Form according to the present invention.
Figure 36:
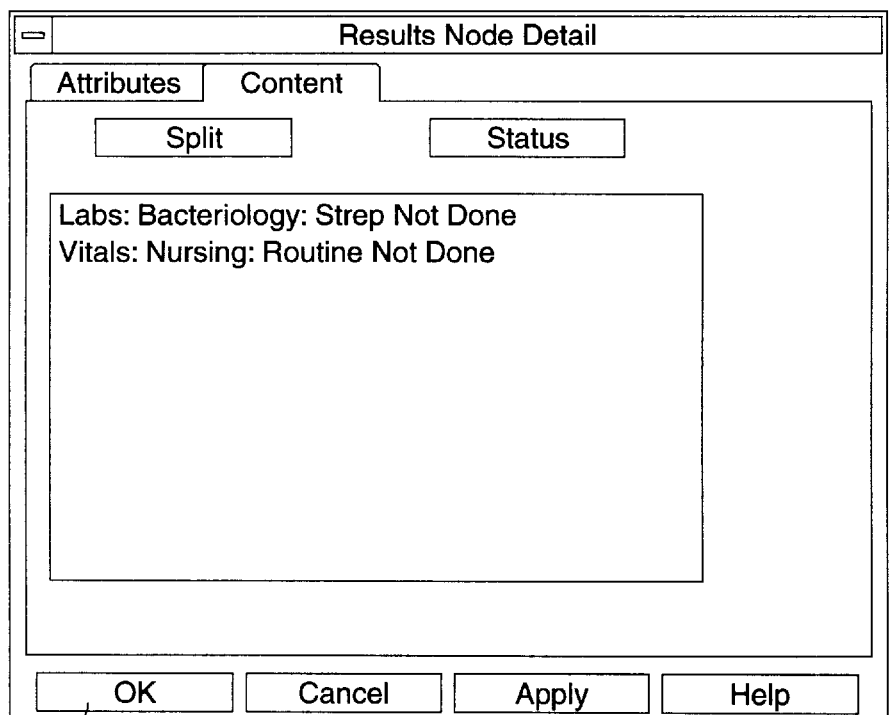
FIG. 36 illustrates a completed order status according to the present invention.

Each time an order result is entered, the rules in the Flow Control node are evaluated to see if enough information is available to branch to the next step in the plan. When all of the order results specified in a rule are entered, the rule is evaluated. If the rule is satisfied, the rule will become active and take the plan down the corresponding path.

e. Double-click the Re1 node to display the Result Node Detail dialog box 260 in FIG. 34. It lists work orders and their completion status. At this time, none of the work orders have been completed and all are marked "Not Done."

f. Double-click the first item in the Order Status dialog box. The Result Form dialog box 270, as illustrated in FIG. 35, appears. In this dialog box, a user enters values to indicate the results of tests and change the completion status of work orders. The test results are entered in the Value column.

g. Click in the value column 272 of the Test row. Type FALSE or N for negative (the default value), or TRUE or P for positive. For this example, type P.

h. Press enter or select another field.

i. Click the down arrow 271 in the Status box and change the status from Active (not done) to Done.

j. Click the Done button 273. The status has now been updated for this procedure, it is listed as Done in the Result Node Detail dialog box as shown in FIG. 36. The Vitals order remains Not Done.

k. Even though the Vitals order remains Not Done, Click OK 281 to close the dialog and view the plan flow chart.

The GUI, according to the present invention, automatically determines the next step in the care flow based on the results of the strep test even though the vitals were not completed. The Strep Flow Control node Fl1 in FIG. 23 is completed (shaded dark gray) and the Strep Flow Control node Fl3 in FIG. 33 is active (green).

In this example, both the Re1 and Re nodes are active (green) and awaiting result values. This is because the branching rule in the Flow Control node does not include any results from the vitals. If a user wants the branching logic to consider one or more of the vital statistic values (i.e., temperature to check for a fever), a user can modify the rule to reference the vital value(s). Even though the vitals are generally taken in advance (probably by a nurse even before the physician sees the patient and orders the strep test), and are normally available before the strep test results, this example demonstrates that the rules become active as soon as the results that they depend on are available.

1. Update the results of the Re3 orders in the same way you completed those for Re1.

At any time during charting, a user can open a Result node or Flow Chart Node to view its content after it has been completed. A user can also choose to chart from the View menu to see all the past activity in this plan at a glance.

1. Charting Into a Plan Node

When a user takes a branch down a path that leads to a Plan node in the patient's chart, the Plan node is highlighted in both the Flow Chart and the patient Chart views as shown in FIG. 37. The Plan node indicates it is Not Done 291 until you double-click on this step in the plan (either the Plan node in the Flow Chart view or the column entry in the patient Chart view). At this point, the Plan node is set to Done, indicating you have entered the Plan node.

When a user charts a patient plan into a Plan node, the previous plan is discontinued and the new plan is started. The view of the new plan will be used to continue charting. Whenever a user leaves a plan, the user is presented with a dialog box that asks if a user would like to archive the plan. It is generally a good idea to not archive the old plan when entering a Plan node.

2. Manually Executing a Plan

There are two ways to manually direct the execution of the plan: force the plan to branch, and reexecute a step in the plan.

To force the plan to branch down a specific path, regardless of the result values and the flow control rules, a user opens the right-most active Flow Control node, select the rule governing the desired path, and click the Execute button. The plan will branch down the specified path.

To reexecute a step in the plan, for example, if treatment has gone down one path and a user needs to back up the plan to go down another path, a user reexecutes the previous plan step. Click the order node to go back to and either click the Execute button on the tool bar 81 or choose Execute option from the View menu. The plan will back up to the selected node making it the right-most active node.

B. Charting in the Patient Chart View

Charting a patient using the Chart view is very much the same as charting in the Flow Chart view.

a. On the Main Directory seen in FIG. 7, click Chart Patients button 72. A user may also choose Go To Chart Patients menu on the tool bar 81.

A summary of all the patients is displayed. This example shows one patient and one plan (the clinic plan that treats strep throat).

b. Click a patient's name to display the patient's chart. When entering the patient chart, the Flow Chart view is usually hidden. While the Chart view is displayed, the window splitter can be used to reveal both views.

Figure 38:
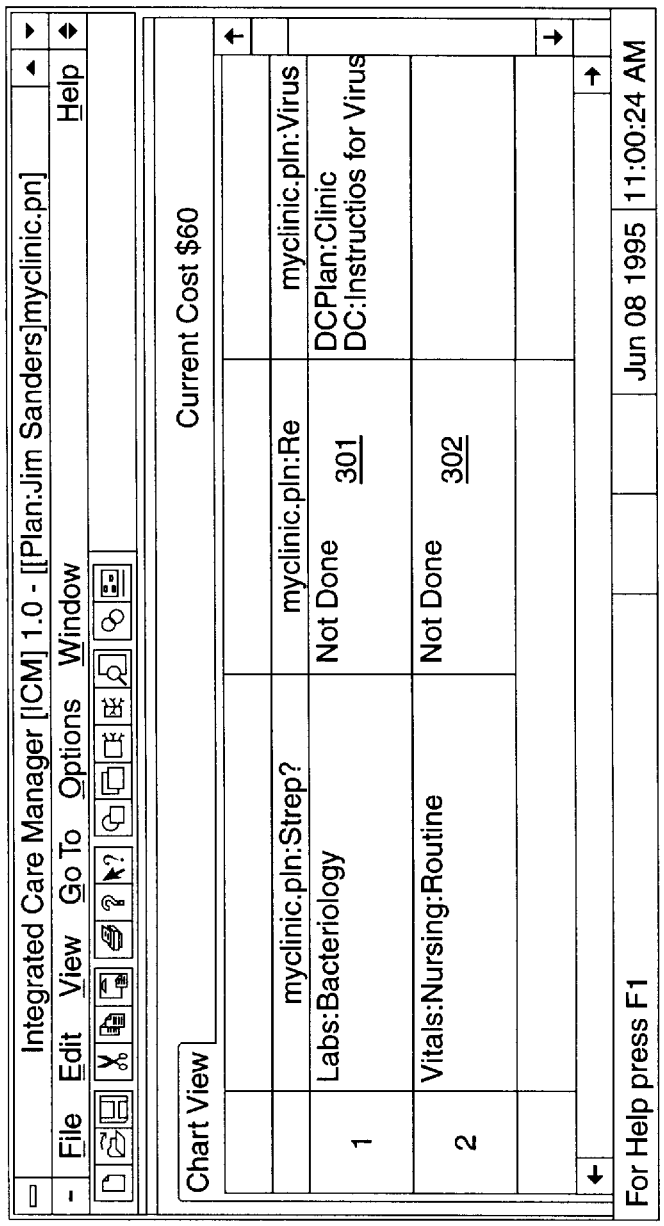

In the Chart view as shown in FIG. 38, each step in the patient's plan is represented as a pair of columns. The content of the Order node is shown in the first column. The corresponding order status is shown in the second column. Each step is labeled at the top with the step name and the time slot encompassing the step (in the example, time slots have been disabled so the step name is blank). The columns proceed from left to right by time slot.

The column with white cells 301 or 302 represents the active step and is ready to be charted. The gray columns to the right of the active column show the most probable path through the plan. The probability values associated with each rule determine the most probable path through the plan. In this example, the Virus path is the most probable.

c. Double-click the white cell 301 to the right of the Strep order to see the Results Form dialog box. Enter the results of the strep test (P for positive) and click the Done button to mark the work order "Done" as in charting in the Flow Chart view example above. The effect is the same; the plan branches down the Strep path. Also, as in the Flow Chart example, the Vitals results (Re1) are left active (since they have not yet been entered) and the results of the strep orders become active as shown in FIG. 39.

d. Enter the required results for the Strep orders to complete the plan.

To see the Flow Control node content on the chart, choose Show Chart Details from the Options menu to show the rules. An active rule will contain Bold characters. When a user closes the chart or switches to a different module, the GUI prompts a user to save the state of the patient's chart. If a user decides not to save the present state of the plan, it returns to its previous state; that is, the state the plan was in before you began charting. Therefore, no changes will be reflected the next time it is opened for charting.

1. Charting Into the Plan Node

A user may similarly chart into Chart view, as described above. Except when a user decides to archive the old plan, the order result information is not listed in the Chart view, while not archiving will leave the information in the Chart view as part of the patient history data.

C. Flow Chart and Chart View Logic Flow Diagram

Figure 40:
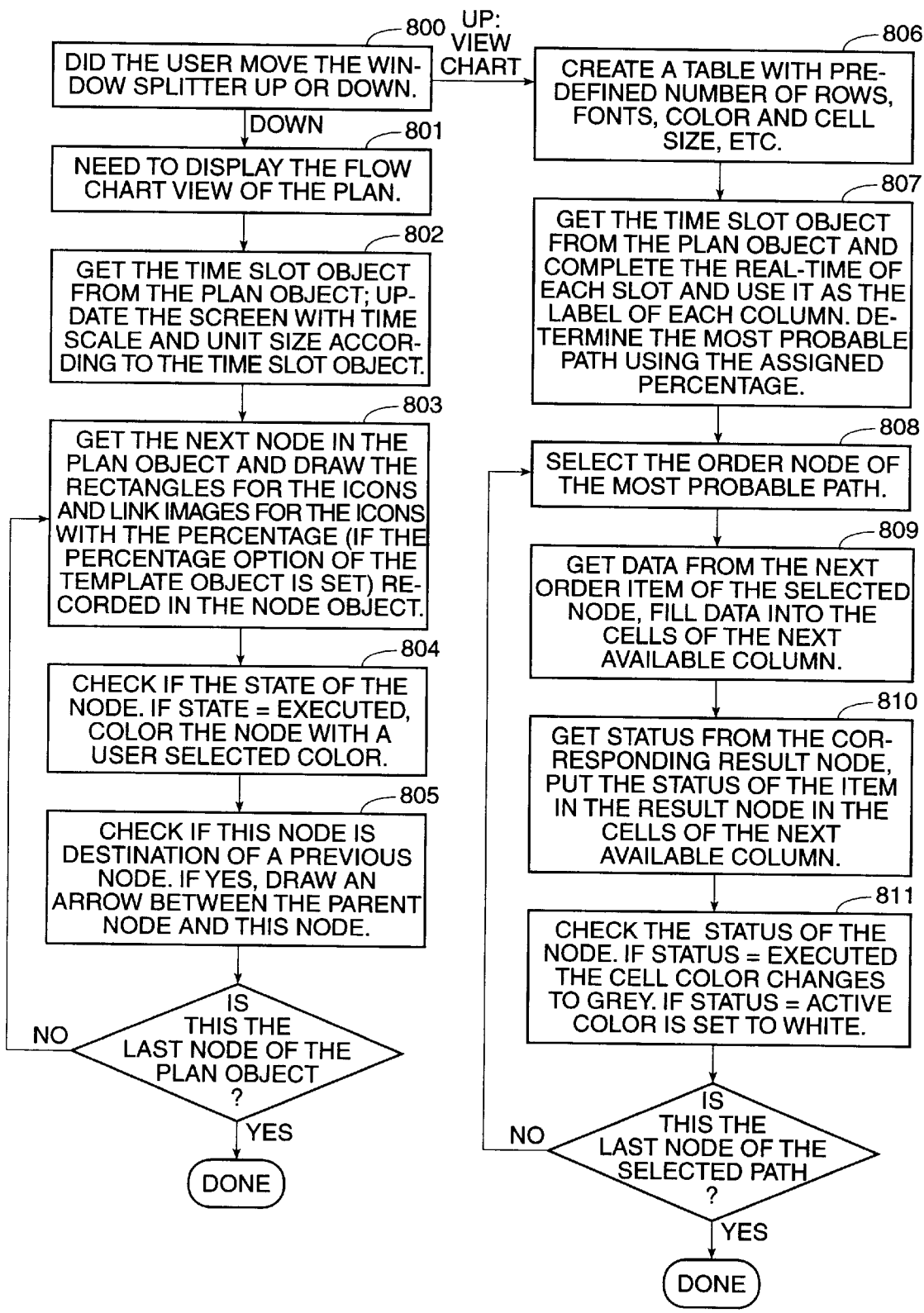
FIG. 40 illustrates a logic flow diagram of a Flow Chart and Chart view according to the present invention.

FIG. 40 illustrates a logic flow diagram for displaying a Flow Chart and View Chart according to the present invention.

In logic 800, a determination is made whether a user moves the window splitter up or down. If the user and is moved the splitter down, a determination is made in logic block 801 to display a Flow Chart view of a patient plan. Accordingly, in logic 802, a time slot object (real time slot 363 as seen in FIG. 27) from the plan object (plan object 360 as seen in FIG. 27) is obtained. The screen is updated with a time scale and unit size according to the time slot object. The node list in the plan searched for the next active node in the plan object obtained in logic 803. In logic block 804, if the state attributes of the node object is checked to see if it is executed. The node is then colored with a user-selected color if the state of the node is executed. A determination is made in logic block 805 whether the node is a destination of a previous node. If the node is a destination of a previous node, an arrow is drawn between the parent node and this node. A determination is then made whether the node is the last node in a plan object. If the present node is not the last node, the logic loops back to logic block 803. Otherwise a Flow Chart view is drawn. If a user selected the view chart, the logic proceeds to logic block 806. A table with predefined numbers of rows and fonts is drawn. The time slot object is then obtained from the plan object in logic block 807. The real time of each slot is also obtained and used as a label for each column. A determination for the most probable path is also determined by examining the probability value of each path in logic block 808. Data for the next order of the selected node is then obtained in logic block 809. This data is filled in the cells of the next available column. The status from the corresponding result node is then obtained in logic block 810. The status of the items in the result node in the cells of the next available column are then displayed. The status of the node is then checked in logic block 811 and colored accordingly. Finally, a determination is made whether the last node in the view chart form is the present node. If a present node is not the last node, the logic loops back to logic block 808. Otherwise, the view chart is displayed.

V. CUSTOMIZING A TEMPLATE OR PLAN

If the patient's treatment isn't covered in a generic template, a user can copy an existing template similar to one needed and modify it to suit a specific patient. A user can customize a template by adding nodes, deleting nodes, or modifying node contents in a Flow Chart view.

A. Deleting a Node

Deleting any of the nodes in a triplet removes the entire triplet. Exit nodes may be deleted separately and Start nodes may not be deleted.

B. Modifying the Clinic Template

Suppose a user has a patient who may have Strep throat but also requests a prescription for a preexisting condition such as migraine headaches. A user needs to modify the Clinic template to include a prescription for Tylenol III.

To modify the Clinic template:

a. Open the Clinic template that was previously assigned to a patient.

b. Double-click the Strep? node to open the Orders dialog.

c. Click Add button 117 in the Orders node detail dialog box shown in FIG. 11.

d. Double-click Meds, Pharmacy, and PO_Pain_Meds_Tylenol_III ($10.00) in the Command list of the Add Orders dialog box 122 shown in FIG. 12.

e. Click Place Order button 127 and then click Done button 124.

f. Click OK button 113 in the Orders dialog box 110.

The number above the Strep and Re1 nodes change to 3 indicating that there are now three work orders associated with these nodes.

The same set of operations to modify the protocol during the plan delivery phase may be used in the charting/walk-through module. In an embodiment, the customization can only be done in the Flow Chart view and the toolbox is hidden by default in plan delivery mode.

VI. EXPORTING PATIENT PLAN DATA

The GUI, according to the present invention, provides several ways to export data gathered during charting. DDE (Dynamic Data Exchange) allows GUI to notify another Windows application when orders are placed and rules are active. A patient plan may be exported in a format that can be read by applications such as Microsoft's Excel spreadsheet. FIG. 41 illustrates a plan element, exported from the "clinic.pln" and imported into an Excel Spreadsheet. A modified patient plan can also be exported as a generic template.

A. Using DDE

In the Options menu, the commands DDE Enabled/DDE Disabled, allows a user to export the data in the Result node to other applications that support DDE.

For example, an Excel spreadsheet can contain macros that will read the DDE data and enter them into various cells in the spreadsheet First, start Excel and open the spreadsheet. Then start the GUI Chart Patient module and choose DDE Enabled from the Options menu. When a user enters data into the results forms, the data is also sent to the Excel spreadsheet.

B. ASCII Export Format

When a plan is exported as an ASCII format file, each element in the plan is written on a separate line. Each line may contain several values that describe the plan element. These values are separated with commas and arranged in columns. This comma-separated value format is easily read by most spreadsheet and data base software, and other analysis programs.

C. Using Analyze Patients

ARAXSYS™ Solution's Analyze Patients module also allows users to extract data from a template and convert it to a standard format that other WINDOWS® programs can read.

a. Click the Analyze Patients button 73 from the Main Directory window as shown in FIG. 7. A dialog box opens and displays the list of patients a user has entered (from the Patient Assignment window).

b. Click the patient name to see a list of the templates integrated into the patient's plan.

c. From the list, select the plan template a user wants to export.

d. Choose the desired data format and click the Export button. A user will be prompted to enter a file name for the converted data file.

e. To input the data into the other application, open that application and use its Import command. This command is usually on the File menu.

A user can also print the converted data using the "Print" option on Export dialog box. The plan data is printed in a table format.

VII. MERGING HEALTHCARE PLANS

A. Merging Plans

When a new patient is enrolled and placed on a treatment protocol, for example, the first template is assigned to a new patient and the template becomes the patient's master plan. It is often the case that the patient will need to be placed on a new, possibly unrelated, treatment protocol, such as started on a new template, while the first plan is still in effect, such as a pregnant woman on a prenatal plan with a sore throat. To handle these cases, a user simply assigns a new, additional template to the patient.

At this point, the physician has to decide whether to merge the new template with the master plan, or start the template as a separate plan in parallel with the master plan. The default behavior is to execute the two plans in parallel, but this may be undesirable if the orders in the new plan conflict with the orders in the master plan.

When there is a chance of orders conflicting between plans, a user should merge the new plan into the master plan. The merge process will allow a user to resolve the conflicts and plan out a treatment course that covers both conditions effectively.

B. The Merge Process

The merge process begins when a template is assigned to a patient that is currently on an active plan. This section explains the merge process using a simple example scenario to illustrate each step. In the scenario, Mr. Sanders is having his hip replaced according to the hip.pln template. Presently, Mr. Sanders is on day four of the hip replacement plan and is being treated for a fever that has developed after surgery. On this day, Mr. Sanders manages to hurt his wrist on the bed rail while reaching for his book. His doctor assesses the swelling and decides to place him on wrist trauma protocol designed specifically for patients with an intravenous ("IV"), that is, the protocol prescribes IV medications instead of oral medications. Since the wrist trauma protocol will likely impact the hip replacement plan, Mr. Sanders' doctor decides to merge the wrist plan with the hip replacement plan. In order to merge the plans, the following steps are completed:

a. First, assign the wrist trauma template to the Mr. Sanders master plan—the hip.pln he has been on for several days. Click the Assign Templates to Patients button 71 from the Main Director shown in FIG. 7 to bring up the Plan Assignment Window shown in FIG. 42.

Figure 42:
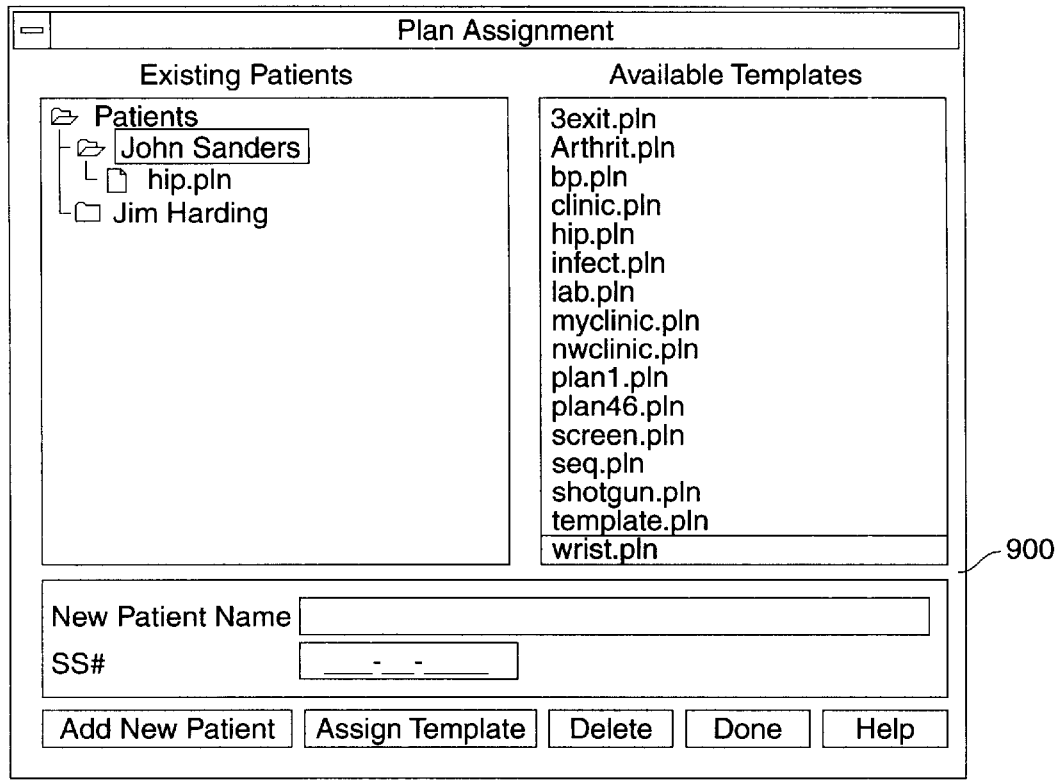
FIGS. 42–42a illustrates the Plan Assignment dialog box according to the present invention.
Figure 42A:
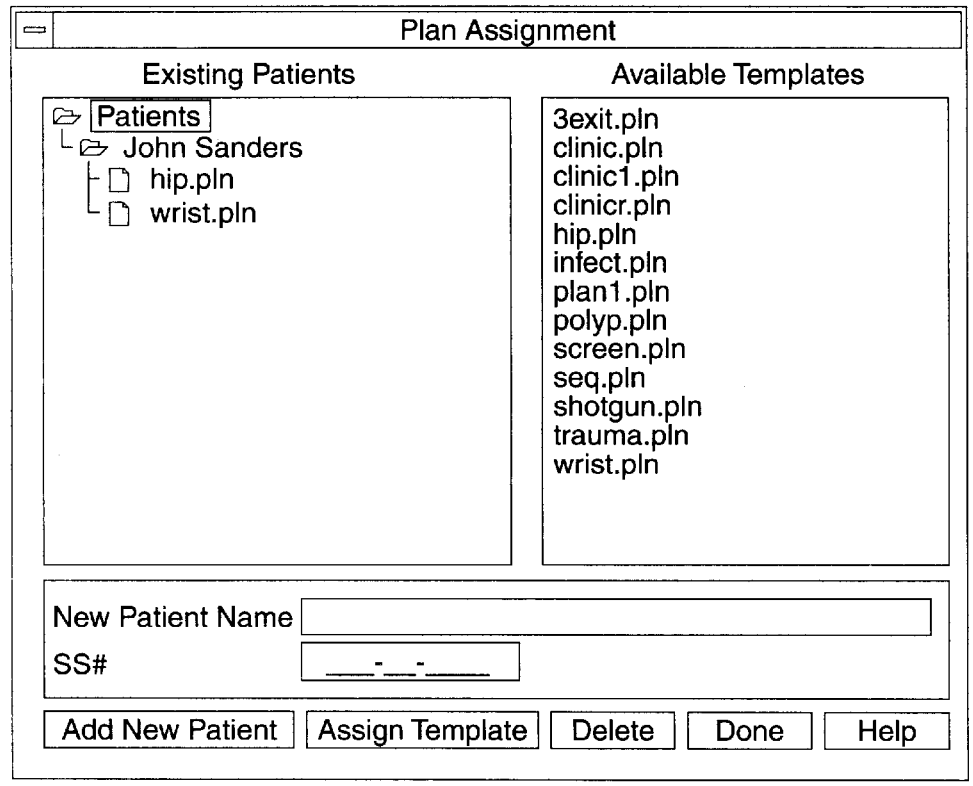
Figure 43:
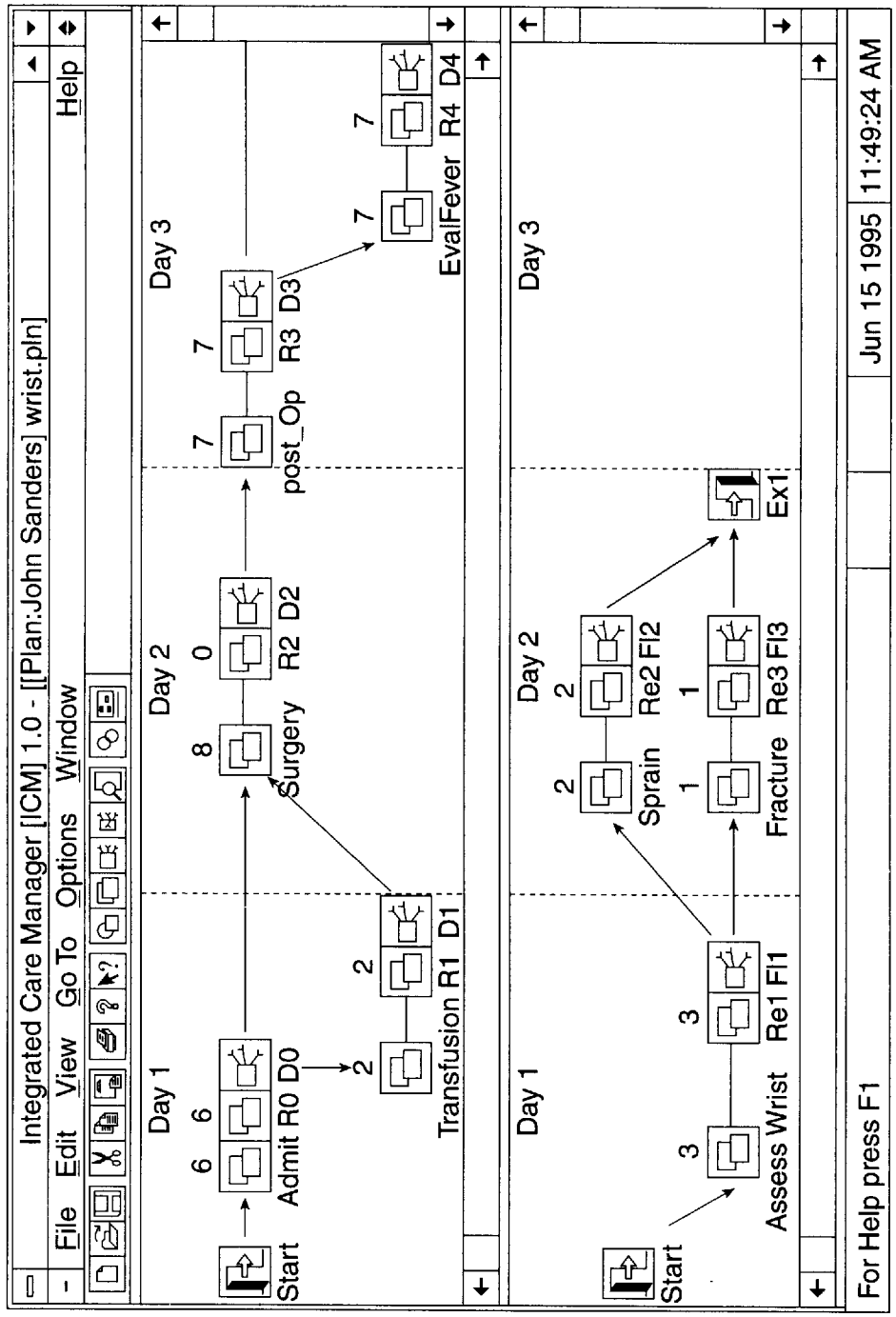
FIG. 43 illustrates a Flow Chart view of two templates according to the present invention.

FIG. 42 shows how the Plan Assignment window looks just before the wrist.pln is assigned to Mr. Sanders. The wrist.pln template and Mr. Sanders are selected.

b. Click the Assign Template button 900. The wrist trauma plan, wrist.pln, is now listed beneath the hip replacement plan, hip.pln, as shown in FIG. 42*a*.

c. Double-click the wrist.pln line listed beneath Mr. Sanders' name in the patient list. Doing so brings up the wrist trauma plan, wrist.pln, in the Flow Chart view. The first triplet is highlighted to indicate it is the next step in this plan.

d. Maximize the wrist.pln window and pull down the splitter bar to divide the Flow Chart view in half. The splitter bar is the thin, raised gray bar just below the Flow Chart view window title bar. This reveals both the wrist trauma plan and the master plan, namely the hip plan in this example, as shown in FIG. 43.

Figure 44:
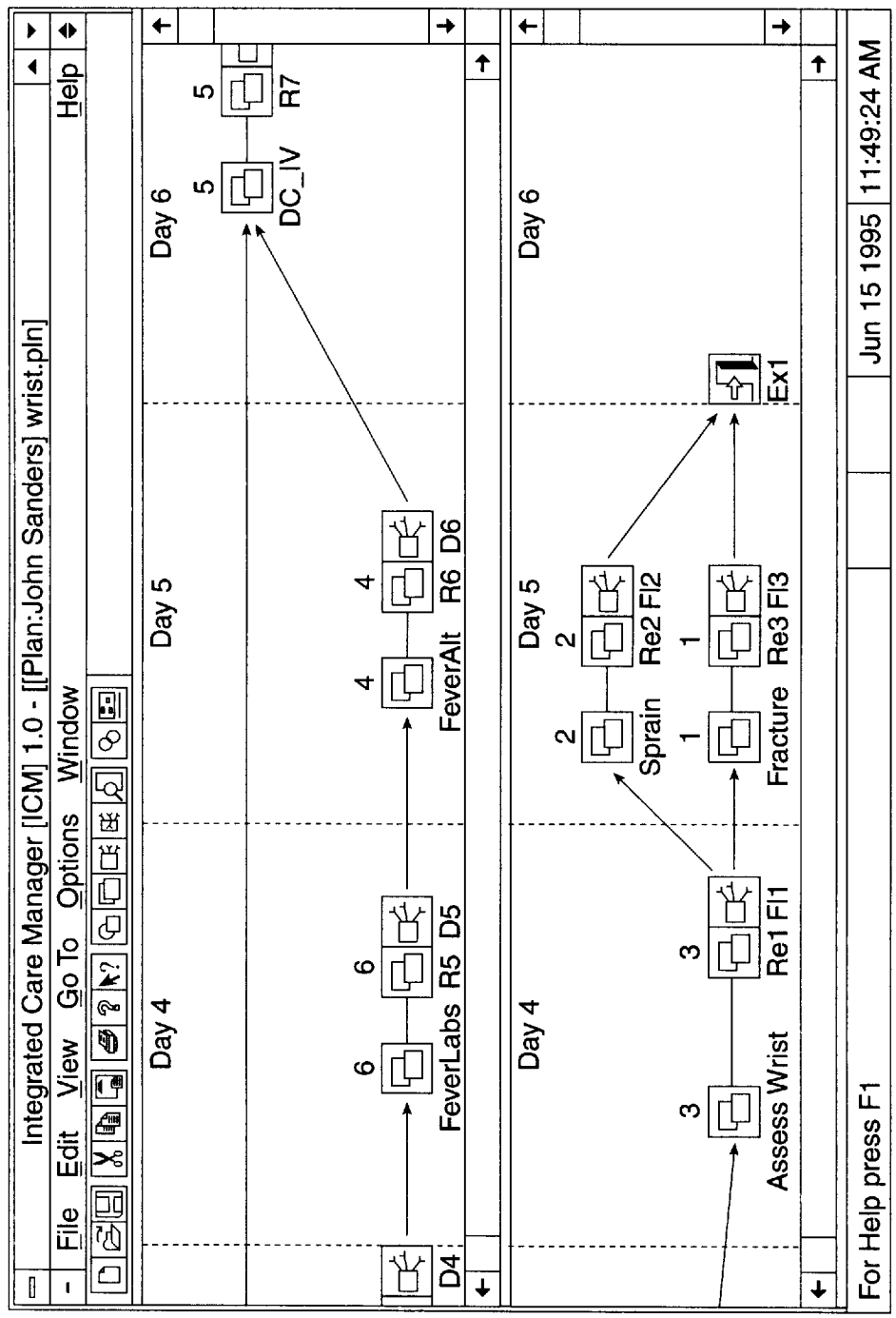
FIGS. 44–46 illustrate a merging of two templates according to the present invention.

When the plan is first opened, it shows both plans starting from the first time slot. When plans are merged and have different time slot settings, the time slot setting from the plan with more narrow focus.shorter duration is selected for the integrated plan. For this reason, it may be necessary to adjust placement of nodes in the plan that changed to make sure nodes are in the proper time slots. In this example, both plans have time slot settings by day and this adjustment is not necessary.

e. Before a user can merge the wrist plan into the active hip plan, a user needs to move the wrist nodes to day four where the hip plan is presently active. Select the Order Node in the first triplet in the wrist plan and choose Select All Nodes Right from the Edit menu. This selects all of the wrist plan nodes. Now, drag the nodes to the right until the first triplet is positioned in day four and the second set of triplets is positioned in day five. Next, scroll the hip plan to the right until both plans are aligned by time slot. Adjust the scrolling so that a user can see all of day four and five. When a user is done, the Flow Chart view window looks similar to FIG. 44.

The nodes in the wrist plan are merged into the hip plan at day four because Mr. Sanders is presently on day four of the hip plan when the wrist injury occurs. In this example, the merge needs to take place on day four. But in general, selecting a time slot may not be apparent because more than one time slot may be active in a plan.

Nodes in the next plan step become active once a rule is satisfied in the current plan step. Rules often only reference one or two order results out of all that may be available in the triplet. If one of two orders are filled and show results that trigger a rule, the plan may branch to the next step before some of the other orders are completed. When this happens, two steps become active in the plan. The outstanding orders may be filled in the previous step and the new orders may be filled in the newly activated step. But, since the plan has moved to a new step, the rules in the previous step are no longer checked; they no longer direct the plan flow.

The right-most active triplet is the leading active triplet and is the site of the next branch in plan. Nodes in the second plan may not be merged into time slots before the leading active node in the master plan. A user cannot merge a node before this triplet in the master plan, because the new node would not be able to participate in the branching decisions.

Figure 45:
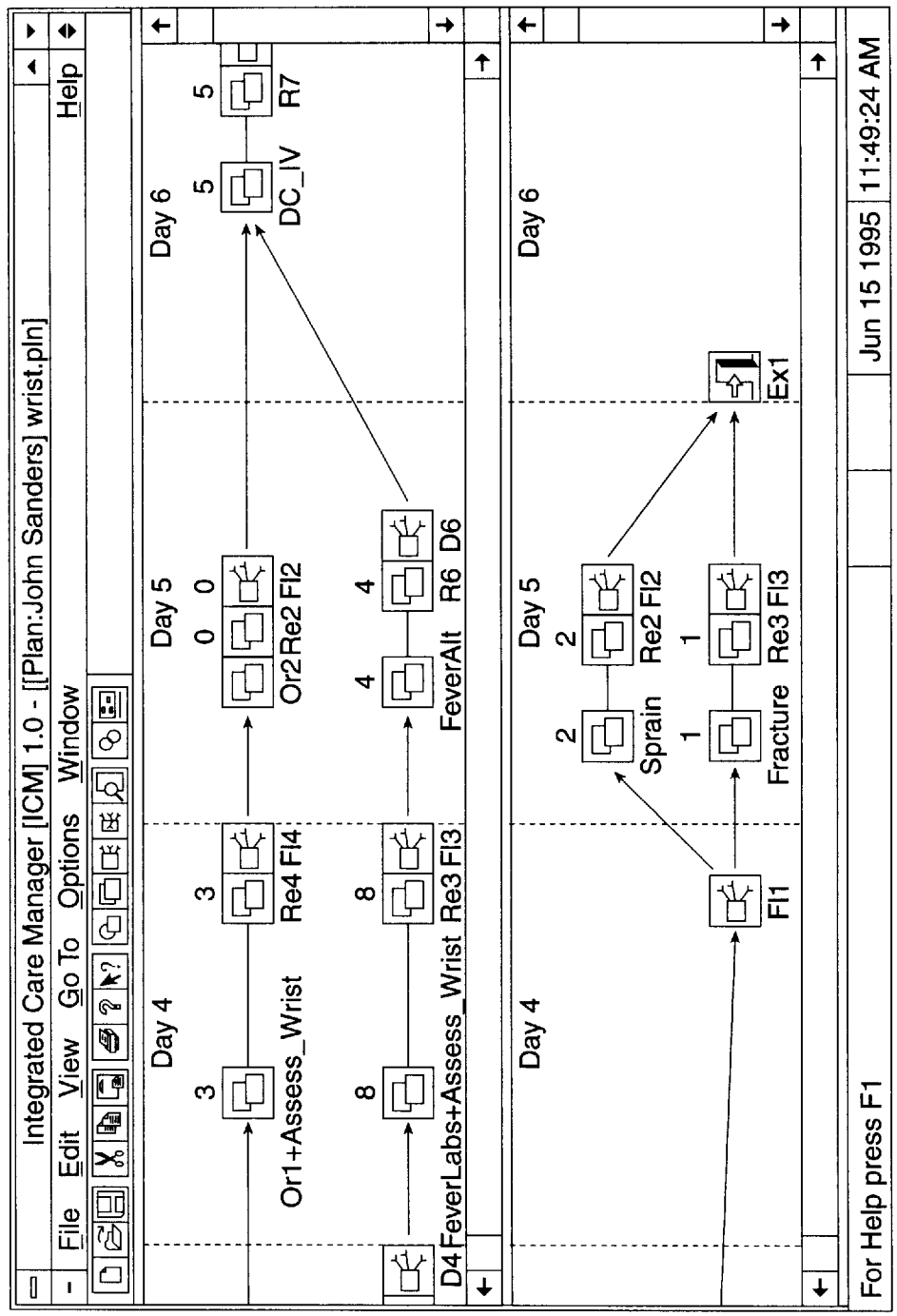

Since nodes are merged on a time slot by time slot basis, a user needs to reposition the nodes to make sure that no more than one plan step is present in each path in the day four and five timeslots. A user cannot have two or more triplets in a sequence, or a triplet followed by an exit node in the same time slot. Since the second step in the wrist plan contain triplets in multiple paths (the triplets are on separate paths), it is correct to leave these triplets arranged vertically in the same time slot as long as they are in separate branches of the plan.

f. Now that all of the nodes have been positioned properly, a user is ready to merge the first (active) step in the wrist plan with the active step in the hip plan. Select the order node in the wrist plan and choose the merge option from the Edit menu. FIG. 45 shows what the two plans look like after merge (and some rearrangements done for cosmetic reasons).

The Assess_Wrist triplet is merged into both paths in the hip plan. Since no triplet is present in the upper path (the one that would have been taken had Mr. Sanders not developed a fever after surgery), the Assess_Wrist triplet is inserted in its entirety (minus rules in the Flow Control node). In the second path, the orders from the Assess_Wrist Order node are added to the orders in the Fever_Labs Order node. Notice that before the merge the Assess_Wrist node contained three orders and the Fever_Labs node contained six orders, but after the merge the Fever_Labs+Assess_Wrist node only has eight orders. This is because both nodes contained the same order for pain medication. Duplicate orders are removed during a merge.

Figure 46:
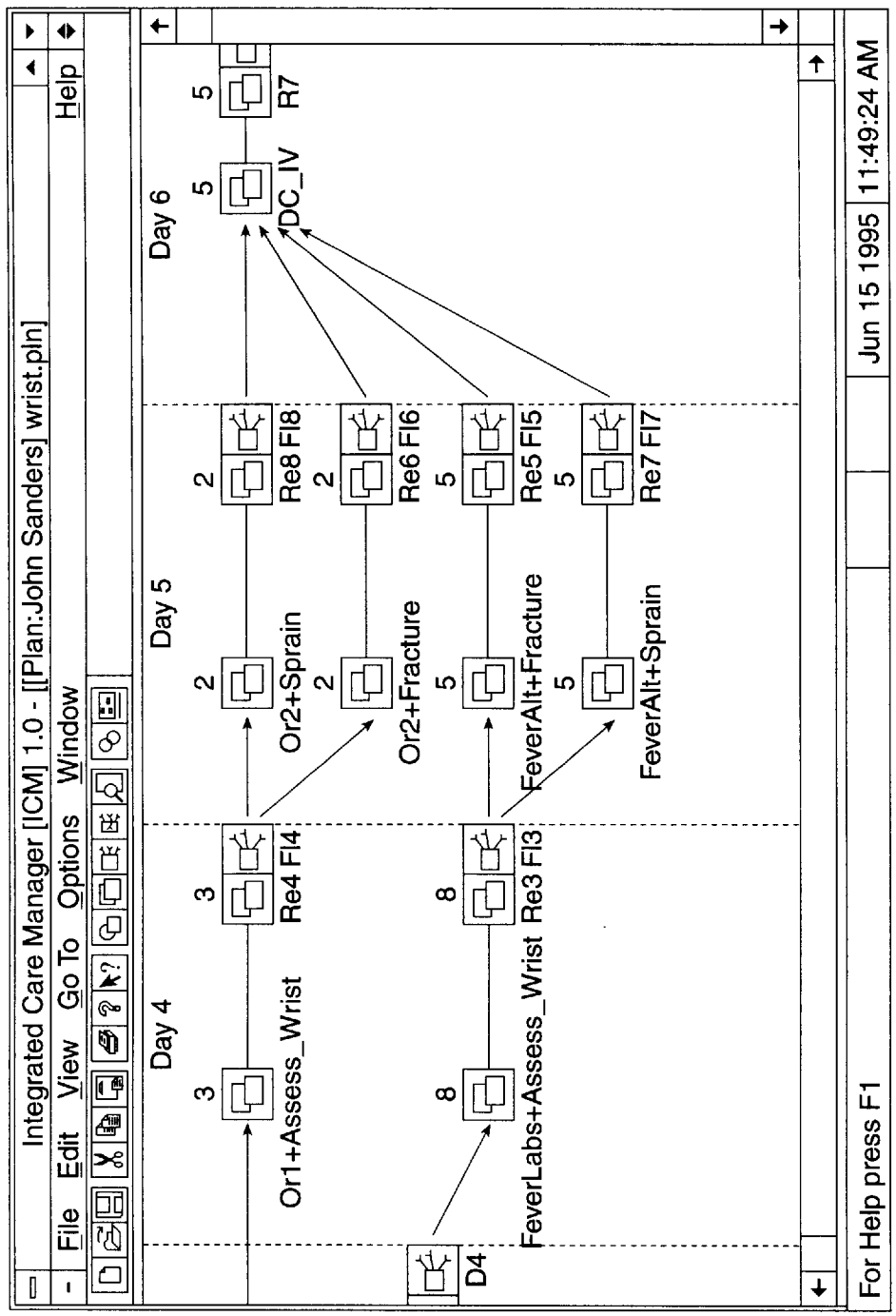
Figure 47:
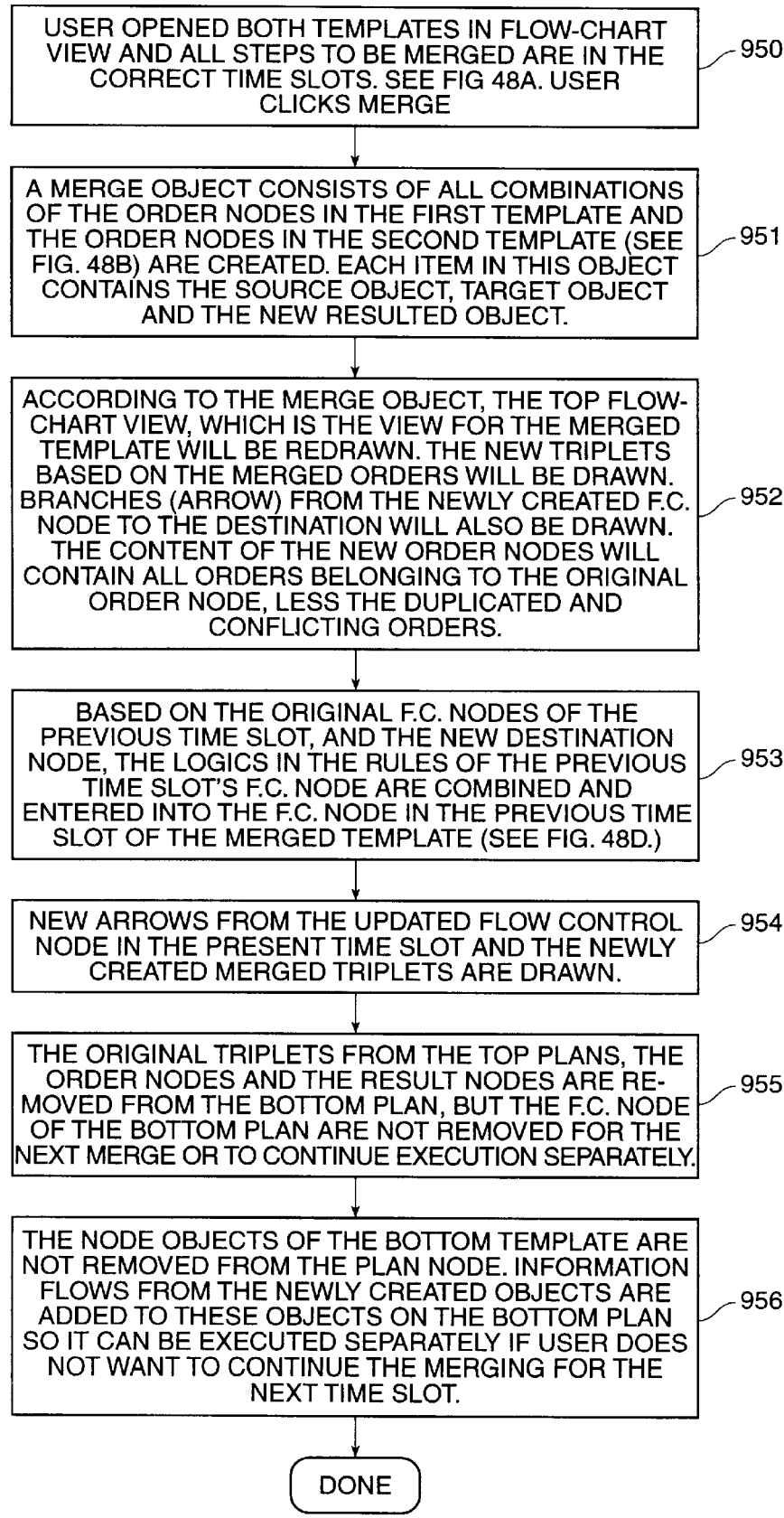
FIG. 47 illustrates a logic flow diagram of merging two templates according to the present invention.

The rules from the Assess_Wrist triplet are left in a solitary Flow Control node as a place holder until the next step in the plan is merged.

g. Merging the second step is similar to merging the first step. Select either of the Order Nodes in the wrist plan and choose the Merge option from the Edit menu. After rearranging the nodes a little and opening the hip plan all the way, the resulting merge appears as in FIG. 46.

As in the merge of the first step, orders were combined and duplicates were removed. This time, however, the rules from the previous step were merged into the Flow Control nodes to reflect the branch in the wrist plan between treating a fracture and treating a sprain.

This simple example illustrates the basic steps required to merge two plans, but this simple example does not highlight any conflicts that may arise during a merge. The merge removes duplicate orders, but it does not remove similar orders. In the example, the two plans prescribed the same pain medication, but in general, that may not be the case.

After the merge, a user needs to review the orders to make sure the combination of orders still makes sense. If another pain medication had been prescribed in the wrist plan, the result of the merge would contain two orders for similar, but different, pain medications. Since the pain medications prescribed for the hip plan are probably well-suited to handle any pain from the wrist injury, a user would probably want to remove the second pain prescription that originated from the wrist pain.

There are several types of conflicts that may appear after a merge that must be addressed. Medications may conflict with one another (e.g., two similar, but different pain medications are present). Orders may need to be delayed based on the new condition (e.g., it is impossible to complete the combined set of orders in the designated time slot). New orders may need to be added in addition to the sum of the merged orders (e.g., since Mr. Sanders injured the wrist that had the IV site, the IV site needs to be moved to the other arm). In addition to these conflicts, there are numerous unforeseen conflicts that may occur when orders from unrelated templates are combined. Users can specify the rules to resolve these conflicts and store the rules in the library.

The example scenario indicates several of the adjustments that must be made to the two plans before they are merged, but there are a few other constraints that must be addressed in the general case. A user must properly arrange the nodes in the two views so that they meet with following criteria before merging the triplets in a time slot.

First, both plans must have the same time scale setting. They must be both by day or by shift or by visit, etc. If the two plans have different time scale settings, change the time scale in the plan with the more broad time scale setting. For example, if one plan is set to days and the other is set to shifts, a user should change the plan that is set to days to a plan set with shifts. When the time scale setting is changed from days to shifts, a user should reposition the nodes into the desired shifts within the desired day because the nodes do not move when a user changes the time scale setting.

Second, two or more triples may not be in a sequence, or a triplet followed by an exit node in the same time slot. Since a single plan step can contain triplets in multiple paths, or triplets may (and probably will) be arranged vertically in the same time slot as long as they are in separate branches of the plan.

Third, new orders may not be merged into previously executed steps in the master plan. Nodes in a second plan may not be merged into time slots before the leading active node in the master plan.

Fourth, nodes may not be merged that have already been completed. If a user has been working with the second plan in parallel with the master plan (e.g., the user has not merged plans yet) and then a user decides to merge nodes, a user must start merging with the leading active node in the second plan. A user cannot merge fully or partially completed nodes (i.e., a triplet with a few orders outstanding) to the left of the leading active node in the second plan. After merging the leading active node, a user can then merge nodes in the subsequent time slots, but each time slot must be merged in order from left to right.

Error messages are displayed if the plans do not meet these criteria. A user can fix the problem and try again.

Once a user begins merging nodes, a user can stop at any time. Those nodes left unmerged will be maintained as parallel paths until they are merged. If the plan advances to one of these parallel paths and they remain unmerged, they can be charted in parallel.

During the merging process, a user will probably need to move nodes around. There are several selection options under the Edit menu to help a user select a group of nodes. For example, a user can select a node, choose the "Select All Nodes Right" option from the Edit menu, and drag all of the selected nodes to the right.

C. Merging Two or More Templates Logic Flow

Figure 48A:
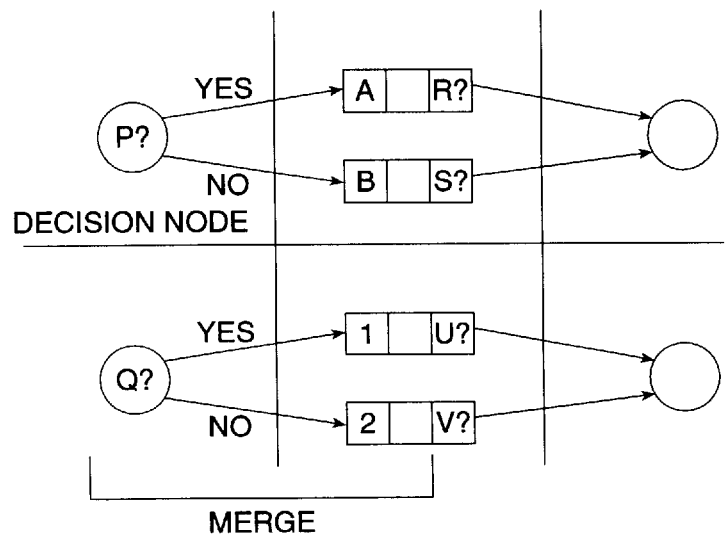
FIGS. 48a–48e illustrate a logic view of merging one time slot of two template nodes according to the present invention.

FIGS. 47 and 48a–48e illustrate the logic of merging two or more templates. A user opens two templates to be merged in a Flow Chart view in logic block 950. The user arranges the two templates so that they correspond to correct time slots. An example of two templates to be merged which are aligned in correct time slots is shown in FIG. 48a.

Figure 48B:
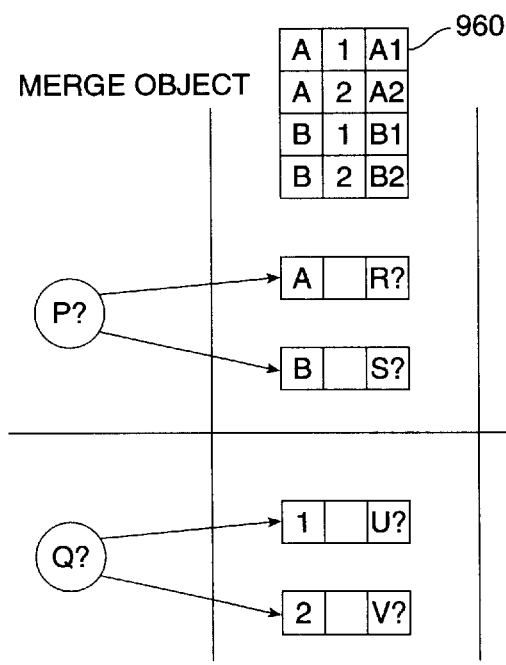
Figure 48C:
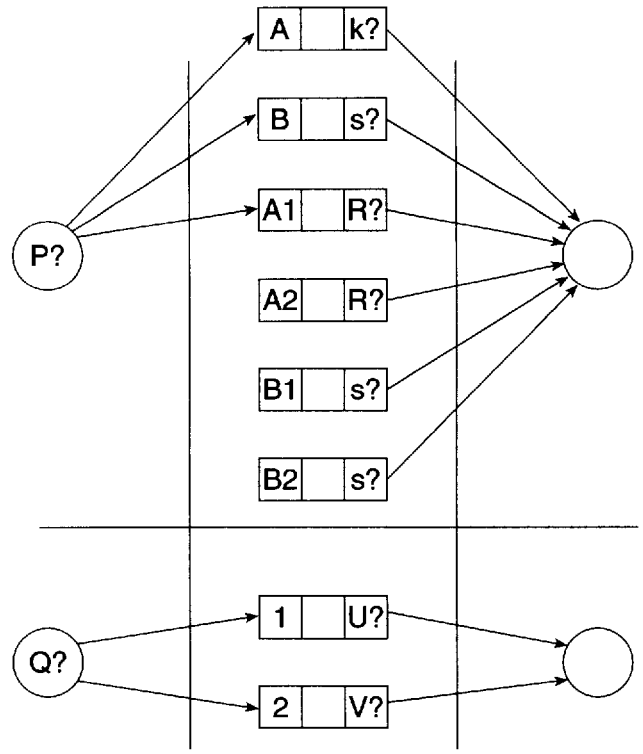
Figure 48D:
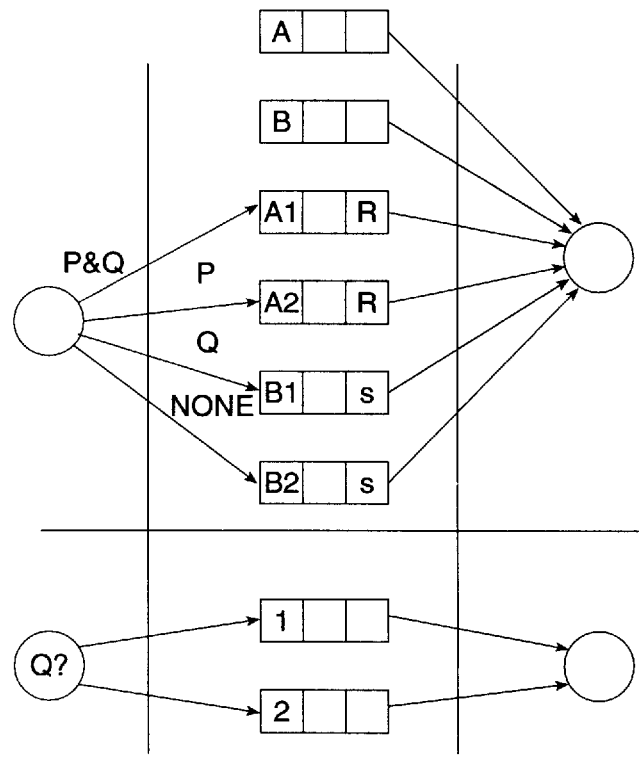
Figure 48E:
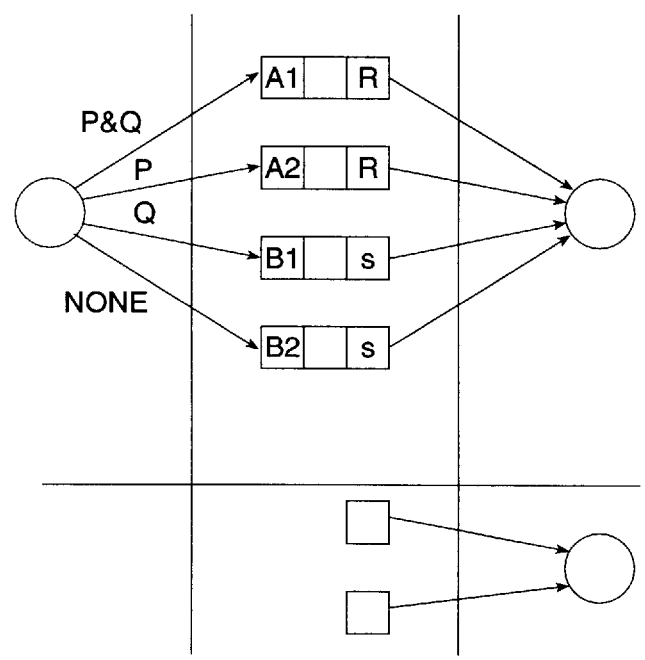

A merge object is constructed in logic block 951 and illustrated in FIG. 48b. P? and Q? represent flow control node rule expressions. For example, P? represents the rule expression "If test result is positive . . . " go to target order triplet A, otherwise target order triplet B. While Q? may represent the rule expression "If temperature is high . . . " go to source order triplet 1, otherwise go to source order triplet 2. The merge object consists of all combinations of Order nodes in the first template and second template. Each item in this merge object contains the source triplet order objects 1, 2, the target triplet order objects A, B, and the new resulted triplet order objects called A1, A2, B1 and B2. Table 960 illustrates the various combinations of obtaining the resulted order triplet objects. A top Flow Chart view of the in progress merge template is drawn using the merge object in logic block 952 and as illustrated in FIG. 48c. New order triplets, including A1, A2, B1, and B2 are drawn combining the various order triplets, as shown in FIG. 48d. For example, a possible positive test result and high temperature would cause flow to be directed to new order triplet A1. Branches from these new triplets will also be drawn. The content of the new triplet order nodes (A1, A2, B1, B2) will contain all orders belonging to the original order nodes (A, B, 1, 2), less the duplicated and content conflicting orders. Logic block 953 compares order items from order node objects and determines if duplicates or conflicts exist. The action or rule taken on duplicate orders can be stored and retrieved from a library item. In logic block 954, new arrows from the updated flow control node in the present time slot and the newly created merged triplets are drawn. In logic block 955, original triplets A and B are removed from the top Flow Chart view. Further, result nodes U? and V? are also removed from the lower Flow Chart view. However, the flow control node of the bottom plan remains in order to continue execution separately or for further merging. FIG. 48e and logic block 956 illustrate the merged template according to the present invention. The node objects of the bottom template are not removed from the plan node. Information control connections between order triplets A1, A2, B1, B2 and the lower flow control nodes are added internally (not shown in FIG. 48c) in order to allow for separate or parallel execution.

D. Outcome and Limitations

Every time a user selects the merge command, command and result nodes in the lower plan disappear. The number of items in the master plan node will increase by the same number which used to be in the lower plan. If there are multiple paths in the time slot in the lower plan (the merging plan), there will be new nodes created in the master plan to represent the merged plan.

Nodes containing zero items may be created during merge. These "dummy nodes" are created to carry internal information that must be preserved after the merge.

Flow control nodes in a time slot are not merged during the merge of this time slot. They are merged when the next time slot is merged. If a user chooses not to merge the rest of the plan, these nodes and the rest of the plan stay intact and the remaining plan is delivered in a parallel fashion as if there were two plans active simultaneously. A user can merge a few time slots and decide to postpone the rest of the merge by saving the plans using the Save command.

There is no specific limit on how many plans a user can merge. However, a user must merge them two at a time. The Chart view always records the actions taken in all plans assigned to a patient Whenever a user assigns a new plan to a person, the present invention detects if any of the existing plans have been completed. If a plan has been completed, the GUI asks a user if the completed plan should be archived. A user should archive a completed plan unless a user wants to refer to the information in the completed plan while charting a new plan. Archived plans do not appear in the Chart view but can be viewed separately with the Open command from the file menu.

VIII. SERVER OBJECTS TO SUPPORT GRAPHIC USER INTERFACE (GUI)

The graphic user interface according to the present invention is implemented using object-oriented structure software design. An example of object oriented structure design is described in *Object Oriented Design with Applications;* Booch, Grady, Benjamin/Cummings Publishing Company, Inc. (1991), incorporated by reference herein. A GUI server is implemented using objects and methods defined below. However, it should be understood that other software design principles and architectures could be similarly used to carry out the present invention.

1. General Server Object Interfaces

Figure 26:
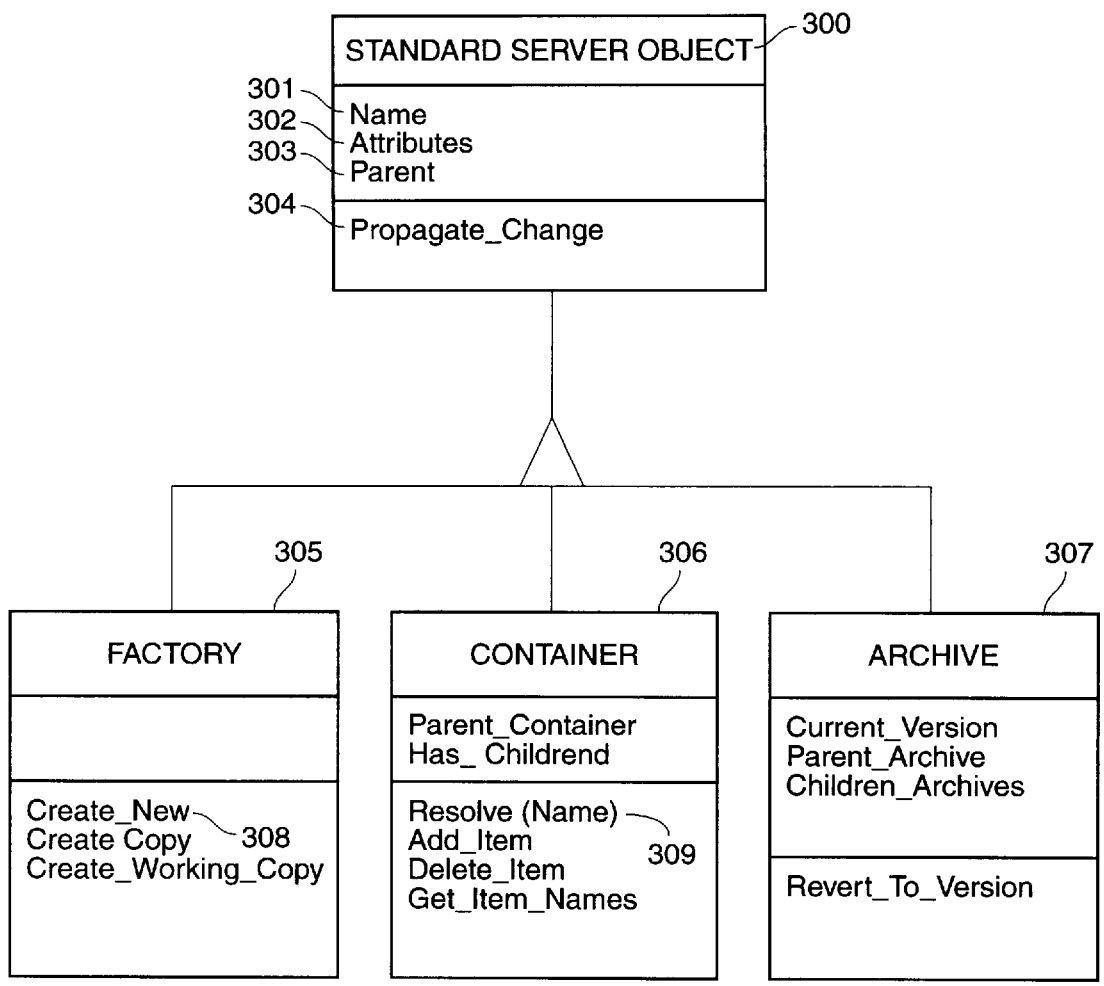
FIG. 26 illustrates the standard server object interface according to the present invention.

Every GUI server object 300 supports several standard interfaces. FIG. 26 illustrates the server object interfaces that may be mixed into any or all of the GUI server objects. For example, an order node may have a corresponding server object having the illustrated interfaces. FIG. 27 illustrates the relationship between various server objects according to the present invention.

a. Standard Server Object Interface

The standard server object interface is supported by every distributed object in the GUI server. Every object 300 has a Name 301, Attribute List 302, and Parent attribute 303. In addition, every server object contains a Propagate_Change method 304.

(i) Name Attribute

The Name attribute 301 is unique for the instance of the GUI server object in its context (e.g., a node in a plan, an order in a node, etc.). The Name attribute 301 will likely conform to the Name type expressed in The Common Object Request Broker: Architecture and Specification, Version 2.0 ("CORBA Standard") incorporated by reference herein.

(ii) Attributes List Attribute

The Attributes List 301 is a general set of name/value pairs associated with every server object instance. These attributes may be "well known" (e.g., expected to be present) or specific to the object class. Well known attributes include Category, Department, and Cost. In orders, attributes include results, order qualifications (e.g., drug dosage), and start and finish times. Attributes 302 may be referenced by rule expressions to determine the branch a patient takes through their plan.

(iii) Parent Attribute

Most GUI server objects are contained within some other object. The change notification scheme requires a given object to identify what changed at their level and then propogate a change notification up to their parent. The Parent attribute 303 keeps track of which object is currently the parent of a given object. Parentage can change over time.

(iv) Propogate_Change Method

A change notification scheme according to the present invention uses a chaining mechanism to specifically identify what changed in the GUI server data. When the change information is compiled, it is passed to all client applications that have registered for change notices.

The change information is compiled into a stack object. The object that makes a change pushes an entry into the stack indicating what changed at their level. The object then invokes the Propogate_Change method 304 in the parent (through the Parent attribute 303). The parent pushes an entry into the stack indicating the change at their level and invokes Propogate_Change method 304 in their parent, and so on. At the top level (a GUI Server Component object like a plan, template, patient, etc.), the stack is included in the change even that is distributed to all the CORBA clients that have registered for change notices.

When the client receives the change notice, the client pops the change entries off the stack. Each change entry identifies the change at each level. If the user of the client application is not able to access the element that changed, the change notice may be ignored.

For example, an order result value is updated (set by a client) during plan delivery. The Attribute of the result object creates a change stack object and places the first entry identifying itself as having changed. Attributes need to notify all of the rule expressions that depend on them using a notification mechanism provided in the CORBA standard referenced above. Next, it invokes the Propogate_Change method in its parent, an Order Instance object 364, as shown in FIG. 27. The Order Instance object 364 places an entry into the change stack identifying itself (e.g., its name, etc.) and invokes Propogate_Change in its parent, an Order object 358. The Order object 358 indicates that it changed and notifies its parent, a Composite Order 357. The Composite Order 357 pushes an entry into the stack and propagates the call up to its parent, a Result Node 359. The Result Node 359 pushes an entry into the stack and propagates the call up to its parent, a Node object 352. The Node object does the same and propagates the call to the Plan object 360 that contains the Node. The Plan object 360 is the top level component. It provides the stack object with the call to the change event notification service. This service distributes the change notice to all GUI clients that have registered for change notices for this particular Plan object.

Continuing the example, the client application receives the change notices and extracts the change stack object from the change event. The top entry in the change stack indicates that a change occurred in a specific patient's plan. If the client is no longer interested in changes to that plan, the notice may be ignored. If the client is currently displaying some aspect of the plan, it looks further into the change stack to see which node changed. If the client is interested in changes to the specific node, it looks within to find the result node 359, the composit order 357, the order 358 and so on. If it happens that the client is currently displaying the attribute that changed, it will find the new value at the very bottom of the stack. With this method, any change in a plan will be reflected on any user who is using the plan in real time.

b. Factory Object Interface

Figure 28:
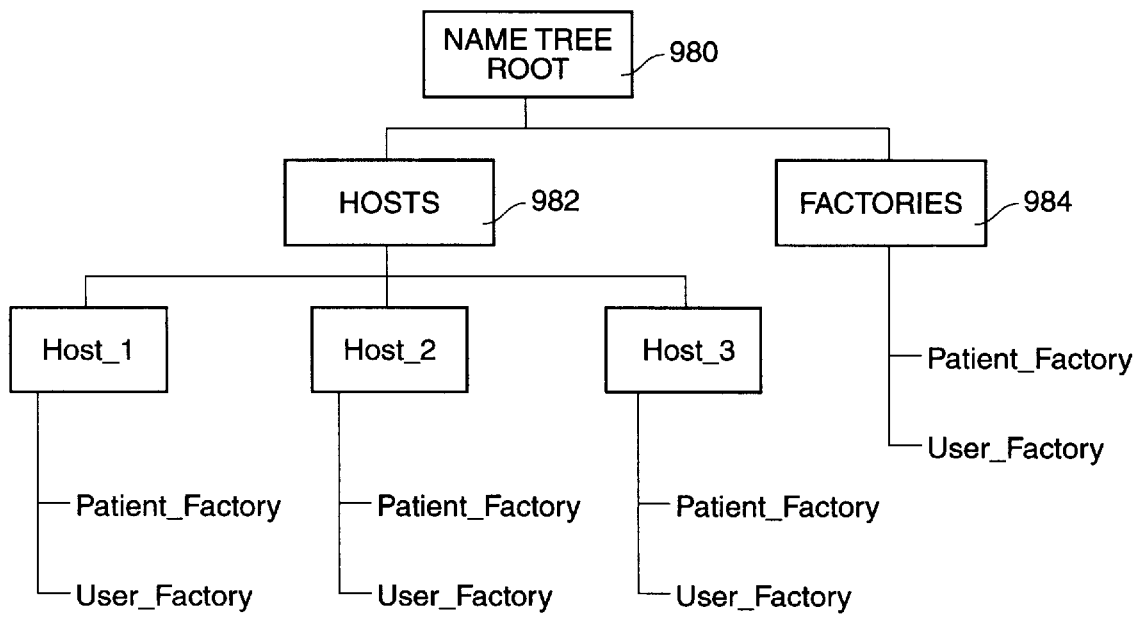
FIG. 28 illustrates the creation of instances on different host machines according to the present invention.

A factory object 305, as shown in FIG. 26, is an object that creates new instances of an object. Almost every server object class will have a corresponding Factory object class. Factories are arranged in the name tree to facilitate the creation of instances on different host machines, as illustrated in FIG. 28. A Hosts directory 982 and Factories directory 984 is listed in the Name Tree Root 980 (among others). The Factories directory 984 contains a list of all the object factories in the system. The Hosts directory 982 contains references to specific host directories that exist on the hosts they represent (e.g., the Host_1 name context object runs on a computer host named "Host_1"). Each host directory contains a list of factories for all the objects that may be hosted on that machine (i.e., a user can control which hosts are to run which objects by including or excluding the object's factory in the host directory).

An object that wishes to create a new object instance on a specific host will invoke the Create_New method 308 in the factory corresponding to the desired object and specify the name of the host on which the new object will reside. If a host is specified, the factory traverses the name tree through the hosts directory 951 to find the factory residing on the desired host and forwards the Create_New request to that factory (without specifying a host name). When a factory receives a create request without a host name, it creates the object instance on its own host.

Other factories, in alternate embodiments, may look at the load and capacity of a collection of hosts and allocate the new object to the host with the most available storage and CPU capacity.

c. Container Object Interface

All of the GUI server objects that function as containers support the standard container interfaces (as seen in FIG. 26) in addition to the standard server object interfaces. The Container object 306 interfaces provide client objects with a standard way to add and remove items from containers, obtain an item within a container (the Resolve method 309), and list the names of the items within the container. In an embodiment, these interfaces will conform to the CORBA Standard Services 2.0 specification for containers. In an alternate embodiment, the container services may be able to use other environments, such as MAC windows.

2. Library

Every user may have their own library or link to a common library shared by others. The library function is implemented to handle a hierarchy of libraries that roughly correspond to the organization's structure (e.g., network, facilities, departments, etc.).

Figure 29:
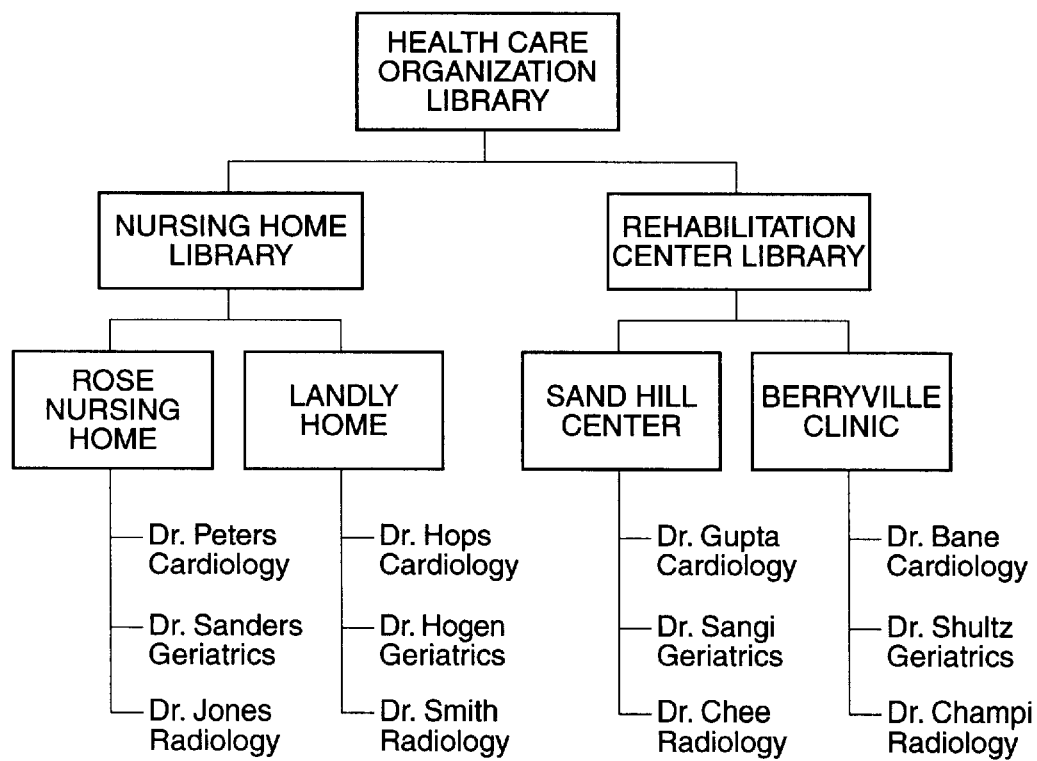
FIG. 29 illustrates an example library hierarchy according to the present invention.

FIG. 29 illustrates an example library hierarchy according to the present invention. Each physician may have their own library. Each library at the bottom of the tree is able to see items up through the hierarchy all the way to the top. Library items added at the top level are available to everyone within the network. Library items placed in the next level down are available to all users working in that type of facility (e.g., Nursing Home or Rehabilitation Center). Items added at the next level down are available to all users within the specific facility. Library items added at the lowest level are only available to the individual user.

The content within a library at a given level in the hierarchy may also be organized in a hierarchy by department and category to organize the items stored in the library. This facilitates retrieval.

a. System_Library Object Interfaces

Figure 30:
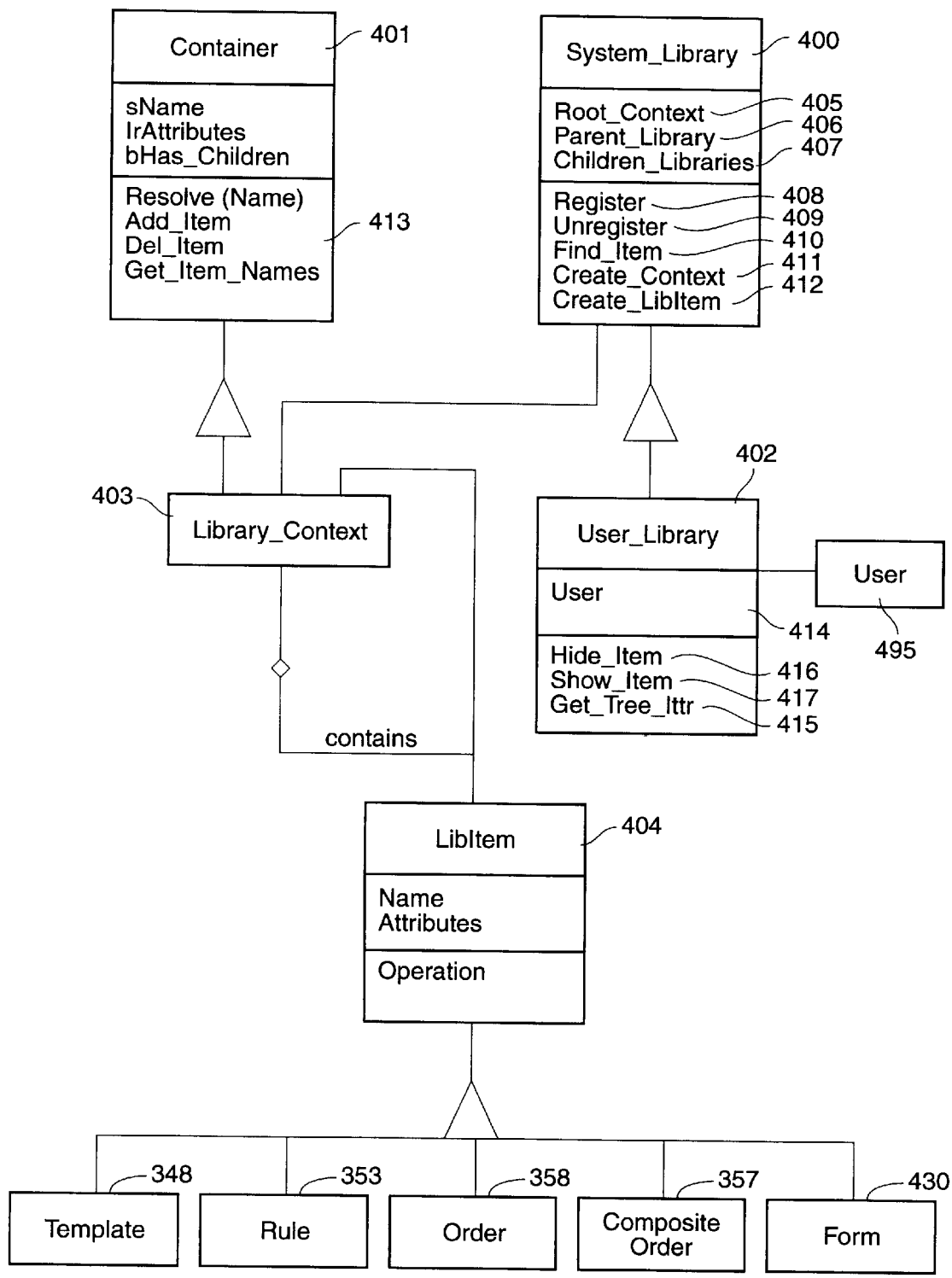
FIG. 30 illustrates a system library interface according to the present invention.

FIG. 30 illustrates the services provided by the library objects and the items contained within the library. System_library objects 400 maintain the hierarchy of libraries across the network. Within a given library exists a collection of items stored in the library. Any client application (as in client-server design) interacts directly with the User_Library objects 402. A User_Library instance is associated with every user 495 and connects to the System_Library hierarchy as a leaf node. User_Library objects 402 traverse up the library hierarchy through the ancestor chain and build a tree of library items from the union of all items in the System_Library object 400. They allow the client applications to set preferences that identify which items are displayed (presumably frequently ordered items) and which items are hidden (items a given user does not typically use).

(i) Root Context Attribute

The Root_Context attribute 405 holds the object reference to the root container of the library at this level in the hierarchy. This container holds other containers and the top level library items in this library.

(ii) Parent Library Attribute

Parent Library attribute 406 maintains the link to the library above this one in the hierarchy.

(iii) Children Libraries Attribute

Children Library attribute 407 maintains references to the libraries below this on in the hierarchy.

(iv) Register and Unregister Methods

Register and Unregister methods 408 and 409 allow client applications to register and unregister for notifications of changes made to the library. When registered, a client application will receive notice when items change in the library at this level.

(v) Find Item Method

The Find_Item method 410 allows a client application to search through the library to find all the items that match the specified attributes and search criteria. The method returns a container holding the matching library items, or actually references to the items.

(vi) Create Context and Create LibItem Methods

The System_Library object 400 serves as an object factory for library context (container 401) and library item objects. Create Context and Create LibItem methods 411 or 412 create a new instance of the specified type of object. The new instance is not associated with a context and is essentially empty. The client application is expected to initialize the object and insert it into the appropriate context (by traversing to the desired context and invoking the Add_Item method 413 with the reference of the new object).

b. User Library Object Interfaces

The User_Library object 402 provides an interface to the client components. Its principle function is to provide an iterator to client components that allows them to iterate through the library items the user has indicated they wish to see.

(i) User Attribute

The User attribute 414 provides a link to the User object 405 associated with a specific GUI user. In an embodiment, every User_Library object 402 instance is associated with one user.

(ii) Get_Tree_Iterator Method

The Get_Tree_Iterator method 415 returns an iterator object that is able to traverse through the tree of library items. The library tree iterator object is able to return references to library items the user has not hidden (using the Hide_Item method 416). The library tree iterator is able to keep abreast of library changes (in near real-time) and returns only current references to client components (e.g., a client invokes the Get_Tree_Iterator method 415 and begins traversing the tree, then another user adds a library item somewhere in the hierarchy; the iterator will return the reference to the new item if it traverses the area in the tree where the new item was just added).

(iii) Hide_Item Method

The Hide_Item method 416 allows a user to remove an item from the tree that the library iterator traverses through. Once hidden, the library iterator will not return the reference to the item. The item may be brought back using the Show_Item method 417.

(iv) Show-Item Method

The Show_Item method 417 searches through the library hierarchy for the specified item and, if it finds one, includes it in the tree of items the library iterator traverses through.

c. LibContext Object Interfaces

The LibContext object 403 inherits interfaces from the general Container object. It may contain other LibContext objects or LibItem objects.

d. LibItem Object Interfaces

The LibItem object 404 specifies interfaces that all library objects must support (e.g., inherit from).

e. Library Item Objects

Each type of library object, as shown in FIGS. 27 and 30, possess interfaces specific to the object class. These interfaces are discussed in detail below.

3. Template, Plan and Patients

This section describes the interfaces for the GUI server objects. FIG. 27 illustrates the relationships between the GUI server objects.

a. Template Object Interfaces

Template objects 348 are stored in either the system or user library. They contain Virtual Time Slot objects 349 that, in turn, contain Node objects 352 and Template objects 348. A template object 348 can also be embedded within another template (i.e., as a sub-plan). Template objects 348 have a name and attributes like all GUI server objects. They also support the Container and Archive interfaces.

(i) Start_Node Attribute

Start_Node attribute 370 allows clients to obtain the first node in the template, the start node. From this node, the client can traverse through all of the nodes in the plan.

(ii) Get_Node_List_Attribute

A client may get a list of object references to all the nodes in a template by invoking the Get_Node_List attribute 371. This attribute returns a list of object references.

(iii) Get_Time_Slot_List Attribute

A client may get a list of the virtual time slot objects in the template by invoking the Get_Time_Slot_List Attribute 372. This attribute returns a list of object references.

(iv) Lock and Unlock Methods

Clients that wish to make changes to a template will need to obtain a lock on a template instance. The Lock method 373 allows clients to obtain a lock or indicates the template is currently locked by another client. Clients must obtain a lock before making changes to a template. Once the changes are complete, they must call the Unlock method 374 to free the template instance so that other clients may make changes. Clients that only need to view a template (without making changes) need not obtain a lock on the template, but they should register to receive change notifications so they can show users updates to the template when changes are made by others.

(v) Register and Unregister Methods

Clients that wish to be notified when changes occur in templates must register with the template object instance by using register method 375. When they no longer wish to receive change notifications, they should unregister by using unregister 376.

b. Plan Object Interfaces

Plan objects 360 represent the patient's integrated plan. There is one instance of a Plan object for every patient. These objects contain all the orders from assigned templates. A Plan contains a network of Node objects 352 for Orders that have not yet been scheduled. Scheduled orders are moved into the Real Time Slot object 363 corresponding to the scheduled start time of the Order.

c. Patient Object Interfaces

Patient objects 361 represent patients in the GUI system. There is one instance of a Patient object for each patient. The Patient object maintains connections to the patient's plan object 360, history object 362 and other items (e.g., medications, conditions and alerts).

d. History Object Interfaces

History objects 362 maintain the order history for the patients in the GUI system. There is one instance of a History object for each patient. The History object 362 maintains connections to the object archives 307 (see FIG. 26) for all of the orders that have been completed for the patient. It also maintains indices to facilitate fast searches based on templates and orders, and time period.

e. Virtual Time Slot Object Interfaces

Template objects 348 contain a list of Virtual Time Slot instances for each time slot in the template. Virtual Time Slot objects 349 maintain the state of individual time slots in a template.

f. Real Time Slot Object Interfaces

The Real Time Slot Objects 363 represent actual time intervals. They are contained within Plan objects to hold orders scheduled to start within a specific time interval. Real time slot objects 363 indicate their start time and duration. When orders are scheduled, they are moved from nodes into Real Time Slot Objects. The Scheduling and tasks management client software uses the time slots to display tasks scheduled for individual users.

g. Result Node Object Interfaces

The Result Node objects 359 represent the list of result nodes that can proceed from a Node object 352. Result Node objects 359 maintain information on the result node and the decision nodes to allow the clients to reconstruct a full node triplet by combining the information from the Node object 352 and the Result Node objects 359.

h. Composite Order Object Interfaces

Composite orders 357 are containers for multiple orders that are grouped together.

i. Order Object Interfaces

The Order object 358 fully describes generalized orders in the GUI system. The Order Instance object 364 maintains the data that qualify the order, the order's life cycle, and the results gathered when the order is filled. Each order contains at least one order instance object.

j. Order Instance Object Interfaces

Order Instance objects 364 capture the state of an instance of an order. Ongoing orders will have multiple order instances. Each order instance has attributes that qualify the order, hold result values, and mark start and end times. Order Instance objects 364 also have a life cycle object within that maintains the current state of the order and acts on events that transition the order to its various states.

k. If Rule Object Interfaces

If Rule Objects 353 contains three elements: a Probability Attribute 377, Destination attribute 378, and an Expression Object 354. The Probability attribute maintains the probability that the branch associated with this rule is taken (on average). The Destination attribute indicates the nodes that will be activated when the rule fires.

l. Expression Object Interfaces

Expression Objects 354 maintain logical expressions. They not only contain the string representation of the expression, but the references to all the attributes they depend upon. They monitor the life cycle of the orders they depend upon and when the life cycle changes state, they check to see if they can now evaluate the expression.

m. Life Cycle Object Interfaces

Life cycle objects 356 maintain state tables for attributes, orders, templates, plans, etc. The state tables have a state and accept events that advance the life cycle to a new state. It may support the activation of methods when state transitions occur.

n. Attribute Object Interfaces

Attribute objects 355 hold all the data in plans, templates, orders, patients, etc. available to GUI for decision making purposes.

Form Object Interface

Form object 430 (see FIG. 30) provides all attributes associated with an order object 358 for collecting results data. It provides all information needed to display results data in the GUI. The form object can represent any form including HTML forms.

IX. CONCLUSION

The foregoing description of the preferred embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

We claim:

1. A data processing apparatus, comprising:
   a display for displaying data;
   input means for supplying input data;
   a storage location, coupled with the display and the input means, for storing data, images, and programs; and
   processing means, coupled to the display means, the input means, and the storage means, for controlling the storage means, the input means, and the display means in response to stored programs and input data to perform data processing operations;
   wherein the display includes,
      a plurality of graphic icon images, stored in the storage location, arranged on the display representing a medical treatment plan;
   wherein the stored programs includes,
      a program for merging a first set of graphic icon images representing a first treatment plan with a second set of graphic icon images representing a second treatment plan to obtain a combined treatment plan.

2. The apparatus of claim 1, wherein the first set of graphic icon images are assigned to a patient.

3. The apparatus of claim 1, wherein the first set of graphic icon images and the second set of graphic icon images are arranged in a first flow chart view and a second chart view, respectively.

4. The apparatus of claim 1, wherein the first set of graphic icon images includes at least one order triplet, the order triplet having an order node, result node and flow control node.

5. The apparatus of claim 1, wherein the input means includes a mouse.

6. The apparatus of claim 1, wherein the process means includes a processor.

7. The apparatus of claim 1, wherein the first set of graphic icon images includes at least a first icon image having a first medical order description responsive to input data and the second set of graphic icon images includes at least a second icon image having a second medical order description responsive to input data, and the combined treatment plan includes a third icon image representing the first and second medical order description.

8. The apparatus of claim 7, wherein the stored program eliminates duplicate order descriptions in the first medical order and the second medical order.

9. The apparatus of claim 1, wherein the first set of graphic icon images are arranged in a chronological sequence and a first icon image in the first set of graphic icon images represents a medical order.

10. The apparatus of claim 9, wherein the stored program deletes the first order icon image in response to the activation of a delete button corresponding to the first order icon image.

11. The apparatus of claim 9, wherein the stored program adds a second order icon image in response to the activation of an add button corresponding to the second order icon image.

12. A method for displaying a graphic representation of a medical treatment plan, comprising the steps of:
   providing a first set of icon images representing a first medical treatment;
   providing a second set of icon images representing a second medical treatment; and
   combining the first set of icon images with the second set of icon images to obtain a third set of icon images representing a medical treatment including the first and second medical treatment.

13. The method of claim 12, wherein the method further includes the step of arranging the first set of icon images in corresponding time slots with the second set of icon images.

14. The method of claim 12, wherein the step of providing a first set of icon images includes the step of providing the first set of icon images in a flow chart and the step of providing a second set of icon images includes the step of providing the second set of icon images in a flow chart.

15. The method of claim 12, wherein the method further includes the step of assigning the first set of icon images to a patient.

16. The method of claim 12, wherein the method step of providing a first set of icon images includes the step of providing an order triplet.

17. The method of claim 16, wherein the order triplet includes an order node, result node and flow control node.

18. The method of claim 12, wherein the method step of providing a first set of icon images includes the step of providing a first order icon image having a corresponding order description and the method step of providing a second set of icon images includes the step of providing a second order icon image having a corresponding order description.

19. The method of claim 18, wherein the combining step further includes the step of comparing the first order description to the second order description.

20. The method of claim 19, wherein the combining step further includes the step of detecting conflicting order descriptions in the first order description and the second order description.

21. The method of claim 19, wherein the combining step further includes the step of removing a duplicate order description in the first order description and the second order description.

22. The method of claim 21, wherein the duplicate order is removed in response to a user supplied rule.

23. An article of manufacture having computer readable program code means embodied therein for displaying a medical treatment plan, the computer readable program code means in the article of manufacture comprising:
   computer readable program code means for causing a computer to generate an image on a display representing a first medical treatment;
   computer readable program code means for causing a computer to generate an image on a display representing a second medical treatment; and
   computer readable program code means for causing a computer to combine the image representing the first medical treatment with the image representing the second medical treatment to display a combined medical treatment image.

24. The article of manufacture of claim 23, wherein the article of manufacture further includes a computer readable program code means for causing a computer to generate a chart view of the image representing the first medical treatment and the image representing the second medical treatment.

25. The article of manufacture of claim 23, wherein the article of manufacture further includes: computer readable program code means for causing a computer to generate the image of the first medical treatment in time slots on a display corresponding to the image of the second medical treatment.

26. The article of manufacture of claim 23, wherein the article of manufacture further includes a computer readable means for causing a computer to assign the image representing the first medical treatment to a patient.

27. The article of manufacture of claim 23, wherein the image representing the first medical treatment includes an order icon image having a corresponding order description.

28. The article of manufacture of claim 27, wherein the order icon image is an order triplet including an order node, a result node and a flow control node.

29. The article of manufacture of claim 28, wherein the article of manufacture further includes computer readable means for causing a computer to assign a result value to the result node image.

30. The article of manufacture of claim 27, wherein the image representing the second medical treatment includes an order icon image having a corresponding order description.

31. The article of manufacture of claim 30, wherein the article of manufacture further includes computer readable means for causing a computer to compare the first order icon image description to the second order icon image description.

32. The article of manufacture of claim 30, wherein the article of manufacture further includes computer readable means for removing duplicate order descriptions in the combined medical treatment.

* * * * *